(12) United States Patent
Pommer et al.

(10) Patent No.: US 9,549,744 B2
(45) Date of Patent: Jan. 24, 2017

(54) SPINAL PROBE WITH TACTILE FORCE FEEDBACK AND PEDICLE BREACH PREDICTION

(75) Inventors: Timothy J. Pommer, St. Paul, MN (US); David W. Polly, Jr., Edina, MN (US); David J. Nuckley, Minneapolis, MN (US); Evan M. Gustafson, Golden Valley, MN (US); Charles Gerald Tan Ledonio, Minneapolis, MN (US); Arthur G. Erdman, New Brighton, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1414 days.

(21) Appl. No.: 13/378,597

(22) PCT Filed: Jun. 15, 2010

(86) PCT No.: PCT/US2010/038654
§ 371 (c)(1),
(2), (4) Date: Mar. 30, 2012

(87) PCT Pub. No.: WO2010/147972
PCT Pub. Date: Dec. 23, 2010

(65) Prior Publication Data
US 2012/0179070 A1    Jul. 12, 2012

Related U.S. Application Data

(60) Provisional application No. 61/187,491, filed on Jun. 16, 2009.

(51) Int. Cl.
*A61B 5/103* (2006.01)
*A61B 5/117* (2016.01)
(Continued)

(52) U.S. Cl.
CPC ......... *A61B 17/1671* (2013.01); *A61B 5/6843* (2013.01); *A61B 5/6848* (2013.01);
(Continued)

(58) Field of Classification Search
CPC ... A61B 5/6843; A61B 5/6848; A61B 5/6849; A61B 17/1626; A61B 1/1671; A61B 2562/046; A61B 2017/00022; A61B 2017/00221; A61B 2562/0247; A61B 2562/043
(Continued)

(56) References Cited

U.S. PATENT DOCUMENTS 4,762,134 A    8/1988 Gala
5,353,800 A    10/1994 Pohndorf et al.
(Continued)

FOREIGN PATENT DOCUMENTS

EP    1 815 949 A1    8/2007
WO    02/36018 A1    5/2002
WO    2009/055034 A1    4/2009

OTHER PUBLICATIONS

Kuklo et al. "Surgical Anatomy of the Thoracic Pedicle," Seminars in Spine Surgery, vol. 14, No. 1, pp. 3-7, Mar. 2002.
(Continued)

*Primary Examiner* — Max Hindenburg
*Assistant Examiner* — Jonathan M Foreman
(74) *Attorney, Agent, or Firm* — Shumaker & Sieffert, P.A.

(57) ABSTRACT

A spinal probe comprises a handle, a shaft coupled to the handle and a force sensor to detect forces applied to a tip of the shaft. A controller that executes a predictive algorithm to predict whether or not the tip of the shaft is going to breach a cortex of a pedicle based on the detected forces. The controller may be embedded within the spinal probe or
(Continued)

external within a computer or other device coupled to the probe by a data acquisition component.

34 Claims, 66 Drawing Sheets

(51) Int. Cl.
*A61B 17/16* (2006.01)
*A61B 5/00* (2006.01)
*A61B 17/00* (2006.01)

(52) U.S. Cl.
CPC ........ *A61B 5/6849* (2013.01); *A61B 17/1626* (2013.01); *A61B 5/407* (2013.01); *A61B 2017/00022* (2013.01); *A61B 2017/00221* (2013.01); *A61B 2562/0247* (2013.01); *A61B 2562/043* (2013.01); *A61B 2562/046* (2013.01)

(58) Field of Classification Search
USPC .................................................. 600/587–595
See application file for complete search history.

(56) References Cited

U.S. PATENT DOCUMENTS

| | | | |
|---|---|---|---|
| 5,445,166 A | 8/1995 | Taylor | |
| 6,405,072 B1 | 6/2002 | Cosman | |
| 6,434,507 B1 | 8/2002 | Clayton et al. | |
| 6,546,277 B1 | 4/2003 | Franck et al. | |
| 6,706,005 B2 | 3/2004 | Roy et al. | |
| 6,847,841 B1* | 1/2005 | El Hatw | A61B 5/04 600/547 |
| 6,920,347 B2 | 7/2005 | Simon et al. | |
| 7,039,866 B1 | 5/2006 | Rosenberg et al. | |
| 7,107,091 B2 | 9/2006 | Jutras et al. | |
| 7,206,627 B2 | 4/2007 | Abovitz et al. | |
| 7,335,200 B2 | 2/2008 | Carli | |
| 2007/0106306 A1* | 5/2007 | Bodduluri | A61B 17/32053 606/133 |
| 2008/0249467 A1 | 10/2008 | Burnett et al. | |

OTHER PUBLICATIONS

White et al., "Clinical Biomechanics of the Spine," chapter 8, Biomechanical Considerations in the Surgical Management of the Spine, 2nd Ed., Philidelphia: Lippincott-Raven Publishers, 1990, pp. 512-610.

Inceoglu et al., "Trabecular Architecture of the Lumbar Vertibral Pedicle," Spine, vol. 30, No. 13, pp. 1485-1490, Jul. 1, 2005.

Lehman et al., "Biomechanics of Thoracic Pedicle Screw Fixation, Part I: Screw Biomechanics," Seminars in Spine Surgery, vol. 14, No. 1, pp. 8-15, Mar. 2002.

Kothe et al., "Internal Architecture of the Thoracic Pedicle: An Anatomic Study," Spine, vol. 21, No. 3, pp. 264-270, Feb. 1996.

Panjabi et al., "Human Lumbar Vertebrae—Quantitative Three-Dimensional Anatomy," Spine, vol. 17, No. 3, pp. 299-306, 1992.

Panjabi, "Thoracic Human Vertebrae—Quantitative Three-Dimensional Anatomy," Spine, vol. 16, No. 8, pp. 888-901, 1991.

Panjabi et al., "Human Cervical Vertebrae—Quantitative Three-Dimensional Anatomy of the Middle and Lower Regions," Spine, vol. 16, No. 8, pp. 861-869, 1991.

O'Brien et al., "Biomechanics of Thoracic Fixation in Deformity, Part II, Hooks Versus Screws," Seminars in Spine Surgery, vol. 14, No. 1, pp. 16-34, Mar. 2002.

Merloz, "Fluoroscopy-based Navigation System in Spine Surgery," Journal of Engineering Medicine, vol. 221, Part H, pp. 813-820, Jul. 2, 2007.

Gaines, Jr., "The Use of Pedicle-Screw Internal Fixation for the Operative Treatment of Spinal Disorders," The Journal of Bone and Joint Surgery, vol. 82-A, No. 10, pp. 1458-1476, Oct. 2000.

Rampersud et al., "Accuracy Requirements for Image-Guided Spinal Pedicle Screw Placement," Spine, vol. 26, No. 4, pp. 352-359, 2001.

Youkilis et al., "Sterotactic Navigation for Placement of Pedicle Screws in the Thoracic Spine," Neurosurgery, vol. 48, No. 4, pp. 771-778, Apr. 2001.

Maruyama et al., "Surgical Treatment of Scoliosis: A Review of Techniques Currently Applied," Scoliosis, vol. 3, No. 6, Apr. 18, 2008.

Harrington, "Treatment of Scoliosis. Correction and Internal Fixation by Spine Instrumentation," Journal of Bone and Joint Surgery, vol. 44-A, No. 4, pp. 591-610, Jun. 1962.

Moore et al., "Introduction to the Practice of Statistics," Chapter 6.1: Estimating with Confidence, 6th Ed., New York: W.H. Freemand and Company, 2009, pp. 356-369.

White et al., Clinical Biomechanics of the Spine, Chapter 3: Practical Biomechanics of Scoliosis and Kyphosis, 2nd Ed., Philadelphia: Lippinoctt-Raven Publishers 1990, pp. 127-169.

Ludwig, "Cervical Pedicle Screw—Comparative Accuracy of Two Insertion Techniques," Spine, vol. 25, No. 20, pp. 2675-2681, Oct. 15, 2000.

International Preliminary Report on Patentability, from corresponding PCT Application Serial No. PCT/US2010/038654, mailed Dec. 29, 2011, 10 pages.

International Search Report and Written Opinion, from corresponding PCT Application Serial No. PCT/US2010/038654, mailed Sep. 22, 2010, 17 pages.

\* cited by examiner

SPINAL PROBE WITH TACTILE FORCE FEEDBACK AND PEDICLE BREACH PREDICTION

This is a National Stage filing under 35 U.S.C. 371 of International Application No. PCT/US2010/038654, filed Jun. 15, 2010, which claims priority to U.S. Provisional Application No. 61/187,491, filed Jun. 16, 2009, the entire contents of which are incorporated herein by reference.

TECHNICAL FIELD

The invention relates to spinal surgical instruments and, more specifically, to a spinal probe for assisting the placement of medical instrumentation into and between spinal vertebrae.

BACKGROUND

When an orthopedic surgeon performs spinal surgery involving vertebral fixation, the surgeon typically uses a pedicle awl or drill in a predrilling process to form a pilot hole in a patient's vertebrae. The surgeon then inserts pedicle screws during a screw placement process for placement of stabilization rods or plates so as to fuse two or more of the vertebrae. During this process an orthopedic surgeon typically depends on a thorough understanding of the spine's anatomy as well as an acquired knowledge of tactile feedback in order to successfully prepare the vertebra for the insertion of pedicle screws. However, due to the nature of the surgery, complications often arise that result in injury to the patient.

For example, several reports have been published describing complications associated with insertions of pedicle screws. Typically, screw misplacement includes inferior, lateral, superior, and medial breaches. Even the smallest directional error in the pedicle screw placement procedure can result in a significant error in the position of the tip of the screw. Bone disorders, such as scoliosis or osteoporosis, further complicate the procedure and lead to screw misplacement. Further, as the spine ascends, each vertebra becomes anatomically smaller. The variability in pedicle dimensions makes pedicle screw insertion a delicate operation with the potential for catastrophe. These catastrophes include breaching the cortex with either the pedicle awl in the predrilling process or with the pedicle screw during the screw placement process. An additional source of failure is when a pedicle screw breaks within the bone.

Common complications arising from misplaced pedicle screws include vascular and visceral injuries. Vascular and visceral injuries can include trauma to the aorta, vertebral arteries, azygos vein, esophagus, and lung. In addition, neurological complications may arise including injury to the spinal cord and nerve roots. These injuries can be as severe as complete paralysis to mild paresis. Neurological complications in the lumbar and lower thoracic spine typically cause paresis below the waist while complications in the cervical spine may cause paresis in the arms as well as the legs.

As another example, there are many critical structures within the thoracic cavity which make pedicle placement in the thoracic spine difficult. Critical tissues that a misplaced pedicle may come into contact with include the lung, azygos vein, the esophagus, and the aorta.

One obstacle facing physicians placing pedicles is the lack of visualization. The amount of tissue obstructing the view of the spine makes the placement of pedicles screws difficult simply because it is difficult to see the pedicle. Furthermore, the complex three-dimensional anatomy of the pedicle further complicates the process. Inter-patient variability, especially in diseased spines such as scoliosis, has resulted in imprecise placement of pedicle screws when surgeons rely on anatomic landmarks alone. In response to the need for better visualization, many companies have developed visualizations suites that help surgeons predict their trajectory when placing pedicle screws.

There are several medical device companies that have developed image guidance visualization systems for assisting in the placement of pedicle screws. In general, the systems acquire a medical image preoperatively and co-register the image with a motion capture system that reacts to the movement during the surgical process. The result is an intraoperative visualization system that depicts the pedicle screw in registration with anatomy that would not otherwise be seen during surgery.

There is no doubt that image guided visualization has helped spinal surgeons more effectively place pedicle screws. However, any breach of the cortex due to a misplaced pedicles screw is unacceptable and even with image guidance, errors are still prevalent in pedicle screw procedures. Furthermore, the systems themselves are not error free. Errors within the image guidance systems themselves could include surface generation errors, errors in fixing of the tracking devices to the patient, intraoperative data noise, registration errors, and inaccuracy of surgical probes. Therefore, surgeons understand that image guidance systems are not a substitute for skill and expertise.

SUMMARY

In general, a spinal probe with tactile force feedback and pedicle breach prediction is described. The spinal probe includes an internal force sensor to capture the tactile sensation present in the pedicle tract procedure. The force sensor may sense forces at the tip of a shaft of the spinal probe in all directions as well as their corresponding moments present during a surgery while the probe is inserted into a pedicel or other spinal bone of the patient. As another example, the force sensor may sense a reduced set of forces, such as forces along x and y axis and a moment around a z axis relative to the shaft of the sensor, where the z axis is parallel to the shaft and the x and y axes are in a plane orthogonal to the shaft. Furthermore, the spinal probe may include a controller that, based on these forces, predicts in real-time (i.e., during surgery) impending pedicle breaches before the breach occurs. Alternatively, the spinal probe may be coupled to a data acquisition system that executes the breach prediction algorithm. In either case, an output signal provides cues (e.g., visual and/or audible signals) to the surgeon that are representative of real-time tactile feedback and provide a warning in the event an imminent breach is predicted.

During spinal surgery, there currently exists no feedback device to convey the tactile forces a surgeon is feeling during the pedicle tract procedure. This limits the ability for resident surgeons to fully understand the procedure, creating a longer and more difficult learning period, and increasing the chance for catastrophic failure. Instead of depending exclusively on intuition, experience, and tactile feedback, the probe described herein provides a measured and relayed force profile would provide surgeons with an additional piece of feedback upon which they can rely.

Although image-guided visualization systems have been a tremendous help to surgeons performing the pedicle tract procedure, pedicle screws are still misplaced, exemplifying the need for quantifying the tactile feedback in the pedicle tract procedure. Instead of depending exclusively on intuition, experience, and feel, a measured and relayed force profile provided by the system described herein provides surgeons with an additional piece of feedback upon which they can rely.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 38: Torque as a function of distance at 200 g.

DETAILED DESCRIPTION

Figure 1:
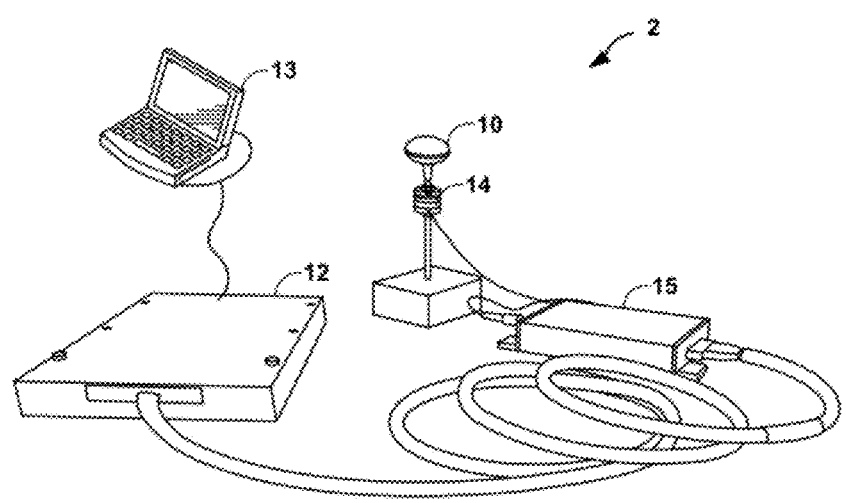
FIG. 1: A data analysis system including a data acquisition module (left), a signal conditioner, and a pedicle probe with an axially mounted load cell.

FIG. 1 is a schematic diagram of a system 2 including a spinal probe 10, a signal conditioner 15, and a data acquisition module 12 coupled to a computer 13. Spinal probe 10 is capable of measuring forces present during a pedicle tract procedure. Signal conditioner converts 12 raw voltages into a calibrated signal that can be read by the acquisition module 32. Data acquisition module 12 then converts the signal from the signal conditioner to a readable signal used for acquiring data on a computing device 13, such as laptop computer or dedicated surgical display device.

In the example of FIG. 1, spinal probe 10 includes an axially-mounted force sensor 14 and is sized and shaped similar to a standard pedicle awl. In one embodiment, the probe itself is similar to what is currently used in surgery. That is, the size, shape, and weight mimics existing probes in order to eliminate the need for a surgeon to learn new techniques. The sensor captures forces appropriate to those seen in the spine surgery. The range of forces may be approximately 10-20 lbf in the axial direction. In one embodiment, sensor measures the forces in six degrees of freedom. This includes the forces in the x, y, and z directions as well as their corresponding moments. A full explanation of the forces specific to the pedicle tract procedure can be found below.

Further, the size of the sensor is small in order so as not to inhibit the procedure as well as to not alter the feel of the current probe. This includes a small diameter, short height, and low weight. Finally, in some embodiments, the sensor is sensitive enough to capture all the forces present. A data analysis system coupled to the probe samples at a frequency such that the sensor is accurate at low forces. In one embodiment, the spinal probe conforms to the following:

|  | Metric | Units |
| --- | --- | --- |
| Force range | 0 to 20 | Lbf |
| Height | Less than 1.5 | Inch |
| Diameter | Less than 1.5 | Inch |
| Weight | Less than 2 | Lbs |
| Resolution | Less than 2% of max | Lbf |
| Accuracy | Less than 2 | Lbf |

Additionally, as described herein, the probe and the data analysis system is portable and can easily transported between the OR, the laboratory, and different testing environments.

Data analysis system 12 includes a controller (e.g., a processor coupled to memory) that executes a predictive algorithm used to determine whether or not the tip of the probe is going to breach the cortex of the pedicle of a patient during surgery based on forces sensed by the load cell during the procedure. In one example, the predictive algorithm converts the axial forces (Fx and Fy) sensed at the tip of the probe to a radial force, where the axial forces lie in a plane that is orthogonal to the shaft. The techniques described herein recognize that the surgeon tends to significantly rotate the probe while inserting the probe through a spinal bone, e.g., pedicle, long bone or other spinal bone, of the patient. As a result, the sensed axial component forces relative to the bone continuously change in the x and y directions. In one embodiment, the breach predicting algorithm converts the component axial forces (Fx and Fy) to a single radial force and uses the magnitude of radial force along with the moment around a z axis along the shaft for predicting a breach of the bone and alerting the surgeon. When the algorithm predicts a breach is likely to occur, the probe 10, data acquisition system 12 or computer 13 coupled thereto alerts the surgeon to alter the probe's trajectory. In one embodiment, the controller (e.g., an embedded processor and supporting hardware) is embedded within probe 10. In another example, the predictive algorithm executes on computer 13 which presents a user interface that provide cues (e.g., visual and/or audible signals) to the surgeon that are representative of real-time tactile feedback and provides a warning in the event an imminent breach is predicted.

The techniques described in this disclosure may be embodied or encoded in a computer-readable medium, such as a computer-readable storage medium, containing instructions. Instructions embedded or encoded in a computer-readable medium generally cause a programmable processor, or other processor, to perform the method, e.g., when the instructions are executed. Computer readable storage media include, for example, random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Figure 2:
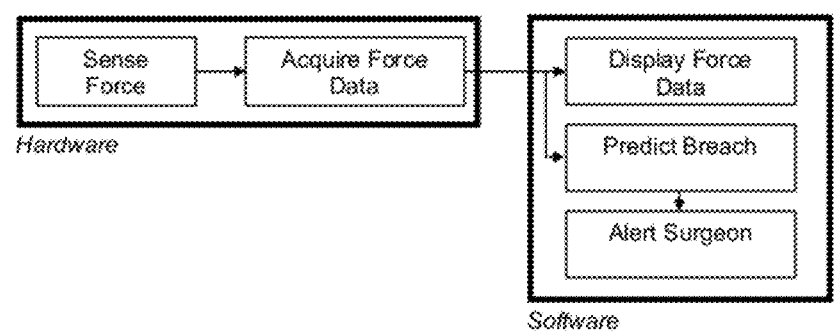
FIG. 2: Exemplary design architecture.

FIG. 2 is a block diagram illustrating the components of the system 2 organized as a hardware element and a software element. The hardware element consists of the spinal probe capable of capturing the forces and an accompanying data analysis system capable of converting the data into a usable format. Software executed by the analysis system may, for example, display force data, predict a breach, and output an alert to the surgeon.

Figure 3:
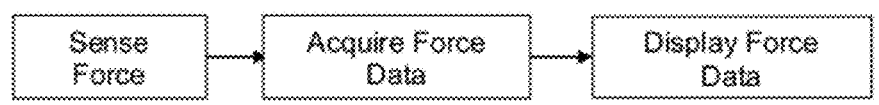
FIG. 3: Exemplary functional block diagram.

In this way, the primary functional tasks of the spinal probe and the accompanying data analysis system are to sense the force, acquire the data, and present the data including any alerts. These functions can be seen in FIG. 3. In an alternative example, a controller embedded within the probe (e.g., on a printed circuit board within the handle) executes the prediction algorithm(s) and outputs an alert to the surgeon.

Figure 4:
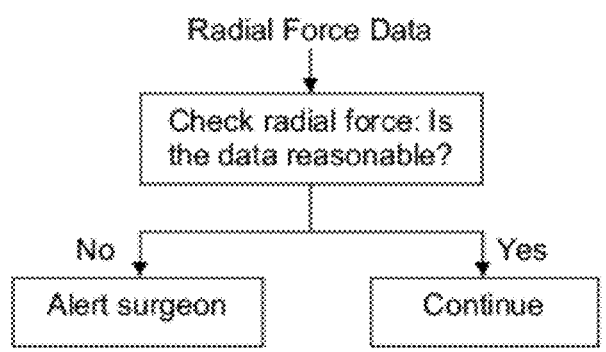
FIG. 4: Exemplary functional block diagram for algorithm.

In either case, the predictive algorithm's primary functions are to take in the force data, interpret the data, and indicated whether or not a breach was likely to occur. These functions in block diagram form are in FIG. 4. As shown, the predictive algorithm is comprised of three basic parts. First is the input radial force data. This data is taken into the algorithm as x and y axial component forces from the load cell. The software then converts these forces into a radial force by calculating the magnitude of the x and y forces. The second function of the algorithm is to check the radial force against a mathematical criterion, such as an upper control limit. If the incoming radial force data fails the criterion, the surgeon is alerted to change the current trajectory of the probe. Third, on the other hand, if the incoming data passes the criterion, the surgeon is not alerted to alter the trajectory.

Figure 5:
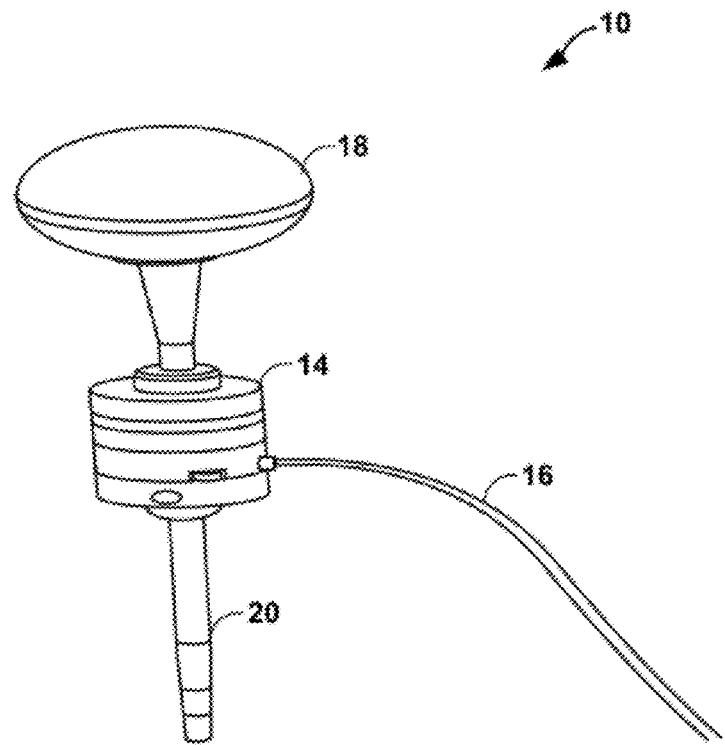
FIG. 5: Spinal probe without motion capture attachment.

FIG. 5 shows an example spinal probe 10 constructed in accordance with the techniques described herein. As shown, the spinal probe is shaped to conform to an industry standard pedicle awl and includes a load cell 14 having an output port 16 for transmitting raw force data. In this example, the spinal probe 10 is a pedicle awl that consists of a large, spherical, handle 18 used for probe manipulation, with a protruding a cylindrical shaft 20. The tip comes to a distinct point, which can be used to navigate the pedicle. In one embodiment, the spinal probe is constructed using a Medtronic pedicle awl, custom built mounting brackets, and a Nano-25 load cell from ATI Industrial Automation.

Figure 6:
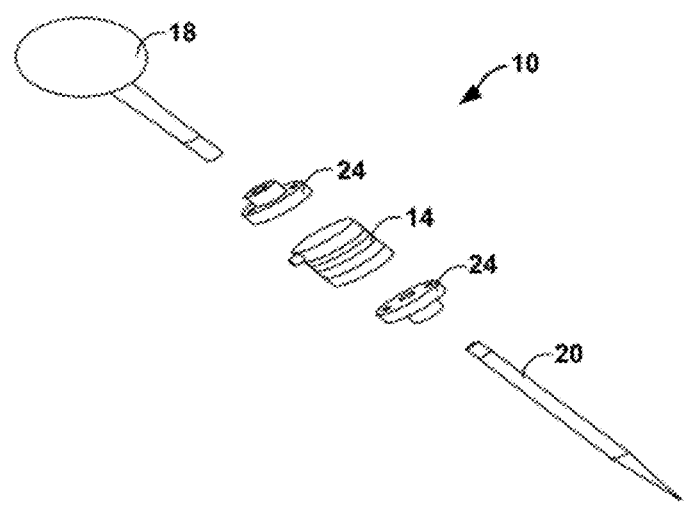
FIG. 6: Axially fixed load cell.

FIG. 6 illustrates an exploded view of the spinal probe 10 having an axially-fixed load cell 14. As shown in FIG. 6, the mounting brackets consist of two cylindrical brackets 24 used to axially mount load cell 14 onto the shaft 20 of the pedicle awl. In this example, the force sensor is able to measure force applied to the shaft in six degrees of freedom, consisting of forces in the x, y, and z directions as well as the corresponding moments. Spinal probe is similar in size, shape, and weight as the current pedicle awls used in the procedure and is able to capture multiple forces present in the procedure. Capturing the forces present during the pedicle tract procedure corresponds to having the spinal probe be capable of capturing large range of forces but still be sensitive enough at low levels in order to capture any small changes in force at the tip.

In this example, a software user interface executing on computing device 13 collects the data, displays the data, and allow the user to control the data collection process. In one embodiment, the software user interface displays the data as a graph showing force as a function of time. In another embodiment, computing device displays a series of icons or vertical bars in which higher vertical bars are illuminated as the sensed force on the shaft of probe 10 increases. With the sampling frequency and file path set by the user, the data can be saved as a text file to be used later in post processing.

Two separate prediction models are described as examples. The first model is based on a 95% confidence interval of the mean of successful pedicle tract procedures. The second is a control chart based approach using an exponentially weighted moving average to determine whether or not the spinal probe would breach the cortex. Both models convert the x and y force data collected by the load cell into a radial force. Similarly, both prediction models cause computer 12 to alert the surgeon if the radial force exceeded a specific value, such as an upper control limit or a tolerance level.

Figure 7:
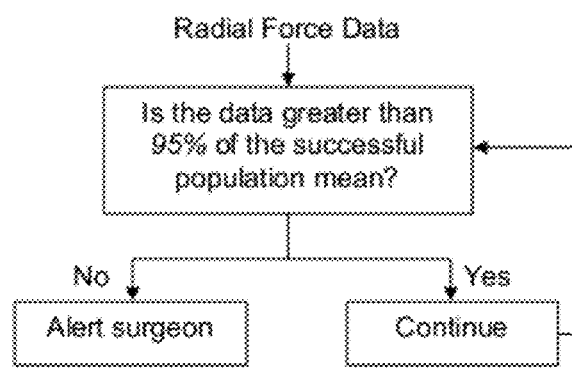
FIG. 7: 95% confidence based interval process flow.

FIG. 7 provides a high-level flowchart of the first predictive algorithm. The first predictive algorithm is based on the mean radial force of trials where there was no breach. This prediction method depends on a database of previous procedures in which the force data was collected. The mean radial force of past successful samples was used as a population mean with a corresponding standard deviation. This population mean and standard deviation were then used to calculate a 95% confidence interval of successful pedicle tract procedural radial force profiles.

As long as the radial force was within 95% of the successful population mean, the spinal probe can continue on its current trajectory. However, once the radial force exceeded the 95% confidence interval of the successful population mean, the spinal probe must be redirected. Therefore the 95% confidence interval serves as a warning level for a breach. Anything within the 95% confidence zone is considered potentially dangerous. This method was tested and proven effective in laboratory models.

Figure 8:
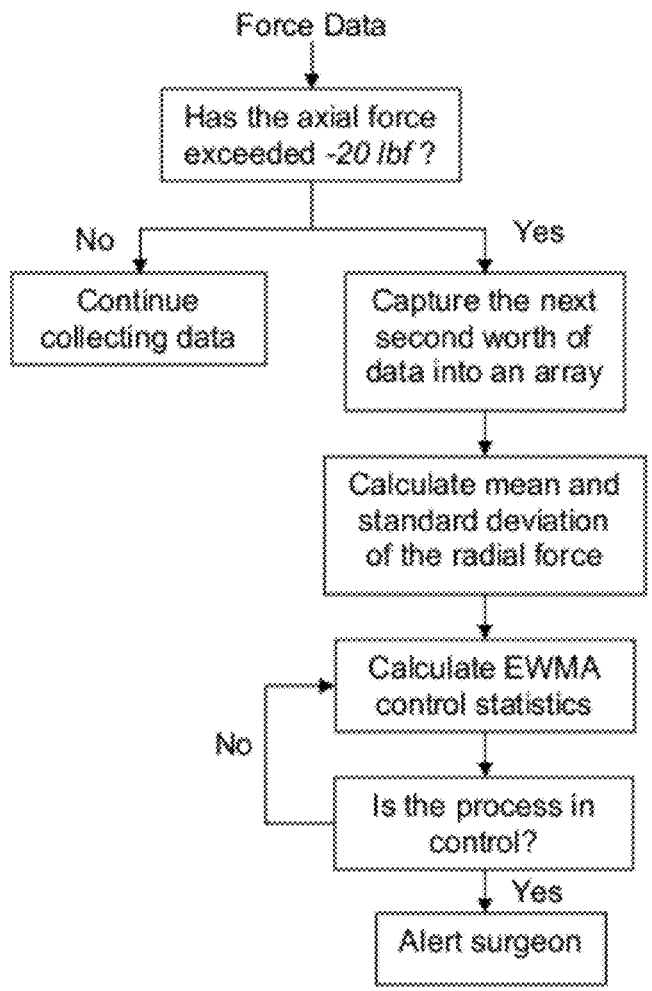
FIG. 8: EWMA control chart-based algorithm process flow.

FIG. 8 provides a high-level flowchart of the first predictive algorithm. The second method of predicting pedicle breaches based on the radial force data took advantage of the statistical models used in quality control. This method of prediction uses an exponentially weighted moving average (EWMA) of the radial forces sensed during the current pedicle surgery to determine whether or not the incoming radial force data is within control, or in other words, within an appropriate range. As soon as the radial force data exceeds a threshold, or rather out of control, the algorithm predicts a breach.

One possible advantage to the EWMA prediction algorithm is that it is not based on past experiments like the 95% confidence interval. This may reduce or eliminate any differences between vertebrae and different spines. Instead, the EWMA algorithm calculates its base statistics during the initial plunge into the pedicle. In one embodiment, this algorithm ignores forces until the axial force exceeds an initial threshold, e.g., the force is beyond −20 lbf, where a negative radial force represents a radial force in the direction of the bone. This axial force value was chosen based on experiments where bone was used as test specimens. All of the experiments had axial force data that well exceeded −20 lbf early in the pedicle tract procedure. Therefore, in order to get a better representation of the mean radial forces, an axial force of −20 lbf triggered the algorithm to begin collecting sample array for the next second. The mean of the one second array beyond −20 lbf defined $\mu_0$. A corresponding standard deviation $\sigma$ was also calculated from the array. These values were then used for determining the exponentially weighted moving average, its corresponding variance, and the upper and lower control limits.

Experimental Results

A spinal probe was constructed using a Medtronic pedicle awl, custom mounting brackets and a Nano-25 load cell from ATI Industrial Automation. A data analysis system was configured using a signal conditioner from ATI Industrial Automation and a National Instruments USB-6221 data acquisition module. A 6061 T6 Aluminum bar was machined into two cylindrical brackets and fixed to the load cell using M3.5 bolts to axially mount the load cell onto the shaft of the pedicle awl.

Multiple tests were conducted in order to characterize a force profile during the pedicle tract procedure. Initially, the spinal probe was first evaluated in a cadaver. This study showed several specific characteristics in the force profile that were then replicated in the laboratory. Laboratory samples included foam, foam and clay, cardboard and clay, and cork and clay. These different samples provided enough evidence to confirm the specific characteristics of the forces when the tip of the spinal probe comes into contact with a boundary. Additionally, the clay and cork sample provided a basis for a method of predicting whether or not a breach was likely to occur.

With the profile characterized, the spinal probe was then used in a study involving eight postmortem pig spines. Varying trajectories were performed in order to differentiate between a successful and an unsuccessful pedicle tract profile. The data from the pig study was also used to test the prediction method set by the clay and cork study. Finally, based on these findings, a recommendation was made for future iterations of the design.

In the cadaver study, the spinal probe was used in conjunction with the Medtronic Stealth Navigation System for a pedicle tract procedure for the lumbar and the first vertebral level of the thoracic spine. Breaches were purposefully made along side with non breach trajectories. Additionally, each trajectory was verified using the Medtronic Stealth Navigation System. This resulted in the collection of a number of force profiles in human bone.

Seven plunges were attempted including vertebral levels T12, L1, L3, L4, and L5. Of the seven plunges, there were three breached vertebrae and four no breach (intact) vertebrae. Of the three breaches, two were medial breaches and one was a lateral breach. Visual confirmation of each plunge was affirmed using the Medtronic Stealth Navigation System. Additionally, the cortex of each pedicle was removed before probing the pedicle.

This study provided information regarding the force profile using the spinal probe. First, the force profile revealed a range of forces seen in a typical pedicle tract procedure. Second, the profile showed distinctive characteristics of breached pedicle when compared to an intact pedicle. Finally, the profile confirmed the prediction of a pedicle breach based on these measurements.

Figure 9:
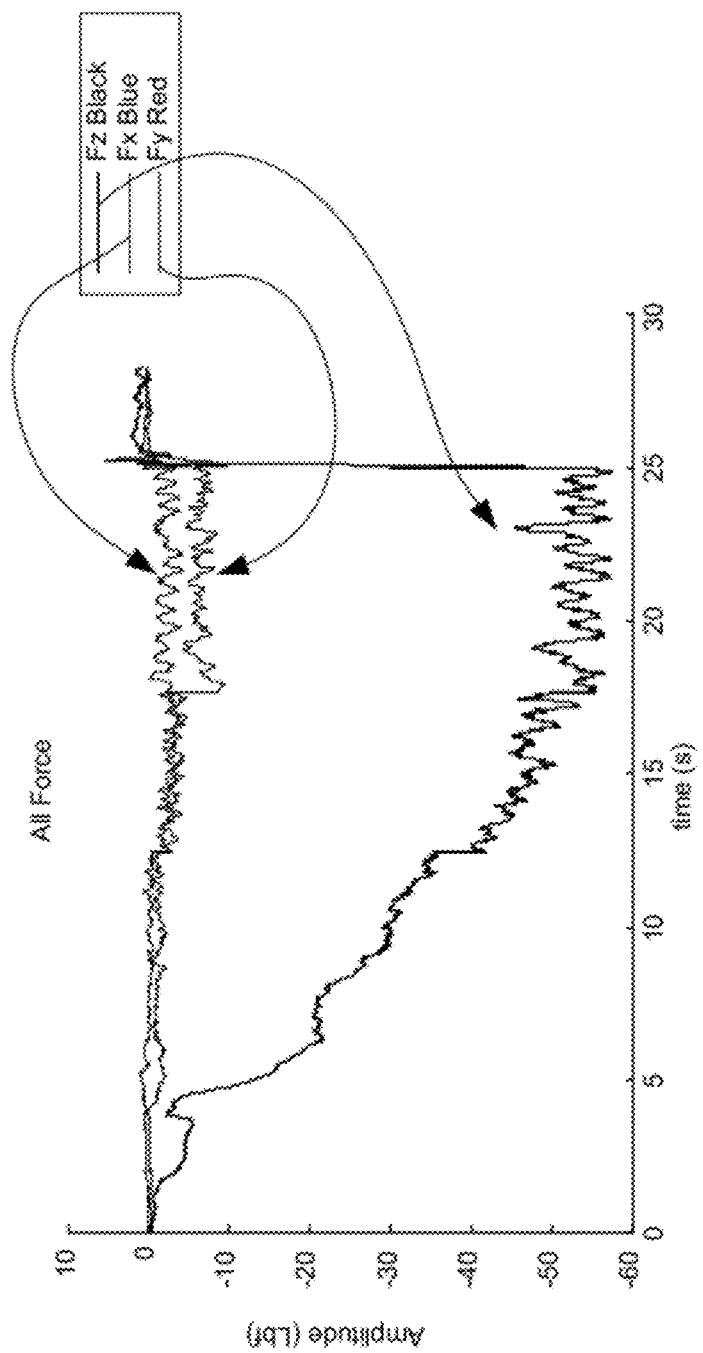
FIG. 9: Profile of a lateral breach in the right pedicle of L5.

In order to get a better understanding of the force profile, the data was post-processed using MATLAB. Only the data corresponding to the plunge was used and all of the pauses were removed. FIG. 9 is a force profile of a lateral breach in the right pedicle of L5 with the pauses removed.

From the plot, three distinct regions were illustrated. The first region consists of the profile between time t=0 seconds to approximately time t=17 seconds. Within this region, the probe has traveled through the cancellous bone within the pedicle in a relatively straight manner. This conclusion is based on the small amount of forces in x (blue) and y (red), and the majority of forces being in z (black). In terms of mechanical forces, there are no radial shear forces from an obstruction and only axial shear forces due to the increasing tapered diameter of the spinal probe. A description of these forces can be found in further detail below.

The second region of the profile begins at approximately time t=17 seconds and ends at approximately time t=25 seconds. Within this region, there is a relative flattening of the force in the z direction and a substantial increase in magnitude of the forces in the x and y directions. From a mechanical force standpoint, this would indicate the tip of the probe has been obstructed. The flattening of the force in the z direction corresponds to the reaction force of the wall while the increase in the forces in x and y would indicate the radial shear force due to the obstruction.

The third and final region would be the large change in the profile at approximately time t=25 seconds. This region characterizes the effect of a breach of the pedicle. At time t=~25 seconds the cortex is penetrated and the spinal probe plunges through the cortical wall bringing all the force back to zero as the surgeon no longer pushes on the awl.

Figure 10:
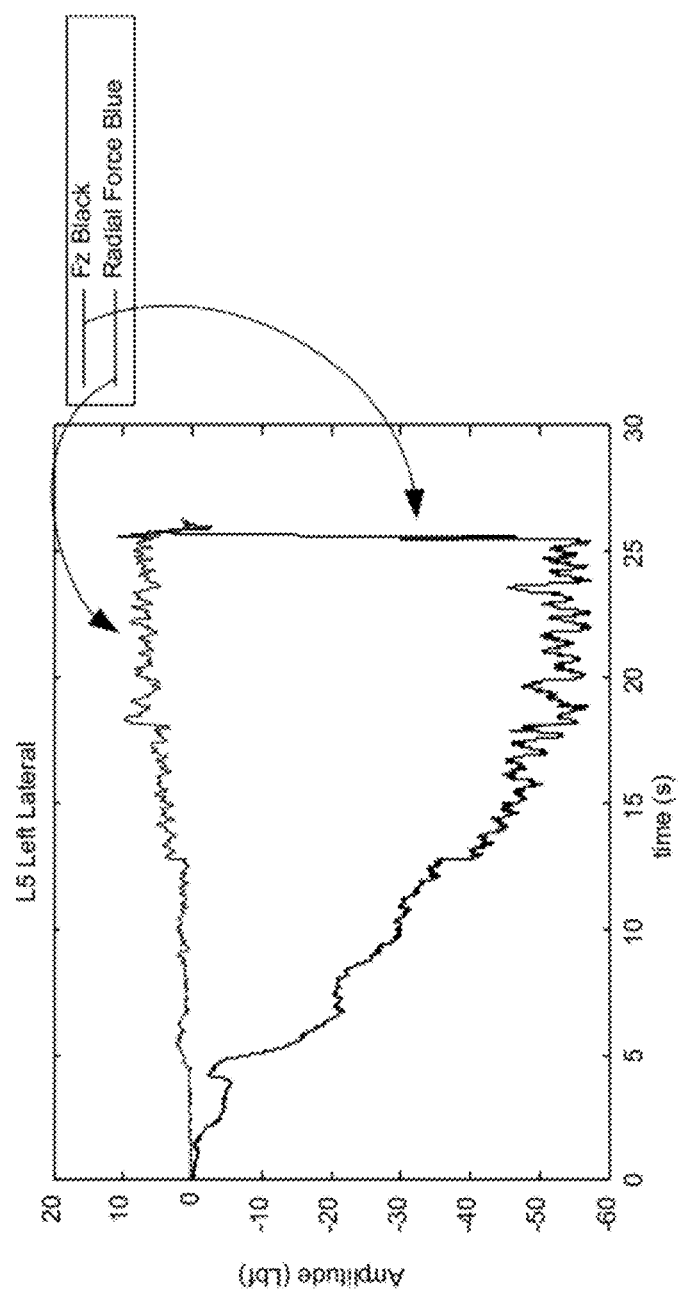
FIG. 10: Radial force profile of lateral breach in the left pedicle of L5.

Region two indicates that a breach can be predicted based on the force characteristics present while performing the pedicle tract procedure. From a mechanical force standpoint, any obstruction will provide a radial shear force at the tip of the spinal probe. While these forces will have an axial component in the z direction, there will also always be normal component in the radial sense. The axial force is equivalent to forces in the z direction while the radial force is the magnitude of $F_X$ and $F_Y$. FIG. 10 shows this increase in radial force.

FIG. 10 is a plot of the resulting radial force and axial force, $F_Z$, that were acquired during the experiment. As the tip of the spinal probe comes into contact with the cortex, the axial forces become relatively steady. Meanwhile, the radial forces increase substantially due to the shear forces inflicted on the tip by the cortex. Finally, the cortex is breached and the forces return to zero. Therefore, this increase in radial force could serve as an indication to surgeons as to whether or not the pedicle is going to be breached.

Figure 11:
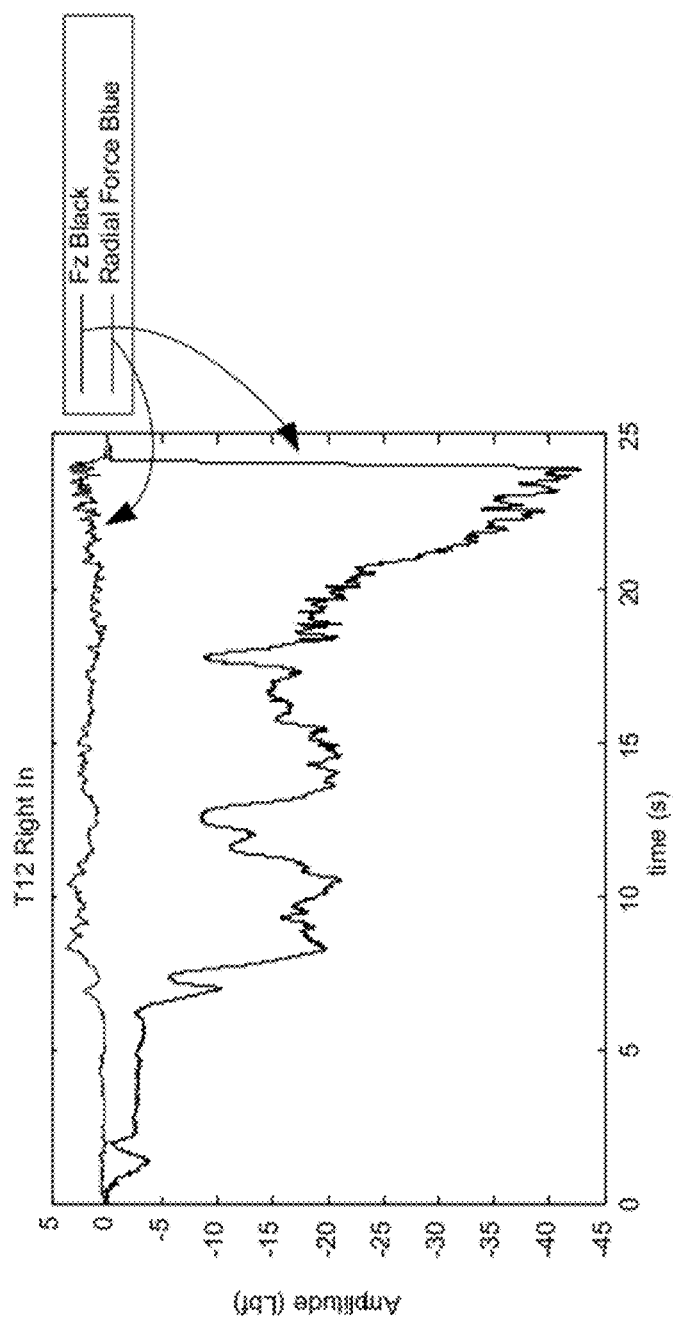
FIG. 11: Force profile of intact trajectory of the right pedicle of T12.

In comparison, an intact profile in FIG. 11 does not contain the same type of force characteristics. Instead of an increasing radial force as seen in FIG. 11, there is a more consistent value.

The profile in FIG. 11 does not contain the same characteristics as those seen in the lateral breach of the right pedicle of L5. Here, the radial force has a small increase around time t=5 seconds and then stays relatively constant throughout the plot until time t=20 seconds. At this point the force in z makes quick descent which is due to the increasing diameter of the spinal probe's taper.

Additionally, the resulting radial force in FIG. 11 is much smaller in magnitude than that of the lateral breach in L5. The increase in radial force can be caused by shear forces inflicted on the handle of the spinal probe by the surgeon.

In some cases there may be a radial component of the force in an intact trajectory due to from a variety of variables. These radial forces could be coming from the shaft of the spinal probe bumping up against the cortex or from shear forces inflicted by the surgeon on the handle of the spinal probe.

Figure 12:
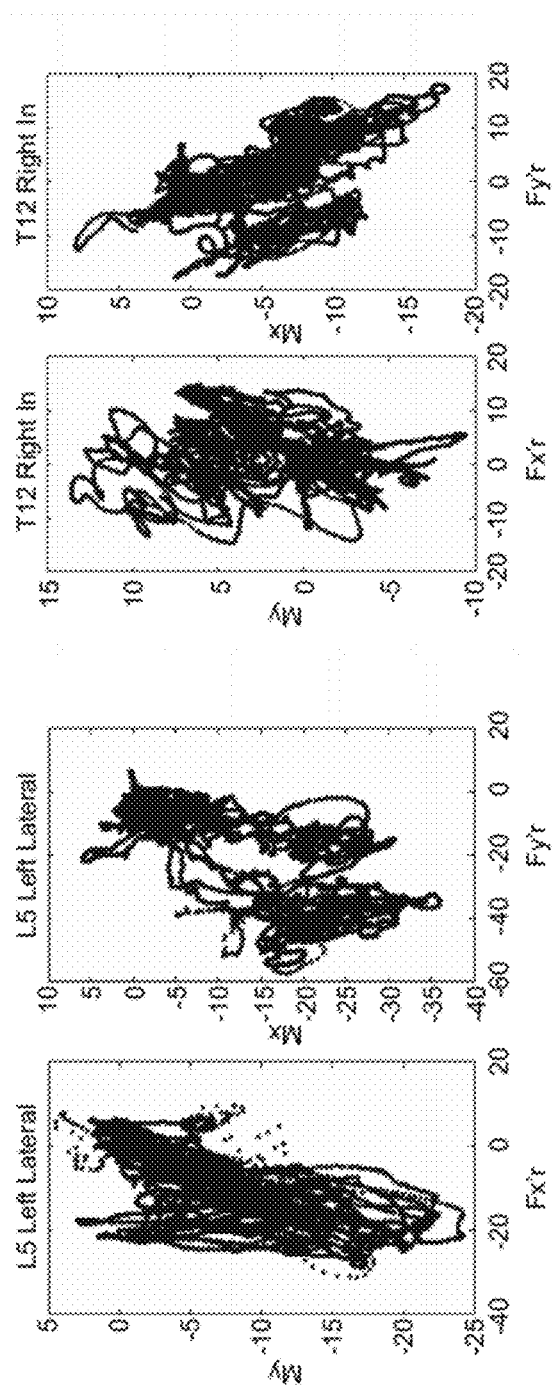
FIG. 12: Moments in x and y plotted as a function of the corresponding cross-product.

In order to check whether or not the radial forces are due to shear forces at the tip, the moments about x and y were plotted against their corresponding forces scaled by the distance to the tip of the spinal probe. If all the radial forces are the result of shear at the tip of the spinal probe, the relationship between the moment and its corresponding cross-product should be linear with a strong correlation. The results can be seen in FIG. 12.

The correlation of the moments in the lateral breach proved to have a strong linear association. For the lateral breach, the moment about y ($M_Y$) and its corresponding cross-product, $r \times F_X$, had a correlation value of 0.7708 while the moment about x ($M_X$) and its corresponding cross-product, $r \times F_Y$, had a correlation value of 0.800. Meanwhile for the intact data, $M_Y$ and its corresponding cross-product, $r \times F_X$, had a correlation of 0.2525 while $M_X$ and its corresponding cross-product, $r \times F_Y$, had a correlation of −0.5711. Since the correlation is substantially strong for the breach sample, it is safe to assume that the increase in radial force was due to the tip of the smart probe coming into contact with the cortex of the pedicle. Furthermore, the poor correlation seen in the intact data leads one to assume that the radial forces most likely have come from the shaft of the smart probe coming into contact with the cortex or external forces inflicted by the user along the handle.

The largest amount of radial force came from the lateral breach of the right pedicle in L5, with a mean radial force of 4.04 lbf and a standard deviation of 2.50 lbf. Conversely, the lowest mean radial force came from the intact placement in the right pedicle of T12, with a mean radial force of 1.61 lbf and a standard deviation of 0.71 lbf. Additionally, the larges axial force was in the medial breach of the right pedicle of L1, with a mean axial force of −44.10 lbf and a standard deviation of 4.65 lbf. Conversely, the smallest axial force came from the intact placement of the left pedicle of L1, with a mean axial force of −29.98 lbf and a standard deviation of 16.86 lbf.

Based on the results of the cadaver study, it was clear that when the tip of the spinal probe comes into contact with a boundary, there is an increase in radial force. Furthermore, an increase in radial force may be capable as serving as an indication of whether or not the tip of spinal probe is about to breach the pedicle.

Experiments were also run using laboratory samples including foam, foam and clay, cardboard and clay, and cork and clay. The goal of these different samples was to provide enough evidence that the specific force characteristics at a boundary could be confirmed. From the results of these three tests, it was accepted that at a boundary, no matter how distinct, there will be an in increase in the radial force do to the shear force inflicted by the boundary on the tip of the spinal probe. An apparatus that could measure force as a function of distance was constructed in order to establish the driving physics when the spinal probe came into contact with a boundary.

Figure 26:
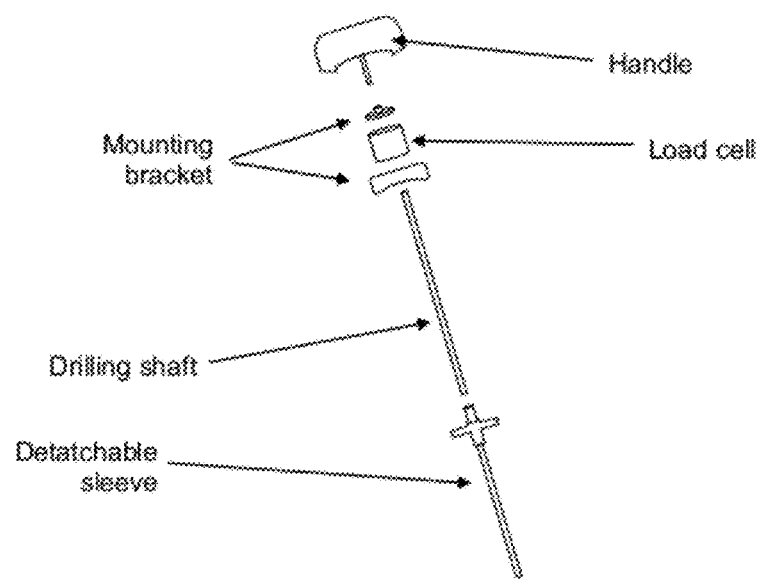
FIG. 26: A fourth example embodiment of a spinal probe.

Experiments were run that limited the degrees of freedom of the probe to only one direction, thus allowing the spinal probe to penetrate the sample so that no external forces on the shaft of the spinal probe would be collected by the load cell. Having recorded the distance to the boundary before conducting the test, the boundary conditions described above were confirmed and compared against samples where no boundary was present. FIG. 26 shows the radial and axial forces at the known boundary along side of a trial with no boundary.

Figure 13:
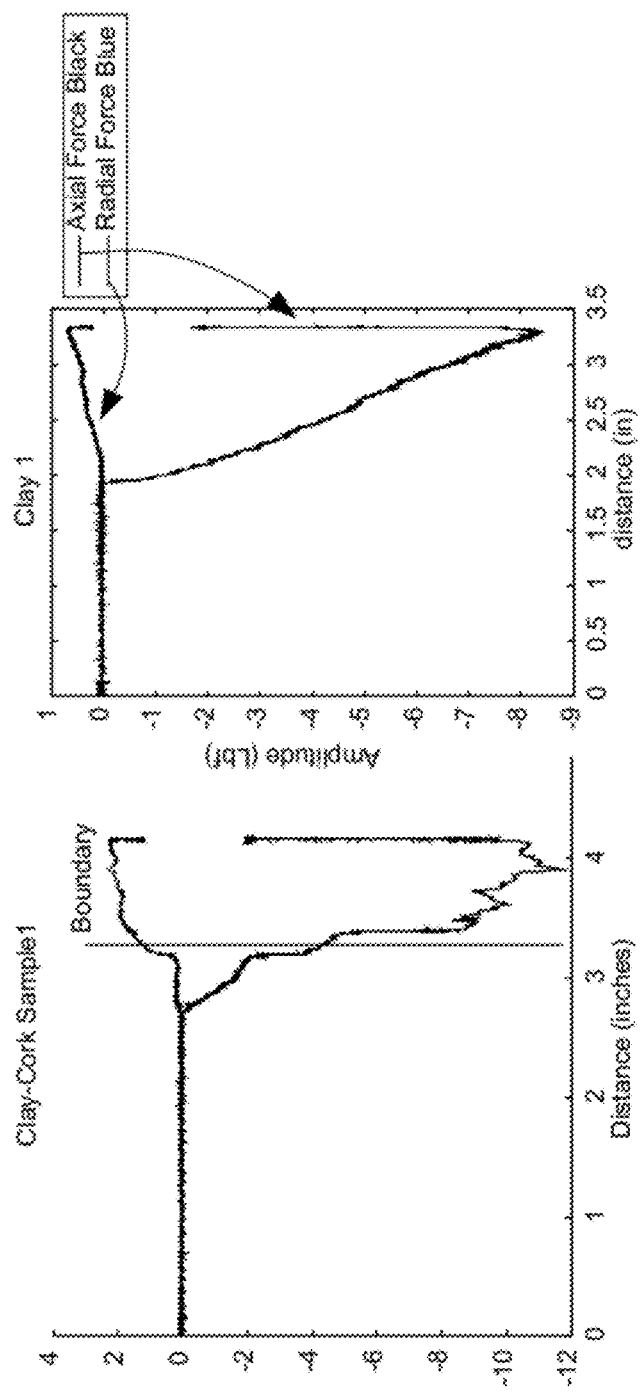
FIG. 13: Radial and axial force profile at known boundary (left). Radial and axial force profile without a boundary (right).

FIG. 13 shows that there was a large increase in the magnitude of both the radial and axial forces at the boundary. In contrast, there was a relatively small radial force component in the samples without the boundary. Therefore, this increase verified that when the tip of the spinal probe comes into contact with a boundary, there is an increase in radial force.

A correlation test, similar to that in the cadaver study, confirmed that the assumption regarding the increase in radial forces at the tip of the spinal probe were due to the presence of a boundary. This conclusion was based on the strong linear trend of the data.

To further illustrate the differences between sample containing a boundary and those that did not, a distribution of the radial forces for each trial was calculated. From the distribution, it was concluded that the distribution of the samples containing the boundary had a much larger variation in radial force than those samples that did not contain the boundary. In fact, the mean radial force for no boundary samples (clay only) was 0.6726 lbf with a standard deviation of 0.1183 while the mean radial force for boundary samples (clay-cork) was 1.5519 lbf with a standard deviation of 0.3249.

With the distribution of the data established, a one-way analysis of variance (ANOVA) test was conducted in order to determine if there was in fact a statistical difference between the mean of a no breach sample and the mean of a breach sample. For this statistical test, the null hypothesis was that the mean radial force of the two samples was the same. In contrast, the alternative hypothesis was that there was a difference between the radial force of the two sample means.

Figure 14:
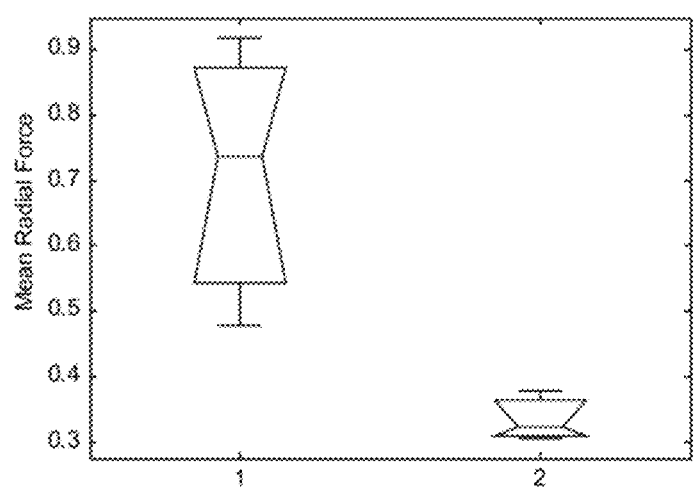
FIG. 14: Result of one-way analysis of variance. Sample mean radial force for breach on left (1) and no breach on right (2).

Using MATLAB, a one-way ANOVA test concluded that the probability of the null hypothesis being true was 0.044. In other words, the means will be the same only 4.4% of the time, which is sufficient enough evidence to conclude that the two samples were statistically different. The results of the ANOVA can be seen in FIG. 14.

The ANOVA test concluded that the likelihood of a boundary sample having the same mean radial force as a sample without a boundary was 4.4%. Based on these statistical differences and confirmation that the only radial forces present were those at the tip, a failure criterion was established to predict whether or not the spinal probe was about to breach the cork boundary.

The criterion was based on a 95% confidence interval established by the mean from the no breach samples. As long as the radial force was within 95% of the no breach mean, the spinal probe can continue on its current trajectory. However, once the radial force exceeded the 95% confidence interval of the no breach mean, the spinal probe must be redirected. Therefore the 95% confidence interval serves as a warning level for a breach.

In order to test the efficacy of the 95% criterion, it was applied on a clay-cork samples and a clay only samples. The results applied to clay-cork sample 1 and clay only sample 1 can be seen in FIG. 15.

Figure 15:
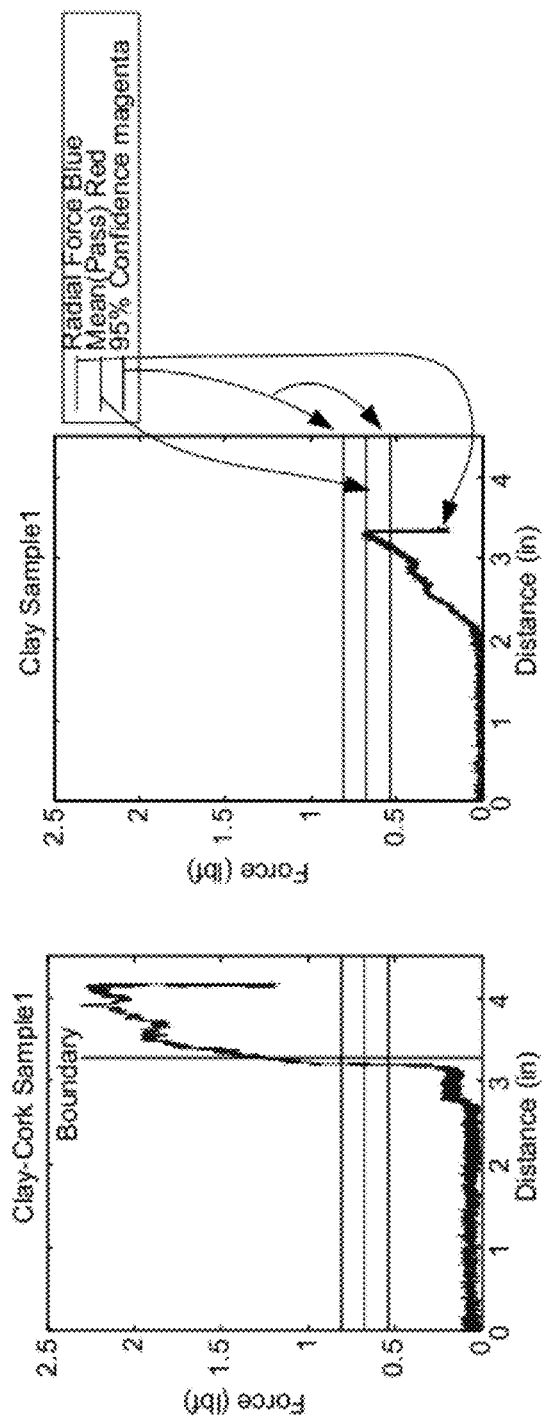
FIG. 15: Prediction criterion based on 95% of no breach mean radial force applied to a boundary sample (left) and a no boundary sample (right). Radial Force=Blue. No Boundary Radial Force Mean=Red. 95% Interval=Magenta. Boundary=Green.

Since the boundary was penetrated after the radial force exceeded the 95% confidence band as shown in the figure on the left of FIG. 15, it was concluded that the 95% confidence interval was sufficient in predicting breaches in samples where a boundary was present.

The results indicating a statistical difference between mean radial force of the clay-cork samples and the clay samples as well as the success of prediction criteria, it was concluded that a prediction method could be established based on the an increase in radial force. Although the clay and cork provided a useful demonstration, they were not a true representation of bone. However, applying the lessons learned from the clay-cork experiments to bone would establish a useful method for predicting pedicle breaches based on the increase in radial force.

With the profile characterized, the spinal probe was then used in a study involving eight postmortem pig spines. Varying trajectories were performed in order to differentiate between a successful and an unsuccessful pedicle tract profile. The data from the pig study was also used to test the prediction method set by the clay and cork study.

Figure 16:
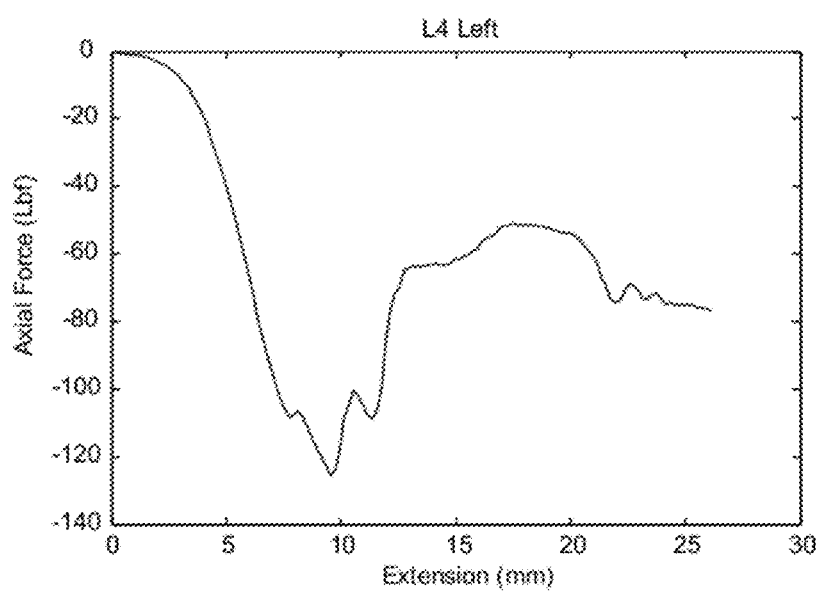
FIG. 16: Axial force profile of plunging into the spine with no twisting and cortex intact.

Before developing a predictive method, a pig spine was tested on an Instron in order to characterize the forces necessary for plunging into the spine. The Instron machine measured axial forces corresponding to an input velocity. For this test, the Instron measured axial forces as the spinal probe penetrated the spine at 2 mm/s. FIG. 16 shows axial force profile of plunging into the spine with no twisting and cortex intact.

The axial force profile exemplifies the mechanical strength of the cortex in the spine. At a peak value of −130 lbf needed to penetrate the cortex, there is clearly a distinct difference between density of the cortical bone and the cancellous bone. In fact, other samples ranged from −50 lbf to −200 lbf. Furthermore, this region explains the mechanical advantage in twisting the awl while performing the pedicle tract procedure.

Furthermore, the axial force profile exemplifies the shear forces caused by the taper in the awl. These shear forces resist the advancement of the spinal probe as it plunges into the pedicle. In this study, the resistance forces ranged from −70 lbf to −100 lbf. This revealed important characteristics of the bone in the pedicle. First, it showed surprising strength of cortex and the range of forces needed for penetration. Second, it validated the need for twisting and provided insight to the mechanical advantage of twisting while probing the pedicle. Third, it characterized the effect of the taper on the shaft of the pedicle awl.

The cadaver study indicated that as the spinal probe comes into contact with the pedicle wall, there is an increase in the radial force due to shear forces. This scenario was then simulated in the laboratory with samples of varying density. The laboratory samples confirmed the increase in radial forces. Finally, using clay and cork and measuring the distance as the spinal probe approaches the boundary proved that that at a boundary, there was an increase in the radial forces. The next step was to test the spinal probe in bone for a second time.

The goal of the pig study was to determine whether or not there was a difference in the radial force profile of a successful pedicle tract procedure and an unsuccessful one. In order to distinguish this difference, a mean of the radial force for each trial was recorded and used as a metric of statistical comparison. Furthermore, if there was a statistical difference, a second objective was to develop a predictive method that would indicate whether or not the surgeon was on a trajectory that would yield a breach of the pedicle.

Eight postmortem lumbar porcine spines were donated by the University of Minnesota Visual Heart Lab. These eight spines were cleaned of all soft tissue and frozen until the day of testing. Each lumbar spine contains five vertebral levels, with each level having two pedicles. Therefore, five spines provided 80 samples to compare.

The experiment was designed in order that the trajectory was randomized per vertebral level. This was done to eliminate the anatomical differences of each vertebral level. The test consisted of 75 plunges, with 25 intact trajectories, 25 lateral breach trajectories, and 25 medial breach trajectories. The goal was to distinguish the difference between a breached pedicle and an intact pedicle. The trajectory was randomized according to the vertebral level and was applied to both the left and right pedicle of the corresponding vertebra. Additionally, the trajectory of each trial was checked with a postoperative CT scan. If a trajectory did not follow the intended path, the sample was removed from the study. For example, an intact trajectory that ended up breaching laterally was removed.

Figure 17:
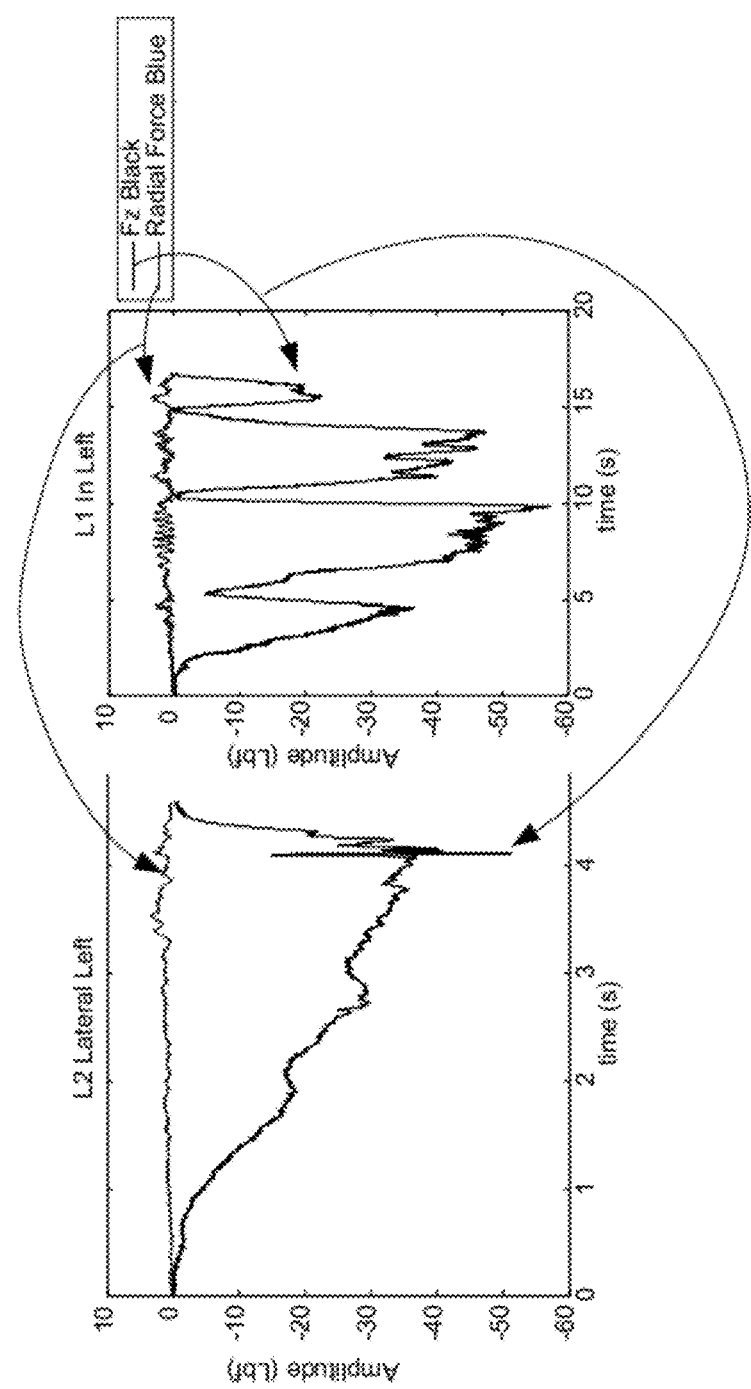
FIG. 17: Force profile corresponding to a lateral breach trajectory of the left pedicle in L2, spine 2 (left). Notice the large spike in FZ indicating a breach. Force profile corresponding to intact trajectory of the left pedicle in L1, spine 5

FIG. 17 provides and compares the profiles of a breached trajectory to an intact trajectory. The figure on the left is a force profile of a lateral breach in the left pedicle of L2 of spine 2, while the right figure is the intact force profile for the left pedicle of L1 of spine 5.

In the lateral breach, just as in the cadaver studies, there is an increase in the axial force and a relatively flat radial force until the tip of the spinal probe comes into contact with the cortex. This region corresponds to time t=0 to t=3 seconds. At time t=3 to t=4 seconds there is a growth in the radial force, indicating the tip of the spinal probe is experiencing a shear force imparted by the cortex. Finally, at time t=4 seconds the cortex gives way to the tip of the spinal probe, as indicated by the spike in FZ.

In comparison, consider an intact force profile on the right. A surprising result of the intact trials, exemplified in this sample, is the large amount of radial forces present during the intact probe placement. Regardless, the statistics for each trial was calculated and a predictive method was developed.

Before the prediction model could be established, the statistical parameters were calculated. The mean of the radial force for the medial breach samples was found to be 1.05 lbf with a standard deviation of 0.149 lbf, the mean radial force for the lateral force samples was found to be 1.28 lbf with a standard deviation of 0.188 lbf, and the mean radial force for the intact samples was 1.25 lbf with a standard deviation of 0.199 lbf.

Figure 18:
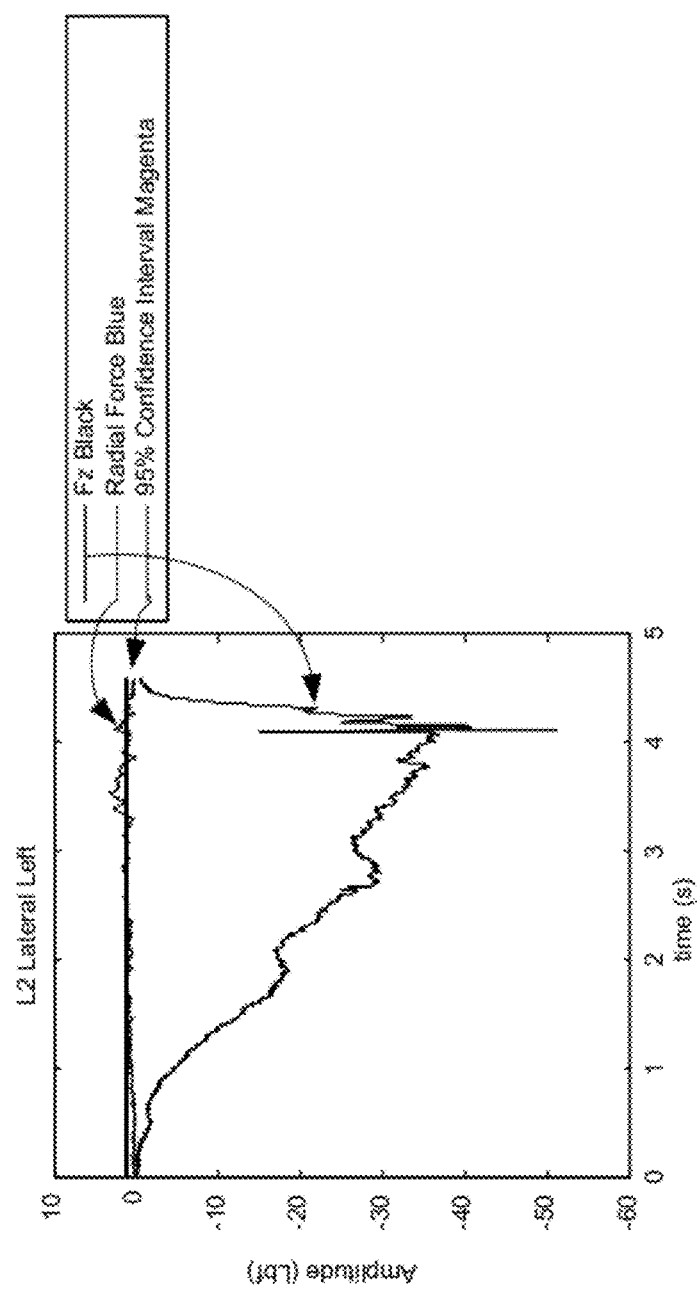
FIG. 18: 95% prediction method applied to a lateral breach of the left pedicle of L2, spine 2.

With the calculated statistics, a predictive method was developed based on the 95% confidence interval for the pig samples, identical to the approach taken with the clay-cork samples. Applying these criteria to the lateral breach trajectory of the left pedicle of L2 of spine 2, the breach is predicted. FIG. 18 shows the 95% prediction method applied to a lateral breach of the left pedicle of L2, spine 2. Although, the above was successful in predicting the lateral breach, the method was not free from false negatives.

Figure 19:
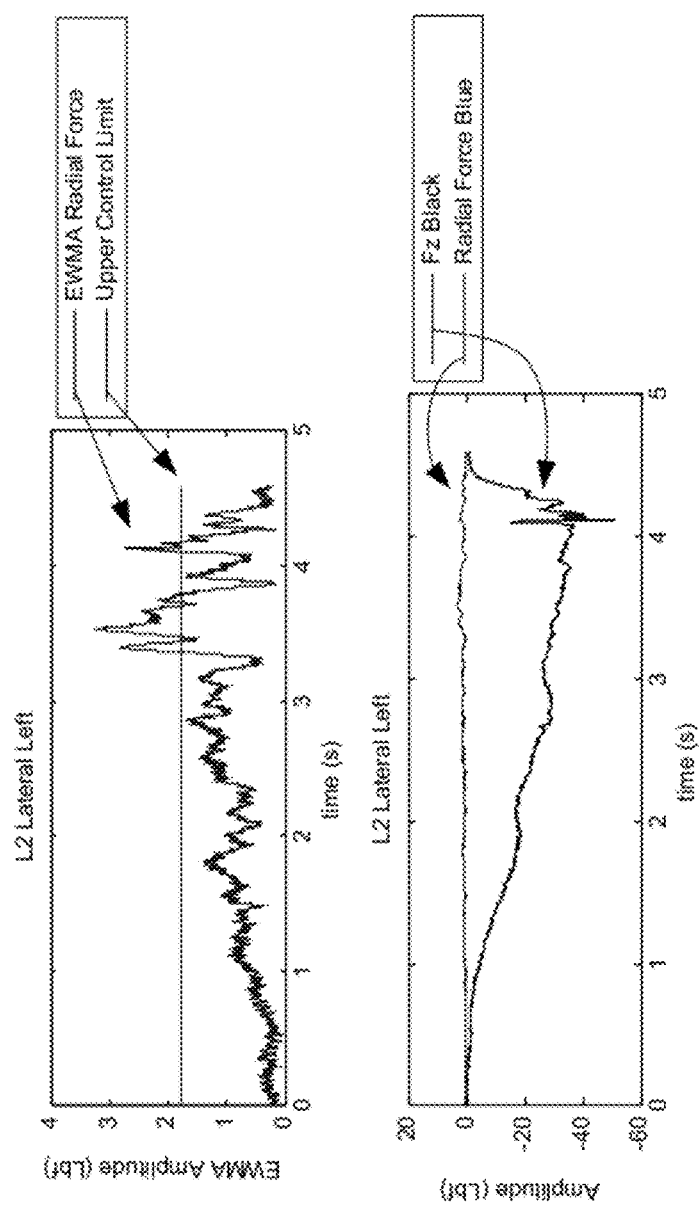
FIG. 19: EWMA control chart of radial force and control limit (top). Corresponding force profile (bottom) for the lateral breach of the left pedicle of L2, spine 2.

A second predictive model was developed based on control chart statistics. Instead of relying on a sample mean, the control chart based predictive method predicted a breach based on incoming data. Unlike the 95% criterion method, which relies on a sample mean and does not account for differences between specimens nor vertebral level, a control chart calibrates itself upon runtime and is unique to each pedicle. FIG. 19 shows the EWMA control chart of radial force and control limit (top) and a corresponding force profile (bottom) for the lateral breach of the left pedicle of L2, spine 2. In the EWMA method, if the radial force data exceeds the red control limit, the surgeon should alter the spinal probe's trajectory. Any radial force above the upper control limit risks the chance of breach.

Figure 20:
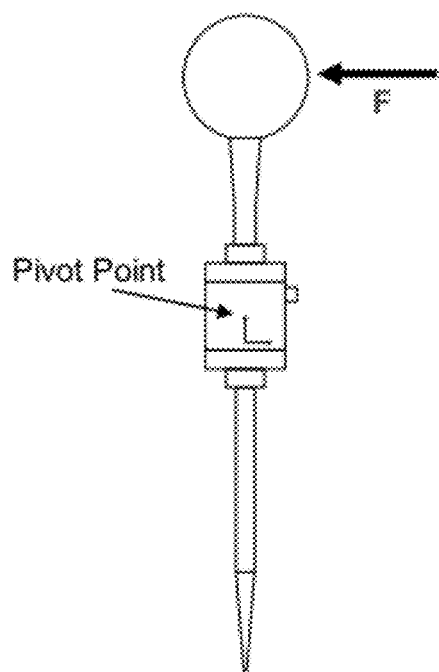
FIG. 20: Forces at handle of the probe.

For the first embodiment of the spinal probe, a pivot point of the moment arm is near the center of the spinal probe, as shown in FIG. 20. In some cases, external forces at the handle of the probe also are in the form of shear and therefore register on the load cell as a radial force, which may interfere with the ability to always distinguish from the shear forces at the tip of the spinal probe. In fact, the largest values of radial force were present at the end of the procedure. This most likely was the result of the surgeon accidentally introducing shear into the handle when the forces due to the taper in the spinal probe dominate the entry.

The correlation between $M_Y(r \times F_X)$ and $M_X(r \times F_Y)$ can confirm whether or not the shear forces where coming from the tip or the handle. The corresponding correlations of L3 are $M_Y(r \times F_X) = -0.2987$ and $M_X(r \times F_Y) = 0.4590$. These weak correlations indicate that the radial forces were not only due shear at the tip but also shear induced into the handle.

The cadaver study provided valuable information regarding the force profile using the spinal probe. First, the force profile revealed a range of forces seen in a typical pedicle tract procedure. From this study, the largest amount of radial force came from the lateral breach of the right pedicle in L5, with a mean radial force of 4.04 lbf and a standard deviation of 2.50 lbf. Conversely, the lowest mean radial force came from the intact placement in the right pedicle of T12, with a mean radial force of 1.61 lbf and a standard deviation of 0.71 lbf. Additionally, the largest axial force was in the medial breach of the right pedicle of L1, with a mean axial force of −44.10 lbf and a standard deviation of 4.65 lbf. Conversely, the smallest axial force came from the intact placement of the left pedicle of L1, with a mean axial force of −29.98 lbf and a standard deviation of 16.86 lbf. To date, the forces in the pedicle tract procedure have never been quantified and this data is a first step in fully quantifying the procedure. Further trials using probes such as the spinal probe will describe what is currently an art developed by surgeons over decades of practice, into a qualified metric.

Second, the profile showed distinctive characteristics of breached pedicle when compared to an intact pedicle. These distinctions where shown in both a radial force and an axial force. The radial force component associated with a breach was defined by a substantial increase preceding the breach. The axial component associated with a breach was defined by a large spike in the axial data.

Finally, the profile revealed that it may be possible to predict a pedicle breach based on these force measurements. This was indicated in the cadaver study where the radial forces increased in magnitude preceding a breach. However, in order to have a radial force free of skewed radial forces from regions of the spinal probe aside from the tip, the probe must enter the bone in as straight as a trajectory as possible.

In order to check this requirement correlation values were calculated relating moments to their corresponding cross-products. In the cadaver study, the correlations were relatively strong with the lowest correlations coming from intact trajectories.

Laboratory samples served the purpose of providing cheap alternatives to bone samples and provided confirmation to the trends postulated from the cadaver study. Furthermore, using force as a function of distance, the driving physics of the probe where quantified. Laboratory models indicated that there was a statistical difference between mean radial force of the samples containing boundaries and samples were no boundary was present (p=0.044). From this statistical understanding, it was concluded that a prediction method could be established based on the increase in radial force when the tip comes into contact with a boundary.

The initial prediction developed for the laboratory models was based on a 95% confidence interval set by the mean radial force of the no breach samples. In order to bring together the findings of the cadaver study and the findings of the laboratory models, an experiment involving eight lumbar pig spines was conducted. To account for variability in pig spines, a prediction model was developed based on an estimated weighted moving average. The EWMA criterion was a more robust method of prediction in that it calibrated itself during each trial, accounting for both intra and inter variability in samples.

Alternative Embodiments

Figure 21:
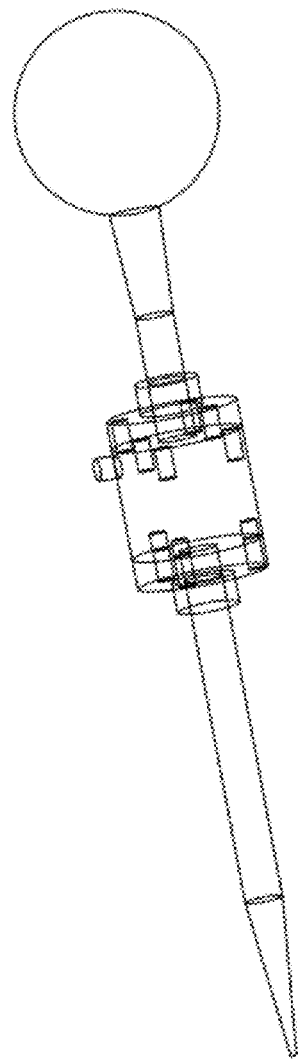
FIG. 21: Sketch representation of the example spinal probe.

The first embodiment of the spinal probe quantified the pedicle tract procedure in several ways. First, it gave a range of forces the surgeon must use in order to advance the awl into the pedicle. The probe also showed that the forces are in the form of axial forces along the shaft of the probe which increase as the awl shaft increases in diameter along the taper of the probe. Second, the spinal probe indicated that there is a radial force component whenever the probe comes into contact with the cortex of the pedicle. This radial component was due to shear forces inflicted by the wall on the tip of the probe. Finally, using laboratory models, the spinal probe was able to detect whether or not a breach was likely to occur based on these radial shear forces. FIG. 21 is a schematic sketch of the first embodiment of the spinal probe.

In first embodiment of the spinal probe, a radial force inflicted by the surgeon on the handle of the probe registers as a radial force on the load cell. Therefore, the magnitude of the radial force would be a component of both the forces at the tip as well as the forces at the handle.

Figure 22:
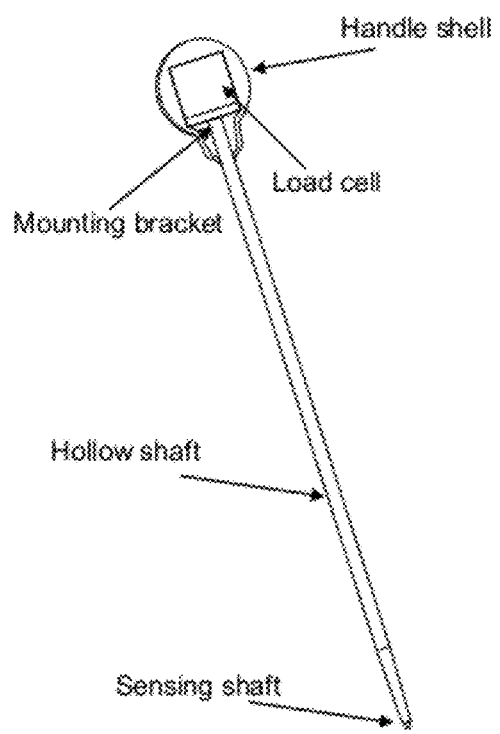
FIG. 22: A second example embodiment of a spinal probe.
Figure 23:
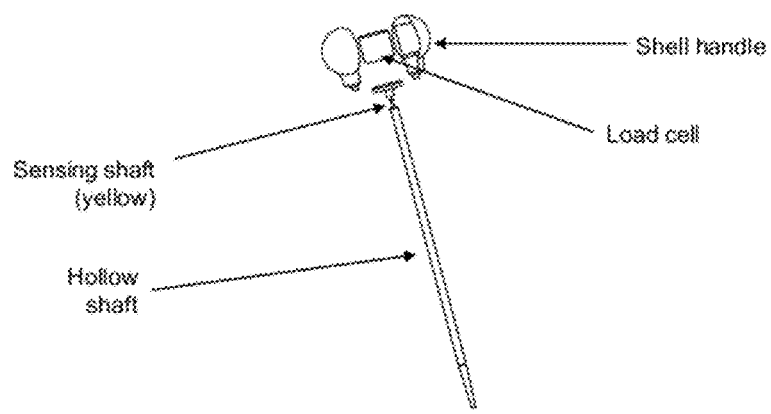
FIG. 23: An exploded view of the second example embodiment of the spinal probe.
Figure 24:
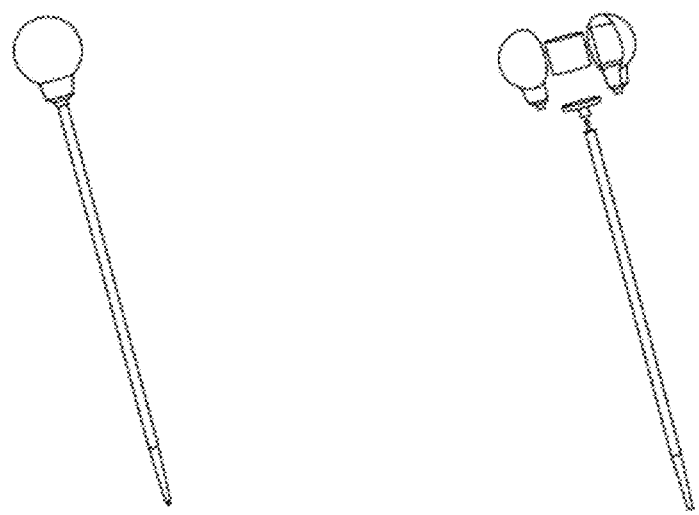
FIG. 24: Assembled second embodiment spinal probe (right) and exploded view (left).
Figure 25:
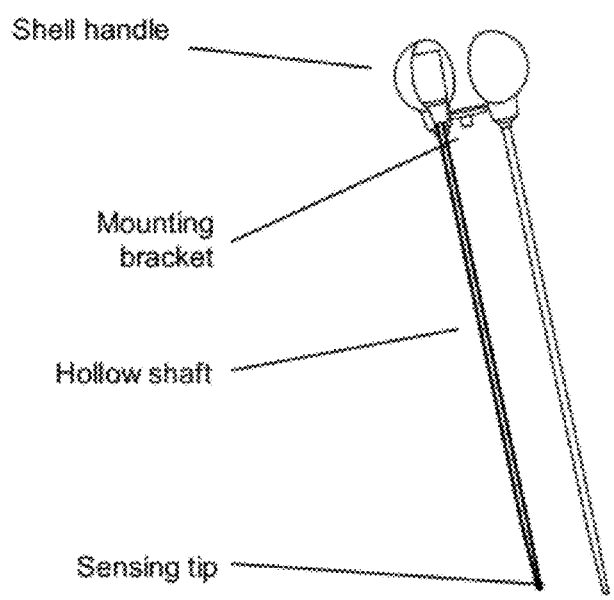
FIG. 25: A third example embodiment of a spinal probe.

FIGS. 22 and 23 show a second embodiment of the spinal probe is designed such that only forces at the tip are the only forces sensed by the load cell. A design such as this requires that all forces at the handle as well as along of the shaft of the awl must not be sensed by the load cell. In the second example embodiment of the spinal probe, the load cell is embedded in the handle of the awl instead of axially mounted along the shaft. Embedding the load cell within the handle eliminates or substantially reduces the shear forces skewing the radial force measurements. Additionally, instead of attaching the shaft of the probe to the load cell in order to measure both the radial and axial forces, the second example embodiment of the spinal probe uses a sensing shaft. This sensing shaft may be small in diameter and mounted to the load cell using a mounting bracket just as in the first example embodiment. The sensing tip may be enclosed by shell ensuring that any forces along the shaft of the probe do not also skew the radial data. FIG. 24 shows an assembled second embodiment of the smart probe (right) and exploded view (left).

As with the first embodiment of the spinal probe, the handle may be made from molded plastic. Similarly the mounting bracket may be machined from aluminum and the shaft of the probe would be hardened steel or titanium. Since the sensing shaft may be a cylindrical shaft encompassing the entire length of the probe, the cylinder may be made of a very stiff material to ensure that and deflection of the tip is translated to the load cell. A carbon fiber shaft with a steel or titanium tip, for example, provides strength needed at the tip as well as the stiffness required in the shaft.

A third embodiment of the spinal probe uses custom built strain gauges mounted on the tip of the sensing shaft instead of using the load cell. This removes the load cell and makes use of strain gauges mounted on a sensing tip. The sensing tip would be mounted within the shaft at the distal end of the probe. The shaft may be hollow allowing for wires carrying the strain gauge voltage to a microprocessor mounted on a printed circuit board within the handle shell. FIG. 15 is an example schematic diagram showing this third embodiment of the probe.

The possible advantage to using strain gauges is two fold. First, it does not require the use of an expensive load cell. In turn, this would eliminate the bulk of the probe and any unnecessary weight due to the load cell. Secondly, it does not require that the sensing shaft encompass the entire shaft length of the awl. Instead, the sensing shaft would only ascend the hollow shaft far enough that the strain gauges would be protected from any unwanted shear forces.

In conjunction with custom mounted strain gauges in the tip of the spinal probe, a wireless system could be included. This system would consist of a printed circuit board with a microcontroller capable of converting the analog signal changes in the strain gauges to a digital signal. The digital signal would then be transmitted to a near by receiver using a radio transmitter. The digital signal may be transmitted in accordance with 802.11, Bluetooth, or other RF protocol.

With a smart probe that is free of skewed radial force data in place, the prediction algorithm can be further developed. The predictive algorithm based on the 95% confidence interval could be further developed by collecting a database of varying bone diseases. This would include a sample mean for osteoporotic bone, scoliotic bone, and kypotic bone. The EWMA prediction model could be further enhanced by running a multivariate study to find the ideal $\lambda$ and L values for the control calculations. Additionally, a third predictive model could be established based on the data represented in the $F_y(F_x)$ plot. This may be developed using both a 95% confidence interval as well as adapting a EWMA model.

Various embodiments of the invention have been described. These and other embodiments are within the scope of the following claims. For example, although described with respect to a pedical probe, in other embodiments the functions described herein may be incorporated within other instruments. FIG. 26 shows an embodiment in which the features may be implemented within a pedicle drill. The pedicle drill may include a drilling shaft with a locking sleeve. It is designed such that when the surgeon drills into the pedicle, a removable sleeve can remain in place. With the sleeve in place, the surgeon can check the trajectory with an imaging probe, e.g., a StealthSystem probe. The adapted probe consists of the same components as the original probe only instead a load cell is axially mounted on the top of the tool. The load cell may be mounted axially along the shaft of the probe such that the sleeve can be snapped into place via the bottom mounting bracket.

As another example, spinal surgery is not the only orthopedic surgery where complex anatomy makes it difficult to perform surgery. Like spinal surgery, other orthopedic disciplines that include bone fixation with screws have adapted the use of image-guidance visualization systems in order to more effectively perform surgery. Therefore, just like spinal surgery, the use of the spinal probe described herein including is tactile feedback and breach prediction would further enhance the surgeon's understanding of the procedure.

An additional use for the spinal probe would be to use the data as a training probe. Currently, residents train on test spines and eventually cadavers. However, most test specimens vary significantly from the true tactile feel of human bone and residents, therefore, do not develop the tactile sense necessary for spine surgery. Having a quantified display of the force could help resident surgeons to get a better understanding of the forces needed and the corresponding tactile feedback.

Further, building on the idea of using the device as part of a training simulator, one could use the probe to collect quantitative data for the future development of haptic probes. These haptic probes could be used for virtual simulation, eliminating the need for expensive cadavers.

Anatomy

The spine provides important support for the body. There are twenty-four segmented vertebrae in the spine, each connected with intervertebral discs. Connecting the skull to the pelvis through segmented vertebra, the spine is both strong and rigid while maintaining movement and flexibility.

The spine can be described as a mechanical structure consisting of complex levers (vertebrae), pivots (discs), passive restraints (ligaments), and activations (muscles). Its fundamental functions are to transfer the weight, to provide motion, and to protect the spinal cord. The spine transfers the weight of the head and trunk along with weight lifted from the pelvis. It provides motion between these regions as well. Most importantly, the spine protects the spinal cord from harmful forces or motions.

The spine has four distinct curves in the lateral plane. There are two curves convex anteriorly in the cervical and lumbar regions and convex posteriorly in the thoracic and sacral regions. These curves provide the spinal column with flexibility and the ability to absorb shock while maintaining the appropriate stiffness and stability.

The entire spine is broken up into five sections consisting of the cervical, thoracic, lumbar, sacrum, and coccyx regions. The coccyx begins the spine below the pelvis and it consists of four fused segments. Superior to the coccyx is the sacrum, which consist of five fused sacral vertebrae. The sacrum is wedged in between the pelvis and provides the base at which the lumber spine begins. The lumbar spine consists of five individual vertebrae. The sixth vertebra superior to the sacrum marks the start of the thoracic spine which consists of twelve individual vertebrae. The cervical spine begins at the eighteenth vertebra superior to the sacrum and consists of seven vertebrae. The cervical spine provides the connection to the skull.

Vertebra, whether cervical, thoracic, or lumber, have many shared features. The vertebral body accounts for the bulk of the spine, providing the majority of the support within the spine. The spinal cord travels down the vertebral foramen, which is encapsulated by the lamina and pedicle. In general, the vertebra may be viewed as consisting of two parts. The first part is the anterior block of bone known as the vertebral body. The second part is the bony posterior ring known as the neural arch. The neural arch contains the articular, transverse, and spinous processes.

The vertebral body is approximately cylindrical in shape with an outer, thin shell of cortical bone (cortex) with an interior cancellous bone core. The vertebral end-plates, both superior and inferior surfaces, are slightly concave.

The articular, transverse, and spinous process make up the neural arch. Two pedicles connect the neural arch to the vertebral body. The entire neural arch contains seven processes: two articular processes, two transverse process, two articular facets, and one spinous process.

The anatomical design of the vertebra is approximately the same from C2 to L5. The design differs in terms of size and mass, generally increasing from the first cervical to the last lumbar vertebra.

There are two types of bone within the vertebra. The dense, exterior bone is the cortical bone. The softer, interior bone is the cancellous bone. The two differ in the amount of spacing or porosity present between the layers of bone.

Cortical bone, sometimes referred to as compact bone, is the dense outer shell, in bone. The dense outer cortical shell is often referred to as the cortex. It accounts for approximately 80% of the bone in the human body. The main function of cortical bone is to provide support in the bone. It is extremely hard bone, formed from multiple layers of bone.

Cancellous bone, also known as trabecular bone, is a soft, spongy bone that fills the interior of the vertebra. It has a low density and low strength and provides flexibility between the bones. Cancellous bone has high surface area and functions as a protective layer for bone marrow. With its honeycomb shape, cancellous bone accounts for approximately 20% of bone within the body. The orientation of the cancellous bone honeycomb structure is inline with the principal directions of loading. Cancellous bone is also responsible for the production of red blood cells.

Pedicles are short, thick process connecting the neural arch to the vertebral body. They vary in size within each vertebral region of the spine as well as shape posteriorly to anteriorly. Just like all bone, pedicles consist of a cancellous core surrounded by a cortex. Pedicles play a critical role in spinal fusion as they provide a direct path from the posterior surface to the anterior surface of the vertebra. In other words, they provide the direct path from the side of the body most accessible to the spine to the bulk of the vertebra, the vertebral body. This pathway serves as the trajectory for pedicle screw fixation. The size of each pedicle is a function of its width, height, and length. Within the lumbar spine, the cross-sectional area of the pedicle generally increases as the vertebral level increase. The thoracic spine, on the other hand, does not generally increase with vertebral level but rather it decreases initially, then levels, and finally increases. This is due to the mechanical stability provided by the ribs cage in the thoracic region. The cervical pedicle cross-sectional area is much like thoracic pedicle in that it decreases initially, flattens, and then increases.

In order to get a complete understanding of the biomechanics of the pedicle, one must understand its three-dimensional anatomy. The most important anatomical features of the pedicle are the pedicle cross-section height (PDH), the pedicle cross-section width (PDW), the pedicle axis of inclination to the sagittal plane (PDIs), and the pedicle axis inclination to the transverse plane (PDIt). Other important features of the pedicle are the cortical shell thickness both superior and inferior (CTS and CTI respectively), cancellous core height (CCH), and cancellous core width (CCW).

Pedicle height (PDH) pertains to the length of the pedicle in the sagittal plane and is often referred to as the sagittal pedicle isthmus width. Within the thoracic spine, the pedicles are large relative to the sagittal height of the vertebrae.

Pedicle width (PDW) is one of the most important anatomic features that affect pedicle screw insertion. Wider pedicles enable the use of larger diameter pedicle screws.

Understanding the axis of the pedicle is also important. These axes are coronal pedicle axis, often referred to as the pedicle inclination in the transverse plane (PDIt), and the sagittal pedicle axis, often referred to as the pedicle inclination in the sagittal plane (PDIs). Both screw insertion and preferred starting point depend on these axes.

In general, the pedicle is an approximately tubular bone consisting of a cortical shell inclosing a trabecular matrix. In fact, it was once assumed that the pedicle was a simple, ovoid structure throughout the spine. However, it is now understood that the pedicle varies in shape from vertebra to vertebra. The thoracic pedicle can be viewed as a 3-dimensional structure that varies in shape from an upright or inverted teardrop to a kidney shape. Not only does the pedicle shape vary between each vertebra but it also varies in size posterior to anterior.

Within the pedicle, cancellous bone accounts for 61.3%-71.6% of the thoracic pedicle width. Additionally, throughout the thoracic pedicle, the medial pedicle wall is approximately 2-3 times thicker than the lateral pedicle wall. The pedicle is a complex, three-dimensional structure. It not only varies in shape posteriorly to anteriorly within the vertebra but also between vertebral levels. The pedicle contains a complex cortical wall with a cancellous core. Because the pedicle connects the posterior neural arch to the anterior vertebral body, it serves as the pathway for pedicle screw fixation in spinal reconstructive surgery.

Further details can be found in: S. Kuklo, and D. W. Polly, "Surgical Anatomy of the Thoracic Pedicle," *Seminars in Spine Surgery*, vol. 14, no. 1, pp 3-7, March 2002; A. White and M. Panjabi, "Physical Properties and Functional Biomechanics of the Spine," *Clinical Biomechanics of the Spine*, $2^{nd}$ Ed., $2^{nd}$ Ed., Philadelphia: Lippincott-Raven Publishers 1990. pp 512-610; S. Inceoglu, "Trabecular Architecture of the Lumbar Vertebral Pedicle," *Spine*, vol 30, no 13, pp 1485-1490, 2005; R. Lehman, T. Kuklo, and M. O'Brien, "Biomechanics of Thoracic Pedicle Screw Fixation. Part I: Screw Biomechanics," *Seminars in Spine Surgery*, vol. 14, no. 1, pp 8-15, March 2002; K. Ralph, "Internal Architecture of the Thoracic Pedicle: An Anatomic Study," *Spine*, vol 21, no 3, pp 264-270, February 1996; M. Panjabi, "Human Lumbar Vertebrae—Quantitative Three-Dimensional Anatomy," *Spine*, vol 17, no 3, pp 299-307, 1992; M. Panjabi, "Human Thoracic Vertebrae—Quantitative Three-Dimensional Anatomy," *Spine*, vol 16, no 8, pp 888-901, 199, M. Panjabi, "Human Cervical Vertebrae—Quantitative Three-Dimensional Anatomy," *Spine*, vol 16, no 8, pp 861-869, 1991; M. O'Brien, D. Smith, and T. Kuklo, "Biomechanics of Thoracic Fixation in Deformity. Part II: Hooks Versus Screws," *Seminars in Spine Surgery*, vol. 14, no. 1, pp 16-34, March 2002, the contents of each of which are incorporated herein by reference.

General Surgical Procedures of Pedicle Screws

Arthrodesis is a procedure in which a joint is fixed with the intention of fusing two bones together. Arthrodesis is often referred to as simply fusion, and when specifically dealing with the spine it is referred to as spinal fusion. Fusions are carried out for many reasons. First, it's used in order to support the spine when the spine's no longer structurally sound. Second, spinal fusion provides mechanical straightening in both scoliosis and kyphosis patients. It is also used in order to prevent scoliosis and kyphosis in susceptible patients. Third, spinal fusion is used to alleviate pain by reducing movement in certain regions of the spine.

In spinal fusion, vertebrae are joined together using external fixation. This is done in many ways but the most common method to date is using pedicle screws and longitudinal rods. An alternative to bracing the spine with pedicle screws and rods is to use bone grafts. Bone grafts provide stability between vertebra levels and are typically taken from the patient's pelvis. These are typically done when a disc is ruptured and stability needs to be replaced for one vertebra. Other methods include using hooks and longitudinal rods, wire and longitudinal bone, and screws and longitudinal plates.

The use of pedicle screws as the base in spinal fusion requires that the screw is drilled through the isthmus of the pedicle. Maximum screw purchase is accomplished with the screw embedded within the pedicle and vertebral body. Solid purchase in turn provides a solid foundation for the longitudinal rods.

In the thoracic spine, a safe and accurate placement of pedicle screws depends a thorough understanding of the pedicle's anatomic relationships and pedicle projection point. Additionally, the relationship between anatomic relationships of the pedicle and pedicle projection vary throughout the thoracic level and the insertion technique should change according to these variations. These generalizations can be applied to not just the thoracic region, but the entire spine. Understanding specific land marks, including the transverse process and facet joint, help the surgeon understand where to start with pedicle screw instrumentation.

A typical pedicle screw insertion process consists of locating the pedicle, hole preparation, and screw insertion. First, the pedicle is located using anatomical features and with a visualization system if available (typically fluoroscopy or CT). Once the pedicle is located, a pilot hole is prepared by predrilling a bone awl through the cortical bone. The bone awl travels through the pedicle and into the vertebral body, leaving behind a cavity used to properly guide the pedicle screw into the desired location. The pedicle screw is then inserted by hand and the results are confirmed using a CT or fluoroscope.

Ideally the pedicle screw travels through the pedicle and into the vertebral body without breaching out of the pedicle or the vertebral body. However, upon confirmation with a postoperative medical image, pedicle screws do not always travel the idealized trajectory.

In terms of the pedicle screw placement procedure, the cancellous bone provides very important tactile feedback to surgeons. Healthy cancellous bone provides resistance to the pedicle awl and allows surgeons to understand their location within the bone based on feel. The distinct difference in density between the cancellous bone and the cotrex is a key indication that the pedicle awl has deviated from the desired path. These distinct differences in densities result in a large range of forces applied by the surgeon in order to effectively place pedicles screws within the vertebra.

Longitudinal rods, pedicle screws, hooks, and transverse loading rods are basic components of the modern spinal fusion methods. Although the hook and rod expanded the surgeon's ability to correct spinal deformity, they fell short in many areas. Pedicle screws were first applied to the lumbar region and found to be a more desirable method of fixation. Surgeons later applied the methods used in the lumbar spine to the thoracic region. It has now been accepted that pedicle screw instrumentation is more successful at affixing the spine than hooks.

Hooks provided the initial means of fixing longitudinal rods to the spine. The hooks latched to the transverse process and were threaded or ratcheted into place. For a long time, hooks were believed to be the safest means of fixation in the thoracic spine.

Pedicle screws provide surgeons with more mechanical control than hooks. Drawbacks of pedicle screws include screw breakage, loosening, pullout, and migration. The important screw design characteristics pertaining to pedicle screw fixation include thread pitch, inner and outer diameters, and material composition.

Pedicle screws are typically made out of either stainless steel or titanium; however, titanium dominates the market due to its material properties. Titanium is closest to bone in its modulus of elasticity and it is more biologically accepted by the body. Additionally, titanium screws have been shown to have less scatter when used with CT imaging.

Pedicle thread pitch pertains to the number of threads present within the length of the screw. A screw with a smaller pitch would have more threads per unit length and a screw with a larger pitch would have less. Asnis el al showed, using a synthetic model, that a screw with decreased pitch had a higher pullout strength.

Screw diameter has two parts. The inner diameter pertains to the shaft diameter of the screw while the outer diameter is the thread diameter. Decoster et al showed that outer diameter plays the most important role in pullout strength of pedicle screws. Inner diameter may have some role osteoporotic bone but this has mixed results.

Pedicle screw shaft design pertains to the overall shape of the screw. Some screws have been designed as conical in shape while others are cylindrical.

Another important aspect of pedicle screws is the length of the screws and the corresponding depth of penetration. Krag et al reported that pedicle screws with 80% depth of penetration within the vertebral body had greater fixation strength than screws with a 50% depth of penetration within the vertebral body.

Before screws are anchored into the pedicle, the pedicle must be probed in order to form a pilot hole. This process is completed with a bone awl. There are many different types of bone awls on the market today. Varying from tip shape and shaft taper, each probe has a separate advantage and is preferred by different surgeons for different reasons.

The basic design of a bone awl is simple. There is a large handle for the surgeon to hold on to and use for manipulating the probe. From the handle protrudes a cylindrical shaft with a pointed tip which is used to navigate the pedicle. Probes differ in the size and shape of the tip, the shaft taper, and the length of the shaft.

Most awls used for creating the pilot hole for the pedicle screw are tapered by design. Tapers help to control the amount of plunge through the pedicle. The also are designed with varying tip sizes that allow the surgeon to have more tactile feedback throughout the pilot hole process.

Clinical Use of Pedicle Screws

Scoliosis is a disease were abnormal deformations in the vertebrae cause lateral deviations of the spine. From a biomechanical standpoint there is too much curvature in the frontal plane, too much vertical axis rotation in the wrong direction, and not enough curvature in the sagittal plane. The cause of scoliosis is generally unknown; however, it's believed to be caused by structural imbalance during periods of growth. On the other hand, elderly suffer from scoliosis as do adolescents.

Scoliosis is measured using the Cobb angle, which is the angle formed by the intersection of two perpendicular lines, parallel to the top and bottom vertebrae of the scoliotic spine.

Spinal fusion is recommended in scoliosis patients where the Cobb angle exceeds 40-45 degrees. The severity of the scoliosis determines the necessary number of fused vertebral levels. Curves between 60 and 100 degrees may cause a loss of pulmonary function, and in extreme angles, may cause respitory failure.

Segmental pedicle screws and longitudinal rods are the dominant fusion method for scoliosis. The use of pedicle screw based fusion has reduced the healing time from six to twelve month using hooks to two to four months screws.

Kyphosis is defined as an abnormally increased convexity in curvature of the thoracic spine. Patients suffering with kyphosis typically appear to be "hunchback." From a biomechanical standpoint, thoracic kyphosis is the result of a sagittal plane curvature with a posterior convexity that measures a Cobb angle great than 50 degrees. The cause of the disease could be from trauma, tumor, osteoporosis, or an abnormal developmental process. Pain is typically associated with Cobb angles greater than 50 degrees.

Although kyphosis cases of small Cobb angles may be corrected using an external brace, extreme cases require fusion. In these cases posterior fixation using pedicle screws and longitudinal rods are effective.

Osteoporsis is a disease, often found in postmenopausal women, where bone becomes abnormally weak. The cause of weakness is that osteoporatic bone typically lacks the normal levels of cancellous bone. Even when osteoporosis is not present, people over the age of 50 tend to have less a less complex "honeycomb" of cancellous bone. In ostoporosis, pedicle screws offer "an excellent means of fixation for patients who have osteoporosis as an underlying component of spinal disorder."

Spondylolisthesis is the anterior dislocation of a vertebra. This heretical disease is routinely treated with the use of pedicle screws and has shown up to 94% increase in bone union rate. Spinal osteotomy is a procedure where bone is removed in order to correct deformities. In these procedures, pedicle screws allow for short-segment fixation. The result is faster recovery time and more post-operative comfort.

Pedicle screws have also allowed surgeons to use short-segment instrumentation in spinal fractures and have resulted in union rates of 95% in lumbar degenerative disc disease. They have played unique, beneficial roles in spina bifida, neoplasms, and trauma in the cervicothoracic junction.

Further details can be found in S. Kuklo, and D. W. Polly, "Surgical Anatomy of the Thoracic Pedicle," *Seminars in Spine Surgery*, vol. 14, no. 1, pp 3-7, March 2002; P. Merloz, "Fluoroscopy-based Navigation System in Spine Surgery," *Journal of Engineering Medicine*, vol. 221, part H, pp 813-820; R. Gaines, "The Use of Pedicle-Screw Internal Fixation for the Operative Treatment of Spinal Disorders," *The Journal of Bone and Joint Surgery*, vol 82-A, no 10, pp 1458-1476, October 2000; A. White and M. Panjabi, "Biomechanical Considerations in the Surgical Management of the Spine," *Clinical Biomechanics of the Spine, $2^{nd}$ Ed.*, Philadelphia: Lippincott-Raven Publishers 1990. pp 512-610, R. Lehman, T. Kuklo, and M. O'Brien, "Biomechanics of Thoracic Pedicle Screw Fixation. Part I: Screw Biomechanics," *Seminars in Spine Surgery*, vol. 14, no. 1, pp 8-15, March 2002; Y. Rampersaud, "Image-Guided Accuracy Requirements," *Spine*, vol 26, no 4, pp 352-359, 2001; A. Youkilis, "Stereotactic Navigation for Placement of Pedicle Screws in the Thoracic Spine," *Neurosurgery*, vol 48, number 4, pp 771-778, April 2007; T. Maruyama, "Surgical Treatment of Scoliosis: A Review of Techniques Currently Applied," *Scoliosis*. vol 3, no 6, April 2008; J. Harrington, "Treatment of Scoliosis. Correction and Internal Fixation by Spine Instrumentation," *Journal of Bone and Joint Surgery*, vol 44, pp 591-610, 1962; Moore, McCabe, Craig. *Introduction to the Practice of Statistics*. 6th Ed. New York: W.H. Freemand and Company, 2009, pp 356-369, M. Panjabi and A. White, "Practical Biomechanics of Scoliosis and Kyphosis," *Clinical Biomechanics of the Spine*. 2nd Ed., Philadelphia: Lippincott-Raven Publishers 1990. pp 127-169, S. Ludwig, "Cervical Pedicle Screw—Comparative Accuracy of Two Insertion Techniques," *Spine*, vol 25, no 20, pp 2675-2681; the entire content of which is incorporated herein by reference.

The Predictive Algorithms

The predictive component of the design was prototyped using the mathematical software package, MATLAB. Two separate prediction models were established based on statistical models. The first model is based on a 95% confidence interval of the mean of successful pedicle tract procedures. The second is a control chart based approach using an exponentially weighted moving average to determine whether or not the spinal probe would breach the cortex. Both models converted the x and y force data collected by the load cell into a radial force. Similarly, both prediction models alerted the surgeon if the radial force exceeded a specific value.

The first predictive algorithm is based on the mean radial force of trials where there was no breach and therefore successful. This prediction method depends on a database of previous procedures in which the force data was collected. The mean radial force of past successful samples was used as a population mean with a corresponding standard deviation. This population mean and standard deviation were then used to calculate a 95% confidence interval of successful pedicle tract procedural radial force profiles.

The 95% confidence interval is based on the following equation,

Equation 1: 95% confidence interval of intact samples $$\mu_{in} \pm (1.96)\frac{\sigma_{in}}{\sqrt{n}}$$

$\mu_{in}$ is the population mean radial force of the successful trials, 1.96 corresponds to the 95% confidence z* statistic, $\sigma_{in}$ is the standard deviation of the clay only samples, and n is the number of samples.

As long as the radial force was within 95% of the successful population mean, the spinal probe can continue on its current trajectory. However, once the radial force exceeded the 95% confidence interval of the successful population mean, the spinal probe must be redirected. Therefore the 95% confidence interval serves as a warning level for a breach. Anything within the 95% confidence zone is considered potentially dangerous. This method was tested and proven effective in laboratory models.

The second method of predicting pedicle breaches based on the radial force data took advantage of the statistical models used in quality control. This method of prediction uses an exponentially weighted moving average (EWMA) of the radial force to determine whether or not the incoming radial force data is within control, or in other words, within an appropriate range. As soon as the radial force data becomes too great, or rather out of control, the algorithm predicts a breach.

The advantage to the EWMA prediction algorithm is that it is not based on past experiments like the 95% confidence interval. This eliminates any differences between vertebrae and different spines. Instead, the EWMA algorithm calculates its statistics within the initial plunge into the pedicle. In fact, this algorithm does nothing until the axial force exceeds −20 lbf. This axial force value was chosen based on experiments where bone was used as test specimens. All of the experiments had axial force data that well exceeded −20 lbf early in the pedicle tract procedure. Therefore, in order to get a better representation of the mean radial forces, an axial force of −20 lbf triggered the algorithm to begin collecting sample array for the next second. The mean of the one second array beyond −20 lbf defined $\mu_0$. A corresponding standard deviation $\sigma$ was also calculated from the array. These values were then used for determining the exponentially weighted moving average, its corresponding variance, and the upper and lower control limits.

The exponentially weighted moving average control chart is a method of detecting process control that relies heavily on past data points as well as the current ones. This is done by calculating the moving average of the data using the following equation:

$z_i = \lambda x_i + (1-\lambda)z_{i-1}$ Equation 2: Exponentially weighted moving average In Equation 2, $\lambda$ is a constant between 0 and 1, which is chosen based on the desired dependence on past data. The process target, $\mu_0$ and is based on the mean value of the radial force within the first second of the axial force exceeding −20 lbf. This is done in order to get a more accurate assessment of the radial forces in a patient specific manner based on the bone density for the particular patient, where the bone density is a primary factor that influences the variance of z, over time as the probe is inserted and contacts the bone. For the first EWMA value, $z_0 = \mu_0$.

The variance of $z_i$ over time is found using the following:

Equation 3: Variance of exponentially weighted moving average $$\sigma_{z_i}^2 = \sigma^2\left(\frac{\lambda}{2-\lambda}\right)[1-(1-\lambda)^{2i}]$$

Like all control charts, there are two control parameters; an upper and lower control limit which are often abbreviated as UCL and LCL respectively. If a process event exceeds the UCL or LCL, the process is referred to being out of control. Specifically corresponding to the pedicle tract procedure, an out of control radial force is an indication that a breach is likely to occur.

The UCL and LCL can be calculated in a patient-specific fashion according to Equation 4 and Equation 5.

$UCL = \mu_0 + L\sqrt{\sigma_{z_i}^2}$ Equation 4: Upper control limit (UCL) of the EWMA $LCL = \mu_0 - L\sqrt{\sigma_{z_i}^2}$ Equation 5: Lower control limit (LCL) of the EWMA In the EWMA prediction model, the UCL level is of most importance. Any incoming radial force data that exceeds this level has the risk of breaching the pedicle. On the other hand, the LCL serves as a warning.

Mechanical Forces Pertaining to Spinal Probe

Figure 27:
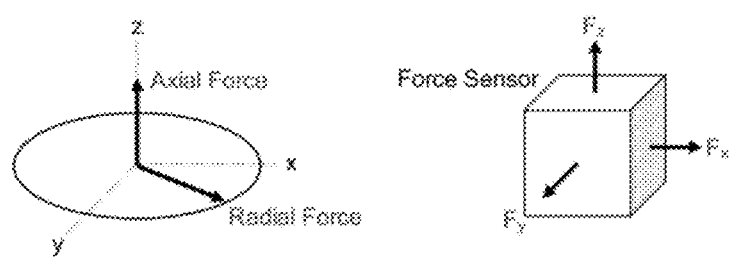
FIG. 27: Axial and radial forces (left) and corresponding rectangular coordinate force sensor (right).

Before discussing the forces specific to navigating the pedicle, a three dimensional coordinate system must be established. Both a rectangular and a radial coordinate system are used to describe the system and can be seen in FIG. 27, which shows axial and radial forces (left) and corresponding rectangular coordinate force sensor (right)

A radial coordinate system consists of an axial and radial force component. The axial component is the same as the force in the z direction in rectangular coordinates while the radial force is the resultant vector of the force in the x direction and the force in the y direction of rectangular coordinates. This relationship is shown in FIG. 28.

Figure 28:
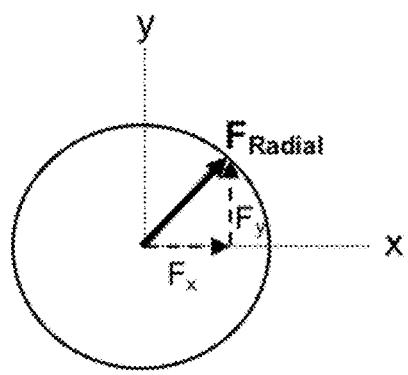
FIG. 28: Radial force definition.

As seen in FIG. 28, the radial force is the resulting vector of the force of x and the force of y. Mathematically this is represented as:

$$\vec{F}_{Radial} = \sqrt{\vec{F}_X^2 + \vec{F}_Y^2}$$ Equation 6: Radial force calculation Most force sensors measure forces in a rectangular coordinate system. Therefore, understanding the relationship between a radial force and its corresponding rectangular components is important in understanding the system. In terms of the force sensor, the axial forces will be in the form of $F_Z$ and the radial force, $F_R$, will be the resulting magnitude of $F_X$ and $F_Y$.

Some assumptions are made before describing the basic principles behind the design of the spinal probe. The first assumption is that the bone awl is a rigid member. A rigid member is defined as a body that does not deform while subjected to a load. The second assumption, building off the first, is that all of the shear forces sensed by the load cell in the x and y directions are due to forces at the tip of the probe. In other words, all radial forces are the result of the tip coming into contact with a boundary. Therefore, the second assumption ignores any radial force along the shaft of the probe as well as any shear induced by the handle of the probe.

Two basic principles of rigid members were used when designing a spinal probe capable of capturing the forces present during the pedicle screw placement procedure. The first was the principle of transmissibility. The second was the principle reactions of a fixed support.

Figure 29:
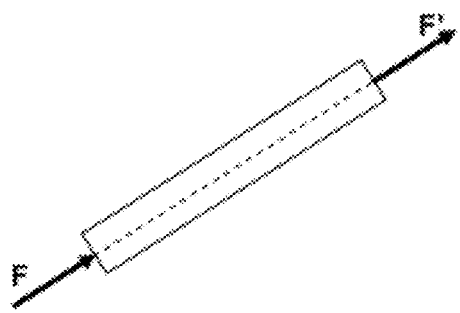
FIG. 29: Principle of Transmissibility: F=F'.

The principle of transmissibility can be described as the motion of a rigid body will remain unchanged if the force acting at a given point of the rigid body is replaced by a force of the same magnitude and same direction, but acting at a different point, provided that the two forces have the same line of action. FIG. 29 shows the Principle of Transmissibility: F=F'

Figure 30:
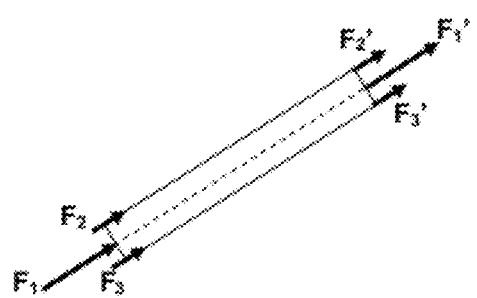
FIG. 30: Principle of Transmissibility in terms of shear/friction forces.

The principle of transmissibility plays an important role in the design of the spinal probe. Mentioned earlier, the pedicle tract procedure consists of the surgeon pre drilling a pathway for a pedicle screw using a pedicle awl. As the awl is driven into the pedicle, its movement is being inhibited by shear forces interacting between the bone and the shaft of the probe. These shear forces are in the form of friction. The principle of transmissibility states that all the shear forces caused by bone are equal anywhere along the line of action. FIG. 30 shows the Principle of Transmissibility in terms of shear/friction forces.

Figure 31:
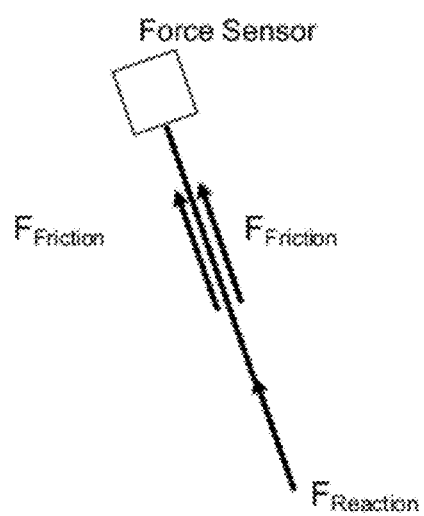
FIG. 31: Reaction and shear/friction forces captured by the sensor.

Therefore, by having a sensor mounted at one end of the rigid member, the frictional forces along the shaft of the spinal probe penetrating the bone can be translated to the force sensor. FIG. 31 shows the Reaction and shear/friction forces captured by the sensor.

The load cell on the smart probe is mounted axially, causing all the friction forces along the shaft of the probe to be registered as $F_Z$ on the load cell. Since the shaft of the probe is tapered such that the diameter of the probe increases from the tip of the probe, the friction forces become larger as the probe plunges further into the pedicle.

Figure 32:
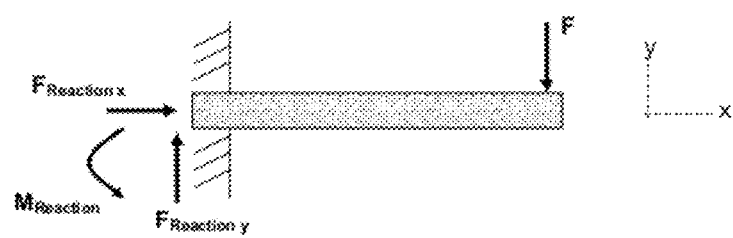
FIG. 32: Fixed member free body diagram.

Another driving principle based on the first assumption is that of the reaction due to a fixed member. A fixed support can be described as a support that oppose any motion of the free body and constrain it completely. This can be seen in FIG. 32, which shows a fixed member free body diagram.

Figure 33:
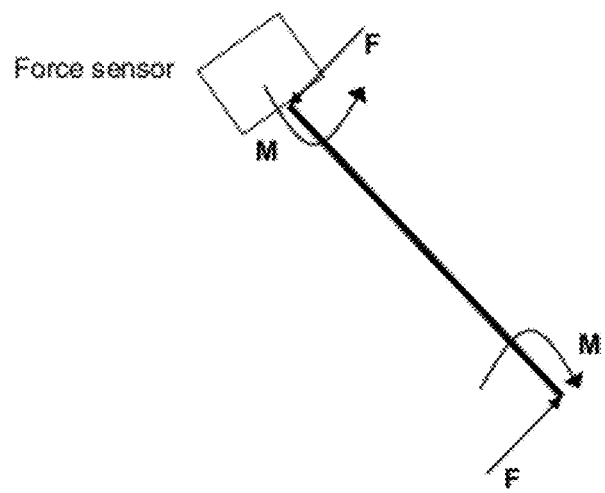
FIG. 33: Equal and opposite forces of the rigid tip of the spinal probe.

When a force is applied on an anchored rigid member, there is an equivalent reaction force and corresponding moment at the base. These reaction forces can be broken up in terms of x and y reactions. Based on the second assumption stating that the only radial forces are at the tip of the probe, and since the tip of the probe is made of rigid steel, it can be assumed that the forces and corresponding moments experienced at the tip are equal and opposite of the forces and corresponding moments experienced at the load cell. FIG. 33 shows equal and opposite forces of the rigid tip of the spinal probe.

Combining the principle of transmissibility and the physical laws governing a fixed member, a model can be developed for a probe navigating the pedicle. To begin, consider the probe as it travels through cancellous bone. As the probe travels through the pedicle, into cancellous bone, the only force present are shear forces in the form of friction. Refer to FIG. 31 for reference. These forces would register as axial compression forces on the force sensor.

Figure 34:
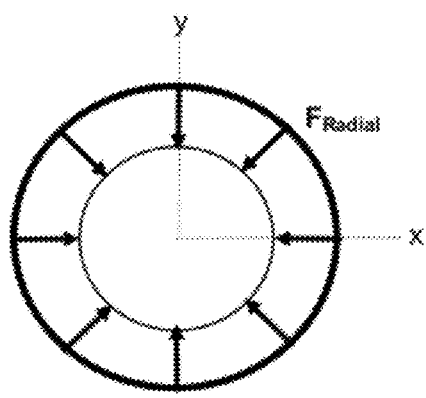
FIG. 34: Uniformly distributed shear force resulting in a negligible radial force.

From an axial perspective the shear forces are balanced and equally distributed along the circumference of the shaft. This assumes that the probe enters the pedicle in a consistently straight trajectory throughout the procedure. A tangible example of this type of trajectory is that of a nail being driven into wood. FIG. 34 shows uniformly distributed shear force resulting in a negligible radial force.

The force model changes as the probe approaches the cortex, however. No longer are the dominating forces in the form of friction. Instead, due to the presence of a boundary, there is a reaction shear force inflicted upon the tip of the probe by the wall. This shear force from the wall contains three components: a reaction shear, a normal component shear force perpendicular to the wall, and a vertical shear force due to the wall. These forces are modeled in FIG. 35.

Figure 35:
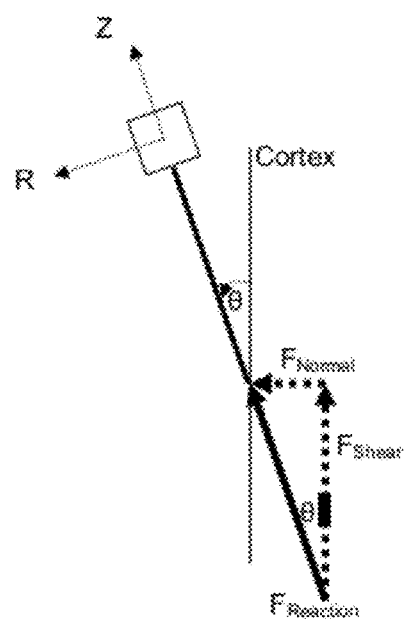
FIG. 35: Forces present at the cortex of the pedicle.

From the free body diagram in FIG. 35, the majority of the force inflicted by the cortex is transmitted axially in the force sensor. Again, the principle of transmissibility is dominating the physics. Additionally, it is assumed that the $F_{Shear}$ is negligable, since the probe will not slip at the cortex. However, the $F_{Normal}$ component, although small, will induce a shear force upon the tip of the probe in a radial direction.

Figure 36:
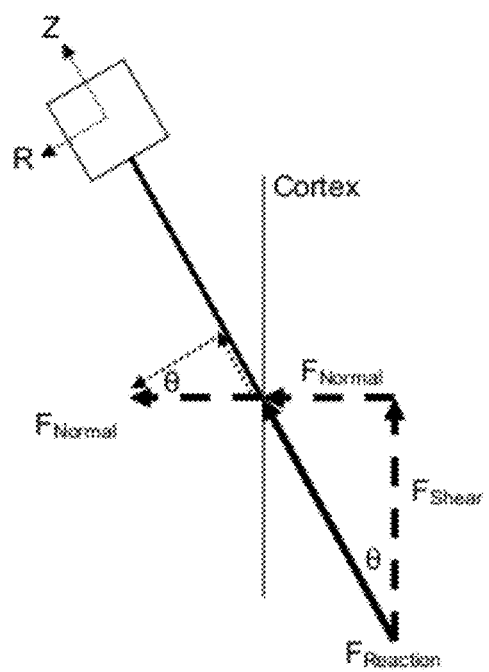
FIG. 36: Normal shear force breakdown.

FIG. 36 shows a normal force breakdown. FIG. 36 shows a very important principle and major assumption when developing the smart probe. As the angle θ approaches the zero with respect to the cortex, the radial component $F_{Normal}$ will become larger. The major assumption for the smart probe is that the angle at which it runs into the pedicle wall must always be less than 45 degrees. In contrast, once θ exceeds 45 degrees, the radial component of the normal force will be insignificant and no indicative.

Figure 37:
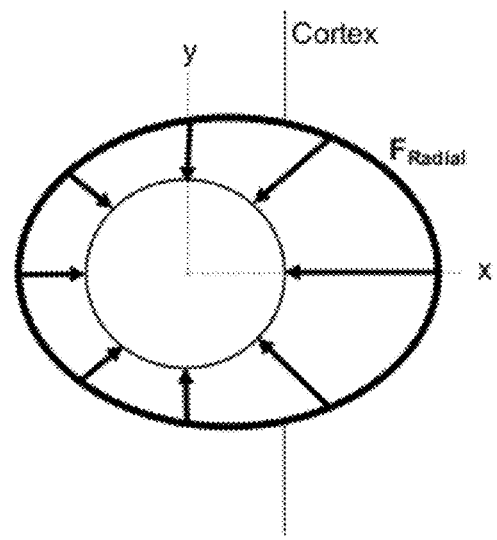
FIG. 37: Unbalanced distributed of shear force resulting in an increase in radial force.

From an axial perspective at the cortex, the forces are no longer balanced or equally distributed along the circumference of the shaft. At the cortex, the probe tip is now being deflected from the wall due to a larger amount of reaction force from the cortex. FIG. 37 shows unbalanced distributed of shear force resulting in an increase in radial force In conclusion, two physical principles drive the mechanical forces in the pedicle tract procedure. The first principle is the principle of transmissibility and second is the reaction due to a fixed member. These principles assume that object of study is a rigid member. Applying these principles to the spinal probe, other assumptions were made in order to fully describe the system. These assumptions are as follows:
1. Because the tip of the spinal probe is a rigid member, all forces at the tip are equal and opposite those at the load cell.
2. All radial forces are due to the tip of the spinal probe being obstructed by a boundary such as the cortex of the pedicle.
3. The spinal probe enters the pedicle in a straight trajectory, like a nail penetrating a piece of wood.
4. The tip of the spinal probe comes into contact with the cortex at a small angle (<45 degrees to the cortex).

Load Cell Characterization

Although ATI provided all the specifications of the load cell in their product data sheet, a characterization experiment was conducted in order to verify both the force units and the accuracy of the load cell. Placing calibrated weights on top of the load cell, 1000 data points of the axial force ($F_Z$) were recorded using the LabVIEW program. MATLAB was then used to plot the data and set a linear fit to the data.

Figure 38:
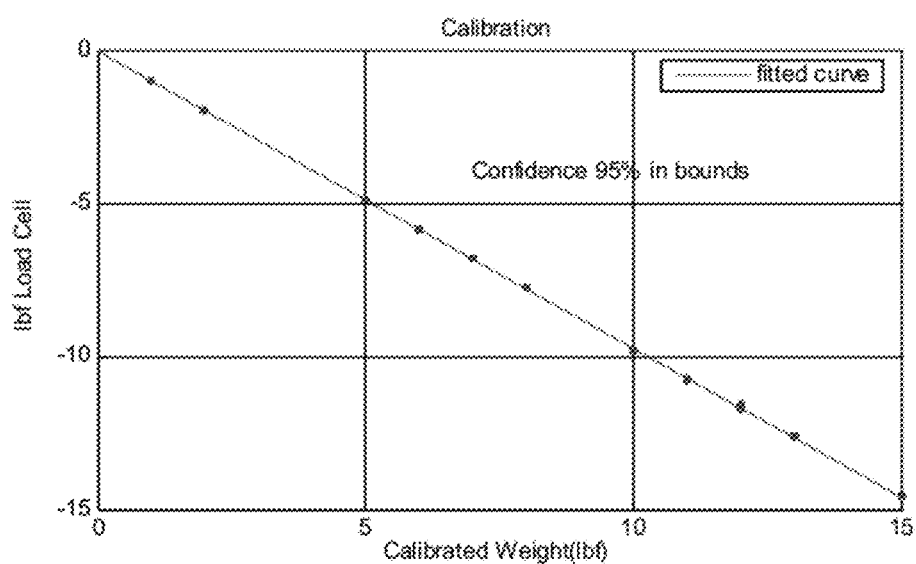
FIG. 38: Raw data collected on the load cell as a function of calibrated weight with fitted curve.

The load cell axial force data was plotted on the y-axis with the actual calibrated weight plotted on the x-axis. All the forces on the load cell were compressive forces with some error due to the weights not being perfectly aligned with their center of mass since the weights were significantly larger than the load cell. FIG. 38 shows raw data collected on the load cell as a function of calibrated weight with fitted curve Using MATALB, a linear curve was fit to the data, which can be seen in FIG. 38. The data in FIG. 86 shows a very strong linear correlation of the actual weight to the load cell reading (correlation=−0.9999).

Based on this test, it was concluded that the load cell measures force in pounds-force (lbf). Furthermore, this test indicates that the load cell is very accurate in measuring axial force. This was confirmed by the strong linear relationship between the load cell axial force reading and the set of calibrated weights.

In order to determine the characteristics of the x and y forces as well as their corresponding moments, a torque characterization experiment was conducted. The method of finding these test parameters involved hanging a calibrated weight at set distances, and measuring the torque output determined by the load cell. The motivation behind hanging a weight at the tip of the probe was to induce a shear force at the tip of the probe and measuring the response.

Figure 39:
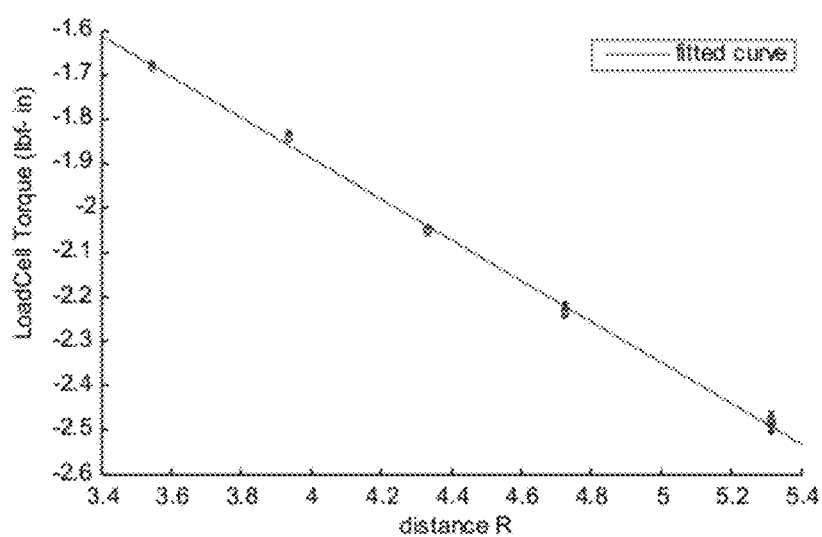

The resulting torque measurement as a function of distance was calculated for 100, 200, and 500 gram calibrated weights. The results for the 200 g trial can be seen in FIG. 39.

From the plot, there is a strong linear relationship (correlation=−0.999) between the torque and the varied distance. Furthermore, the slope of the association was confirmed to be the mass of the calibrated weight. These results were consistent at each weight. Therefore, it was concluded that the load cell was very accurate in determining the torque due to a shear force at the tip.

The final test in characterizing the load cell was to observe the forces present while rotating the load cell with an applied shear force. In order to complete this objective, the probe was clamped into a vise, resting upon two ball bearings so that rotation was possible while ensuring that the center of rotation was not fixed.

Figure 40:
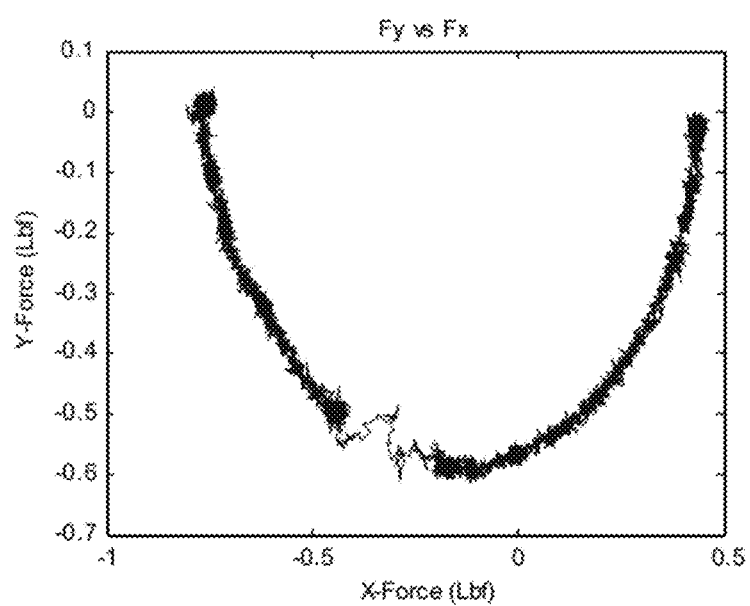
FIG. 40: Rotation of in the presence of a shear force at the tip of the spinal probes.

Like in the previous characterization study, a moment was created by inducing a shear force at the tip of the probe. This was done hanging a calibrated weight at a measured distance, R, from the center of rotation. A 200 gram weight was hung at set distances of and the probe was then rotated in the clockwise direction. Both the torque and forces were measured throughout the rotation. FIG. 40 shows rotation of in the presence of a shear force at the tip of the probe.

FIG. 40 show a very important concept in characterizing the effect of a shear force at the tip of a rigid member. The above figure demonstrates that the shear force rotates in a symmetrical ellipse when the probe is rotated. Furthermore, the above indicates that the center of the ellipse is approximately (0, 0). Although the above figure is not centered at exactly (0, 0), the offset is due to the small changed in radial arm as the string hanging the weight displaces with each wrap.

Capturing the Force Profile

The evaluation of the spinal probe was first used in a cadaver study before being evaluated in the laboratory. Seven plunges were attempted including vertebral levels T12, L1, L3, L4, and L5. Of the seven plunges, there were three breached pedicles and four no breach (intact) pedicles. Of the three breaches, two were medial breaches and one was a lateral breach. Visual confirmation of each plunge was affirmed using the Medtronic StealthSystem. Additionally, the cortex of each pedicle was removed before probing the pedicle. The following table shows the trajectory according to pedicle:

| Pedicle | Trajectory |
| --- | --- |
| L5 Left | Lateral Breach |
| L4 Left | In |
| L3 Left | Medial Breach |
| L1 Right | Medial Breach |
| L1 Left | In |
| T12 Right | In |
| T12 Left | In |

This study provided valuable information regarding the force profile using the spinal probe. First, the force profile revealed a range of forces seen in a typical pedicle tract procedure. Second, the profile showed distinctive characteristics of breached pedicle when compared to an intact pedicle. Finally, the profile revealed that it may be possible to predict a pedicle breach based on these fore measurements.

Figure 41:
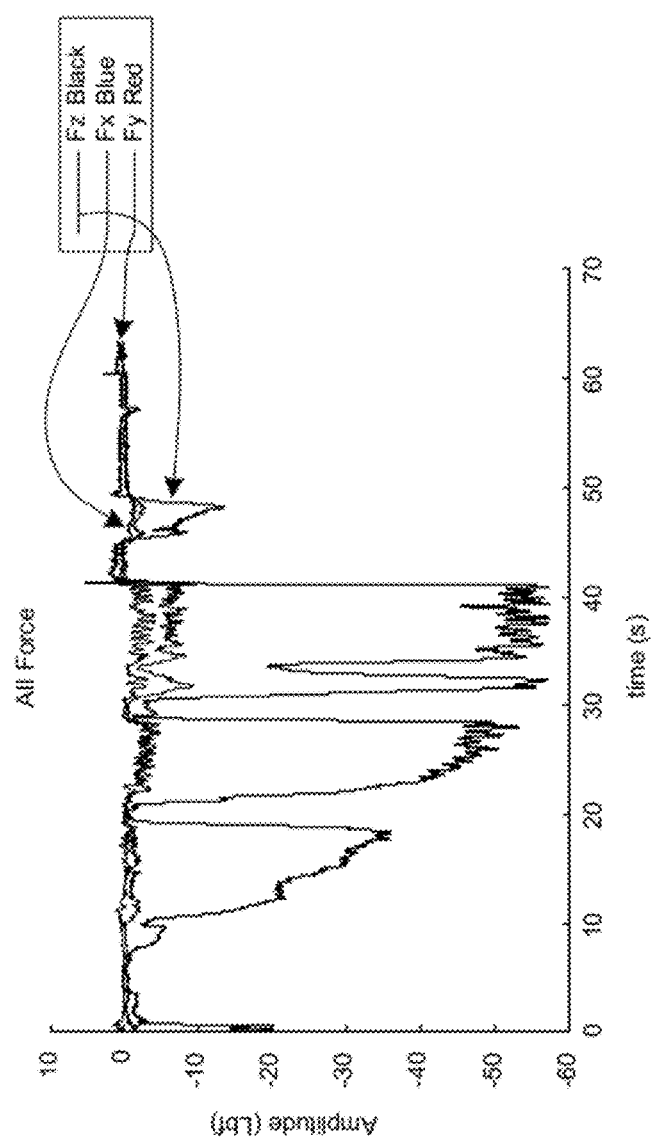
FIG. 41: Unprocessed force profile of lateral breach in the right pedicle of L5.

FIG. 41 is an unprocessed force profile of a lateral breach in the right pedicle of L5. Note that the abrupt rise and fall of FZ are pauses in the procedure. These pauses typically are made because the surgeon is checking the StealthSystem monitor to ensure the correct trajectory is being followed, readjusting their grip, or taking a quick break before continuing.

Figure 42:
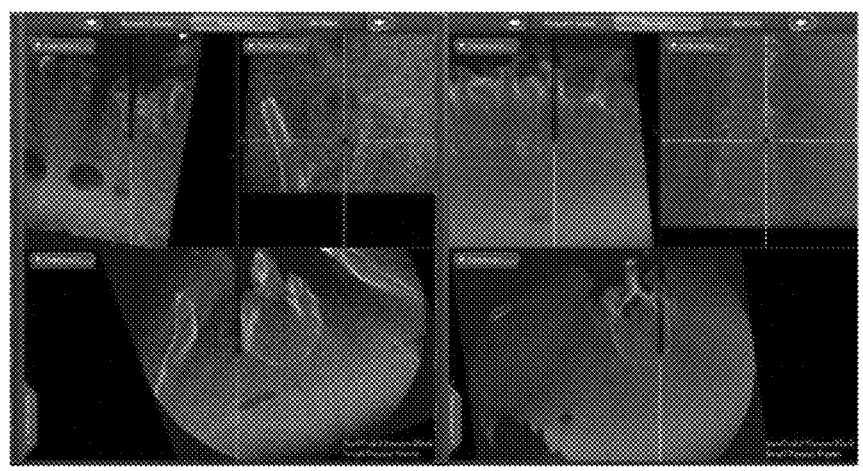
FIG. 42: A screen shot of lateral breach in the left pedicle of L5 (left) and an intact trajectory of the left pedicle of T12 (right).

As mentioned, the trajectory was confirmed using the StealthSystem. The resulting trajectory taken in this particular breach can be seen in the left image of FIG. 42. FIG. 42 is a screen shot of lateral breach in the left pedicle of L5 (left) and an intact trajectory of the left pedicle of T12 (right)

Figure 43:
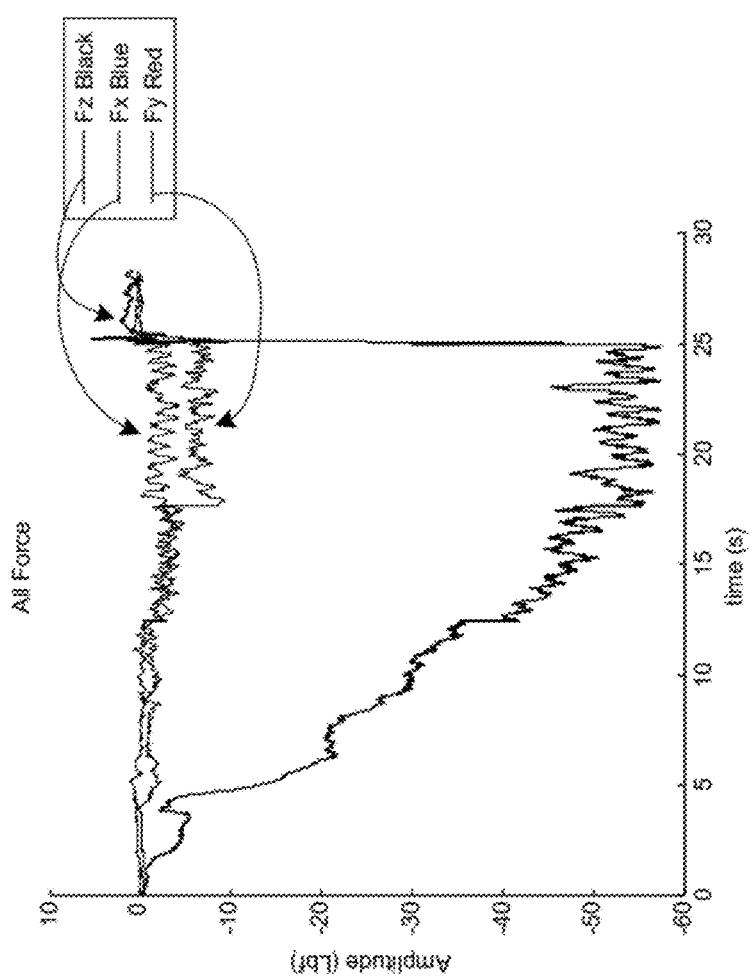
FIG. 43: Profile of a lateral breach in the right pedicle of L5.

In order to get a better understanding of the force profile, the data was post-processed using MATLAB. Only the data corresponding to the plunge was used and all of the pauses were removed. FIG. 43 is a force profile of a lateral breach in the right pedicle of L5 with the pauses removed.

From the plot, three distinct regions can be concluded. The first region consists of the profile between time t=0 s to approximately time t=17 s. Within this region, the probe has traveled through the cancellous bone within the pedicle in a relatively straight manner. This conclusion is based on the small amount of forces in x (blue) and y (red), and the majority of forces being in z (black). In terms of mechanical forces, there are no radial shear forces from an obstruction and only axial shear forces due to the increasing tapered diameter of the smart probe.

The second region of the profile begins at approximately time t=17 s and ends at approximately time t=25 s. Within this region, there is a relative flattening of the force in the z direction and a substantial increase in magnitude of the forces in the x and y directions. From a mechanical force standpoint, this would indicate the tip of the probe has been obstructed. The flattening of the force in the z direction corresponds to the reaction force of the wall while the increase in the forces in x and y would indicate the radial shear force due to the obstruction.

The third and final region would be the large change in the profile at approximately time t=25 s. This region characterizes the effect of a breach of the pedicle. At time t=~25 s the cortex is penetrated and the smart probe plunges through the cortical wall bringing all the force back to zero as the surgeon no longer pushes on the awl.

Figure 44:
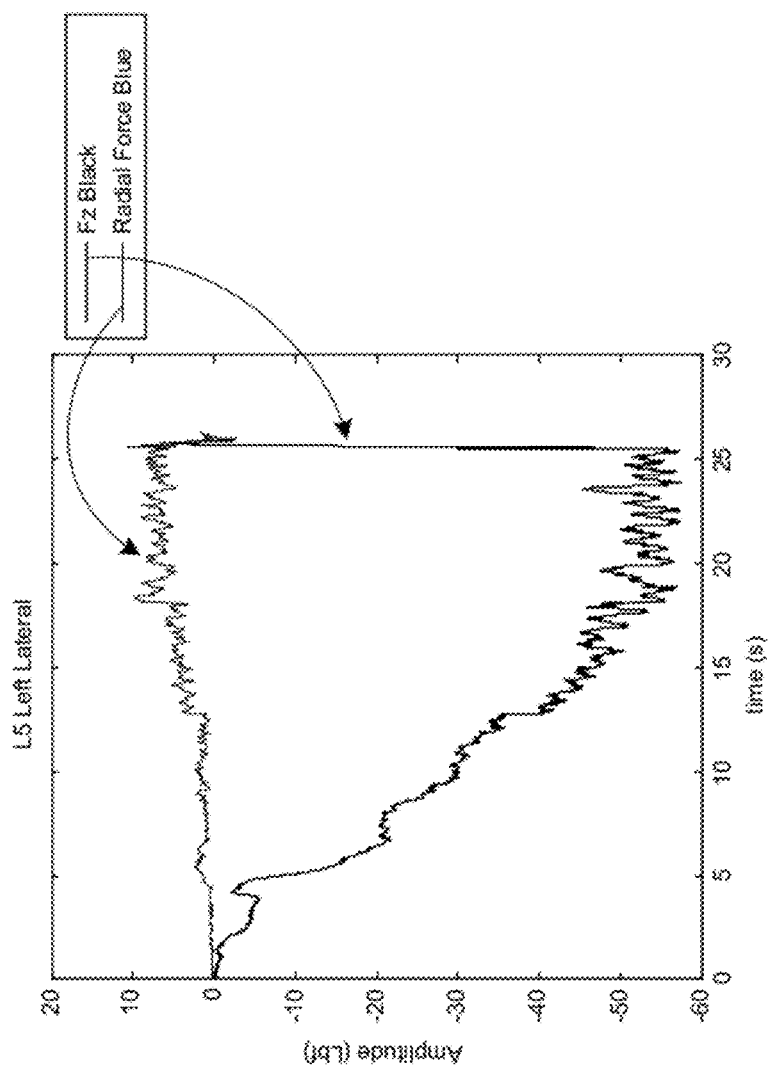
FIG. 44: Radial force profile of lateral breach in the left pedicle of L5.

Region two is of most importance and leads one to believe that a breach can be predicted based on the force characteristics present while performing the pedicle tract procedure. From a mechanical force standpoint, any obstruction will provide a radial shear force at the tip of the smart probe. While these forces will have an axial component in the z direction, there will also always be normal component in the radial sense. The axial force is equivalent to forces in the z direction while the radial force is the magnitude of $F_X$ and $F_Y$. FIG. 44 shows this increase in radial force.

FIG. 44 is a plot of the resulting radial force and axial force, FZ. Again, as the tip of the spinal probe comes into contact with the cortex, the axial forces become relatively steady. Meanwhile, the radial forces increase substantially due to the shear forces inflicted on the tip by the cortex. Finally, the cortex is breached and the forces return to zero. Therefore, this increase in radial force could serve as an indication to surgeons as to whether or not the pedicle is going to be breached.

In comparison, an intact profile does not contain the same type of force characteristics. Instead of an increasing radial force as seen in FIG. 44, there is a more consistent value.

Figure 45:
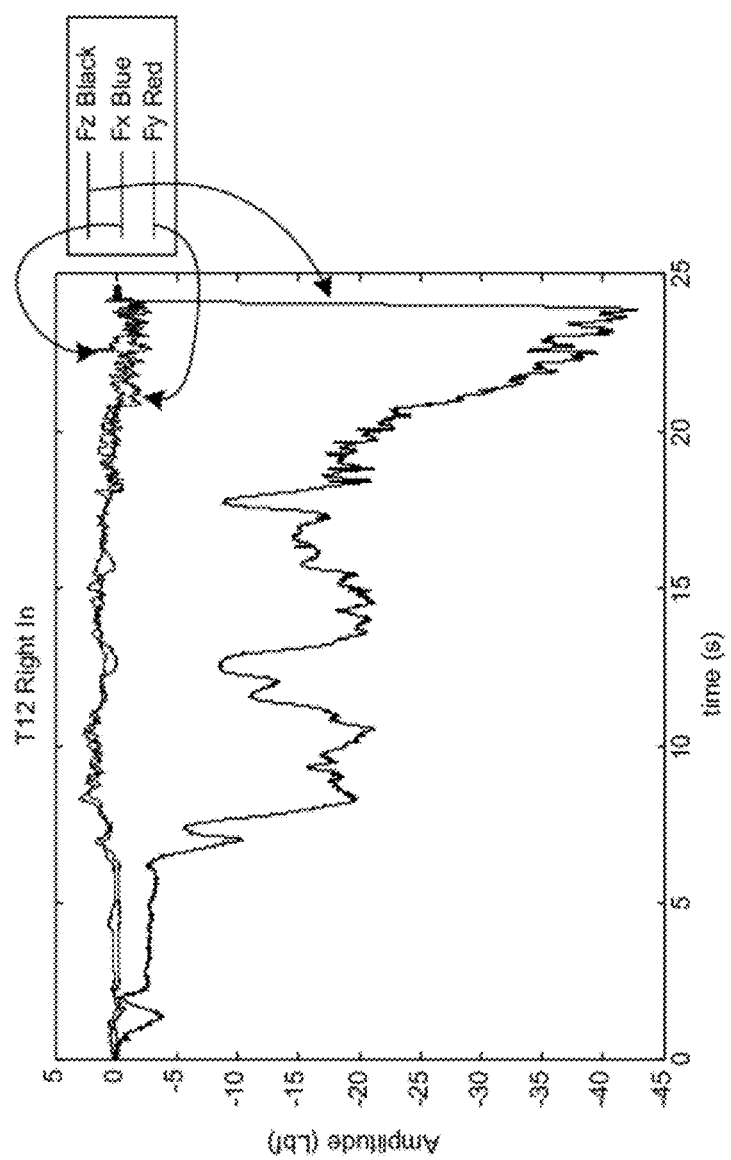
FIG. 45: Force profile of intact trajectory of the right pedicle of T12.

FIG. 45 shows a force profile of intact trajectory of the right pedicle of T12. The profile in FIG. 45 does not contain the same characteristics as those seen in the lateral breach of the right pedicle of L5. Here, the force has a small increase x and y forces around time t=5 s and then stays relatively constant throughout the plot until time t=20 s. At this point the force in z makes quick descent which is due to the increasing diameter of the spinal probe's taper. The radial representation of x and y forces can be seen in FIG. 46.

Figure 46:
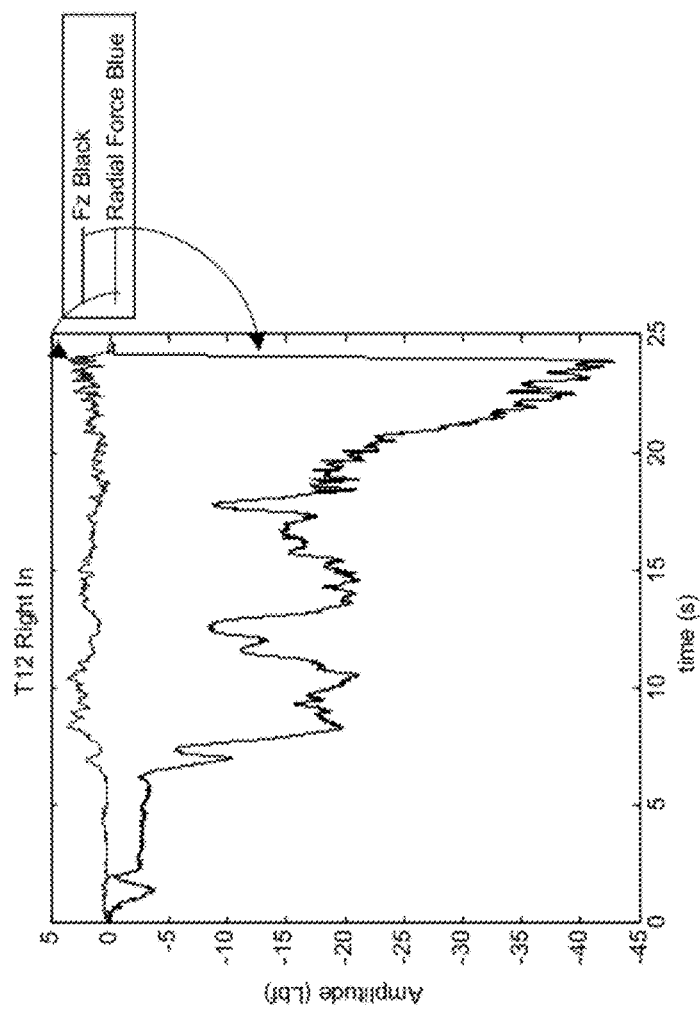
FIG. 46: Force profile of intact trajectory of the right pedicle of T12.

FIG. 46 shows a force profile of intact trajectory of the right pedicle of T12. The resulting radial force in FIG. 46 is much smaller in magnitude than that of the lateral breach in L5. The increase in radial force in the intact trajectory was probably due to shear forces inflicted on the handle of the spinal probe by the surgeon.

One drawback of calculating the radial force is that it eliminates the direction of the force in x and y. Therefore, an additional way of representing the radial force, while still maintaining the direction of FY and FX data, is to plot FY as a function of FX.

Figure 47:
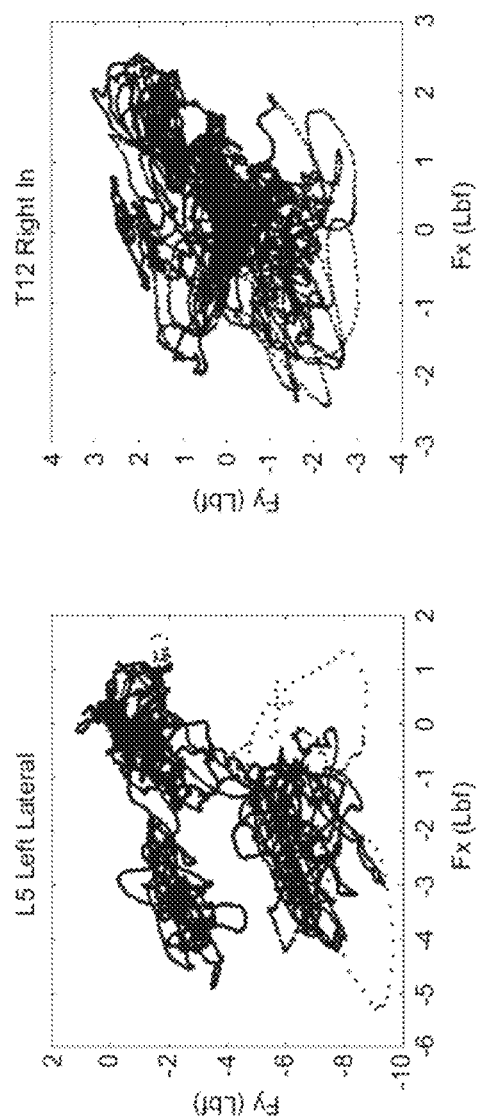
FIG. 47: FY(FX) plot for lateral breach of the left pedicle of L5 (left) and intact of the right pedicle of T12 (right).

FIG. 47 is an $F_Y(F_X)$ plot for lateral breach of the left pedicle of L5 (left) and intact of the right pedicle of T12 (right). In FIG. 47, the majority of the forces hover around point (0, 0) in both the lateral breach and intact plots. This is equivalent to minimal radial forces initially seen in FIG. 44 and FIG. 46. However, there are distinct deviations from (0, 0) on the lateral breach sample while the intact data is more tightly grouped. The deviations from (0, 0) indicate an increase in the x and y forces, or rather, the an increase in the radial force. Furthermore, these deviations could, in fact, predict whether or not the spinal probe is about to breach the pedicle.

Comparing the two plots in FIG. 47 on the same axis helps exemplify the differences in the $F_Y(F_X)$ data sets. The intact data, indicated in red, is clearly more compact than the lateral breach data in blue.

Figure 48:
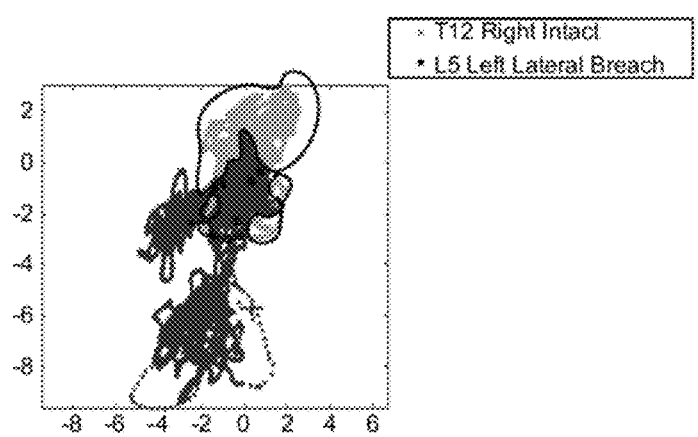
FIG. 48: FY(FX) plot showing distinct difference in comparing breach data to intact data.

FIG. 48 is an $F_Y(F_X)$ plot showing distinct difference in comparing breach data to intact data. Although theoretically there should not even be a presence of a radial component of the force in an intact trajectory, one could assume that there are external forces from a variety of variables. These radial forces could be coming from the shaft of the spinal probe bumping up against the cortex or from shear forces inflicted by the surgeon on the handle of the spinal probe.

Figure 49:
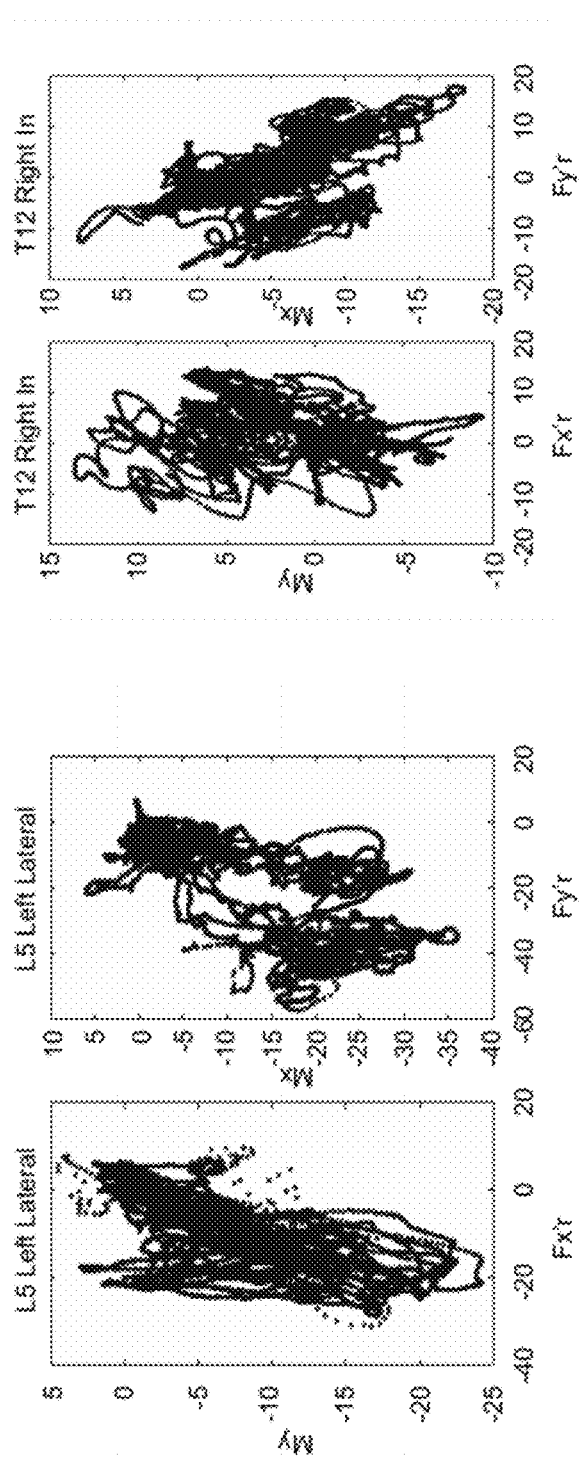
FIG. 49: Moments in x and y plotted as a function of the corresponding cross-product.

In order to check whether or not the radial forces are due to shear forces at the tip, the moments about x and y were plotted against their corresponding forces scaled by the distance to the tip of the spinal probe. If all the radial forces are the result of shear at the tip of the spinal probe, the relationship between the moment and its corresponding cross-product should be linear with a strong correlation. FIG. 49 shows the moments in x and y plotted as a function of the corresponding cross-product The correlation of the moments in the lateral breach proved to have a strong linear association. For the lateral breach, the moment about y ($M_Y$) and its corresponding cross-product, r×$F_X$, had a correlation value of 0.7708 while the moment about x ($M_X$) and its corresponding cross-product, r×$F_Y$, had a correlation value of 0.800. Meanwhile for the intact data, $M_Y$ and its corresponding cross-product, r×$F_X$, had a correlation of 0.2525 while $M_X$ and its corresponding cross-product, r×$F_Y$, had a correlation of −0.5711. Since the correlation is substantially strong for the breach sample, it is safe to assume that the increase in radial force was due to the tip of the smart probe coming into contact with the cortex of the pedicle. Furthermore, the poor correlation seen in the intact data can lead one to assume that the radial forces most likely have come from the shaft of the smart probe coming into contact with the cortex or external forces inflicted by the user along the handle.

With such a small amount of data, a statistical evaluation cannot be made. However, the mean and the standard deviation for each trial can be seen in the following table.

TABLE 7

Radial and Axial (FZ) means and standard deviations of the cadaver study

| | $\mu_{Radial}$ | $\sigma_{Radial}$ | $\mu_{Axial}$ | $\sigma_{Axial}$ |
|---|---|---|---|---|
| L5 Right Lateral Breach | 4.04 | 2.50 | −40.38 | 12.80 |
| L4 Left Intact | 3.59 | 1.60 | −32.86 | 14.64 |
| L3 Left Medial Breach | 2.83 | 2.04 | −36.75 | 20.50 |
| L1 Left Intact | 1.91 | 1.37 | −29.98 | 16.86 |
| L1 Right Medial Breach | 2.46 | 1.31 | −44.10 | 4.65 |
| T12 Left In | 1.69 | 0.94 | −34.00 | 16.56 |
| T12 Right In | 1.61 | 0.71 | −30.73 | 10.78 |

The largest amount of radial force came from the lateral breach of the right pedicle in L5, with a mean radial force of 4.04 lbf and a standard deviation of 2.50 lbf. Conversely, the lowest mean radial force came from the intact placement in the right pedicle of T12, with a mean radial force of 1.61 lbf and a standard deviation of 0.71 lbf. Additionally, the larges axial force was in the medial breach of the right pedicle of L1, with a mean axial force of −44.10 lbf and a standard deviation of 4.65 lbf. Conversely, the smallest axial force came from the intact placement of the left pedicle of L1, with a mean axial force of −29.98 lbf and a standard deviation of 16.86 lbf.

Based on the results of the cadaver study, it was clear that when the tip of the spinal probe comes into contact with a boundary, there is an increase in radial force. Furthermore, an increase in radial force may be capable as serving as an indication of whether or not the tip of spinal probe is about to breach the pedicle. Due to the small sample size of this study, more data must be taken.

Laboratory Models

Since the cost of cadavers is so high, experiments were conducting using laboratory samples. Laboratory samples included foam, foam and clay, cardboard and clay, and cork and clay. The goal of these different samples was provide enough evidence that the specific force characteristics at a boundary could be confirmed. Additionally, the clay and cork sample provided a basis for a method of predicting whether or not a breach is likely to occur.

The cadaver study helped indicate that the forces at a boundary will yield an absolute increase in the force in x and y, or in other words, an increase in the radial force. In order to verify that this happens at every boundary, several different laboratory models were developed and tested. To begin, a jig was built in order to guide the spinal probe into the sample in a relatively straight path. The jig consisted of a piece of plywood with a drilled hole at approximately 30 degrees to normal. The plywood was then screwed to a 2×4 for support. The sample was taped to the plywood in order to ensure that the sample did not push away from the tip of the spinal probe as force was applied.

The initial test sample was a three layered foam block. Each layer consisted of open-cell foam with an adhesive covered paper layer used to join the adjacent layer. Additionally, the third and final layer of paper was the thickest.

The procedure of the test began with inserting the tip of the spinal probe into the 30 degree guide hole until the tip was just touching the sample. Next, with the data analysis system acquiring data, the spinal probe was pushed through the sample until the tip penetrated the last layer of paper. The spinal probe was pushed at a steady rate in order to eliminate any pauses in the z forces.

The motivation behind choosing a three layered sample was to try to capture the characteristics of a boundary layer multiple times in a single trial. Additionally, with the third layer being the thickest, the hope was to simulate the thick cortex of the pedicle and hopefully see similar results to those in the cadaver study.

Figure 50:
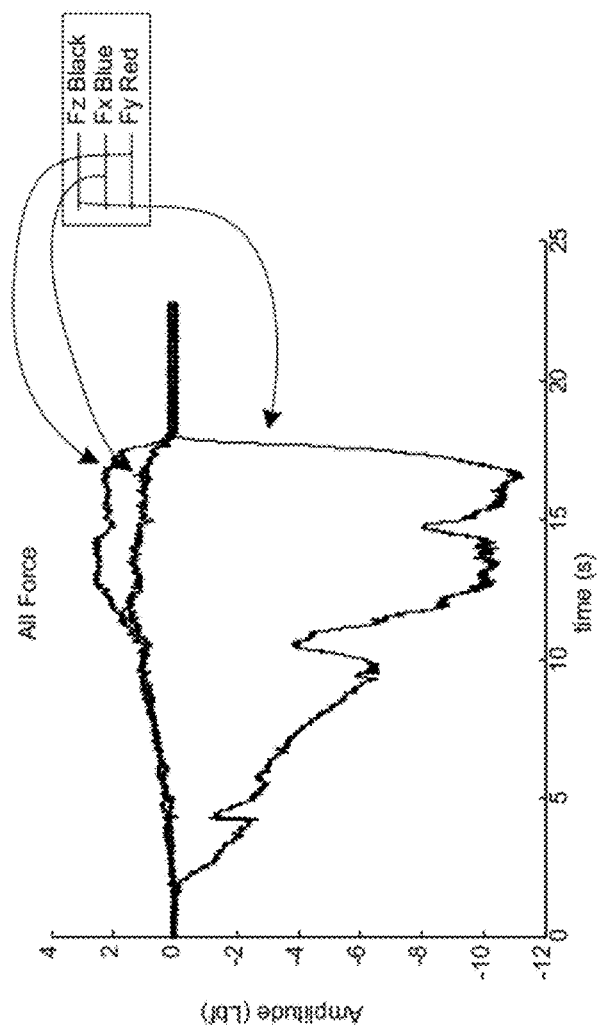
FIG. 50: Forces corresponding to three layered foam.

FIG. 50 shows the forces corresponding to three layered foam. From FIG. 50, three distinct humps can be seen in the $F_Z$ profile. These humps correspond to breaching the three different layers of paper. Additionally, as the smart probe approached the third hump, the $F_Y$ grew substantially, indicating the presence of a shear force due to a boundary.

Figure 51:
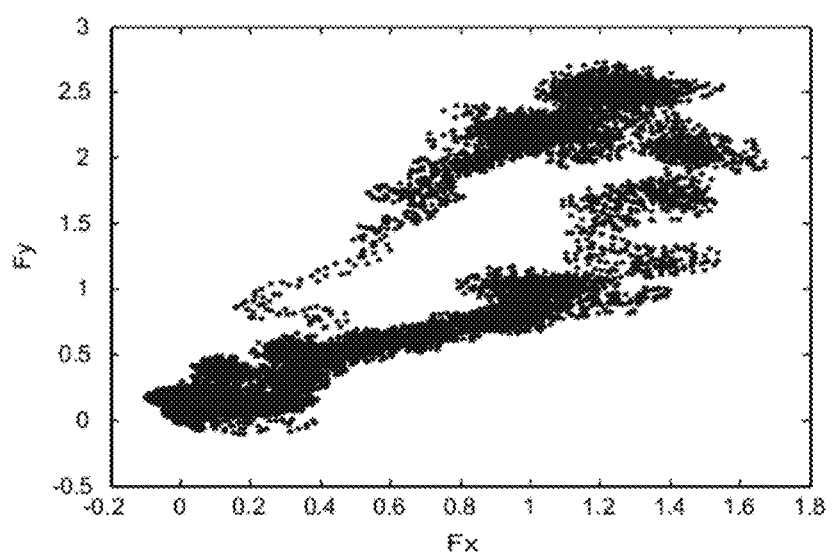
FIG. 51: Deviation of FY with respect to FX for three layered foam.

FIG. 51 amplifies the effect of the boundary by plotting $F_Y$ as function of $F_X$. Initially, the $F_X$ and $F_Y$ data will be non existent and it will hover around (0, 0). As the tip of the smart probe approaches the final boundary, the data deviates from (0, 0).

The procedure using the three layered foam was repeated several times in order to confirm the presence of a boundary would in fact cause a deviation in force of x or y. However, this test only illustrated the effects of an obvious boundary and did not show a significant change in the x and y forces at the more subtle initial layers of foam. In order to test whether or not the tip could distinguish a subtle boundary, a clay-foam model was tested.

The second test used the same jig as the three layer foam test; however now the sample consisted of a foam cup, cut in half and filled with clay. The cup was secured to the jig just as in the three layer foam test.

The procedure of this test was the same as in the three layer foam test. Similarly, the test showed the same result; which was that at a boundary, there is a distinct change in the x and y forces due to the shear force inflicted on the tip of the spinal probe by the boundary. The test was repeated several times to ensure that these conclusions held true.

Figure 52:
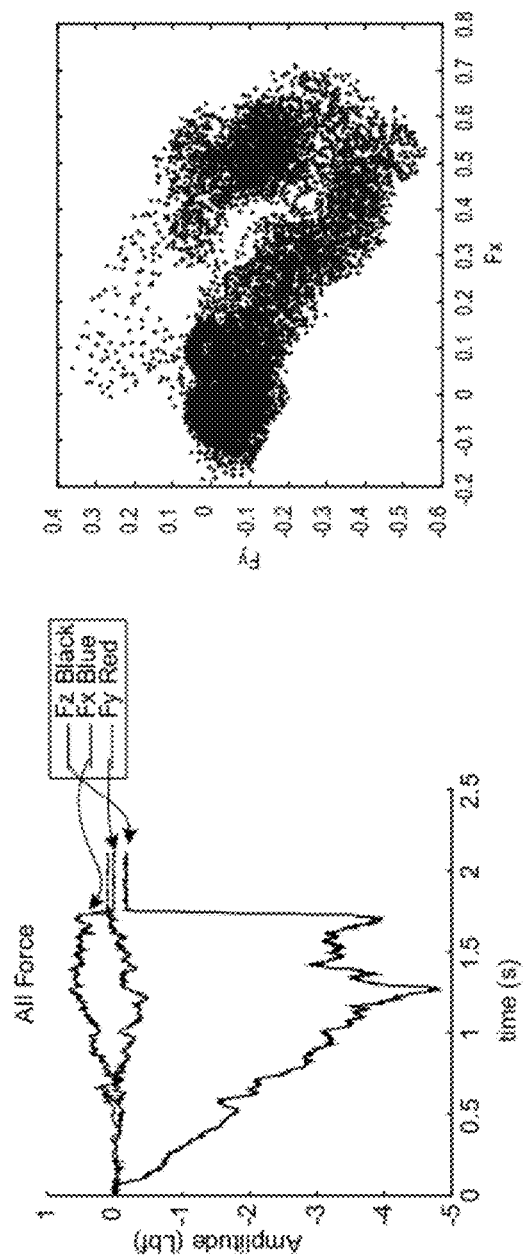
FIG. 52: Force profile (left) and deviation of Fx with respect to Fy of the clay-foam sample.

The resulting force profile can be seen in FIG. 52 along with the $F_Y$ as a function of $F_X$. From the figure, there is growth in $F_X$ as the approaches the boundary. Additionally, in the $F_Y(F_X)$ plot, the data deviates from (0, 0) just as it did in the previous test Both the test involving the three layer foam and the test involving the clay and foam samples showed an absolute growth in the x and y forces, or rather the radial force, as the tip of the spinal probe came into contact with a boundary. However, to better simulate the extreme density difference between cortical and cancellous bone, a cardboard boundary was used.

Figure 53:
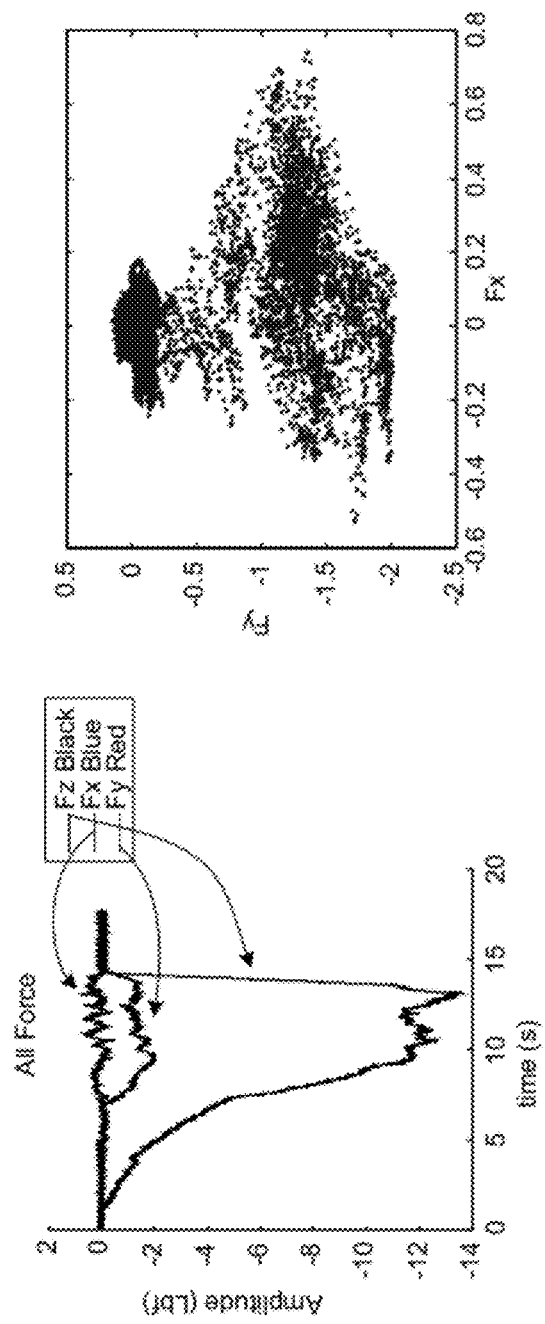
FIG. 53: Force profile (left) and deviation of Fx with respect to Fy of the clay-cardboard sample.

The same procedure was used with the clay and cardboard sample as was with the two previous tests. Additionally, just as there was a distinct increase in the radial force at the boundary with the two previous samples, there was a distinct increase in the radial force at the cardboard boundary. These results can be seen in FIG. 53, which shows a force profile (left) and deviation of $F_x$ with respect to $F_y$ of the clay-cardboard sample Based on the results of these three tests, it was accepted that at a boundary, no matter how distinct, there will be an in increase in the radial force do to the shear force inflicted by the boundary on the tip of the spinal probe. However, these three tests did not verify whether or not the increase in radial force was at the boundary or sometime before or after. Therefore, an apparatus that could measure force as a function of distance had to be constructed in order to establish the driving physics when the spinal probe came into contact with a boundary.

In order to verify the force characteristics at a distinct boundary, an apparatus was built that would limit the degrees of freedom of the spinal probe to only one direction as well as measure the distance the spinal probe had moved throughout the test. A major assumption of the prediction method is that the radial forces collected by the load cell are only the forces at the tip of the spinal probe. In other words, it is assumed that there are no forces being inflicted on the shaft of the spinal probe. Limiting the degrees of freedom to only one direction allowed the spinal probe to penetrate the sample so that no external forces on the shaft of the spinal probe would be collected by the load cell.

The apparatus used to measure distance and while limiting the degrees of freedom of the spinal probe consisted of the spinal probe mounted onto drawer sliders, fixed so that the tip of the spinal probe comes into contact with the specimen at a fixed angle of approximately 60 degrees to the table top. At this angle, the spinal probe enters the specimens at a 30 degree angle.

The specimens consisted of a one inch layer of clay followed by ¼ inch cork sample. Clay was chosen to represent the cancellous core of the pedicle and the cork was chosen to represent the cortex. Clay was used as a cancellous bone sample because of its spongy feel with the spinal probe. Additionally, cork was used because of its porous characteristics, which are similar to cortical bone. The cork was significantly harder than the clay but was also easily penetrated by the spinal probe. The tactile feel of both materials were verified with University of Minnesota Spine Surgeons.

Figure 54:
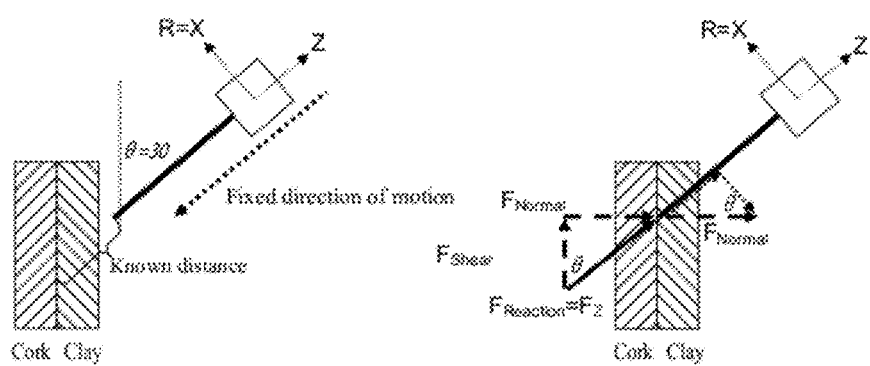
FIG. 54: Free body diagram of clay-cork interface.

As the spinal probe enters the specimens, reaction forces caused by clay inhibit the advancement of the spinal probe. These forces cause an increase in z direction, or rather, axial forces on the load cell. However, once the spinal probe comes into contact with the cork boundary, there is radial component of the reaction force caused by the boundary wall. The load cell was mounted onto the apparatus so that these forces would cause only an increase in the x direction in the load cell. In other words, the radial force component was equivalent to the force in the x direction. FIG. 54 is a free body diagram of clay-cork interface.

Figure 55:
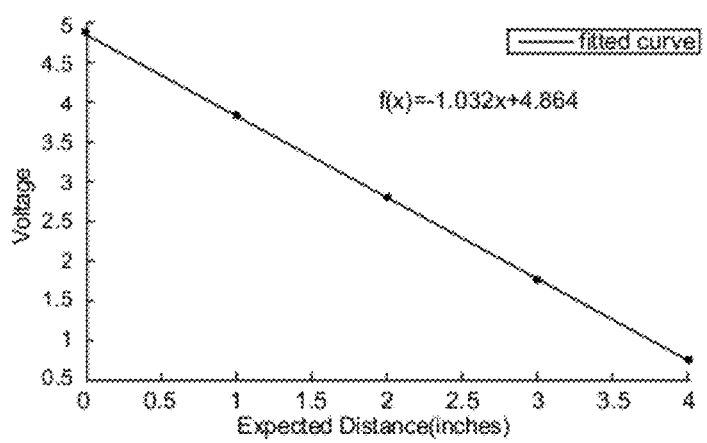
FIG. 55: Calibration curve for relating voltage to distance.
Figure 56:
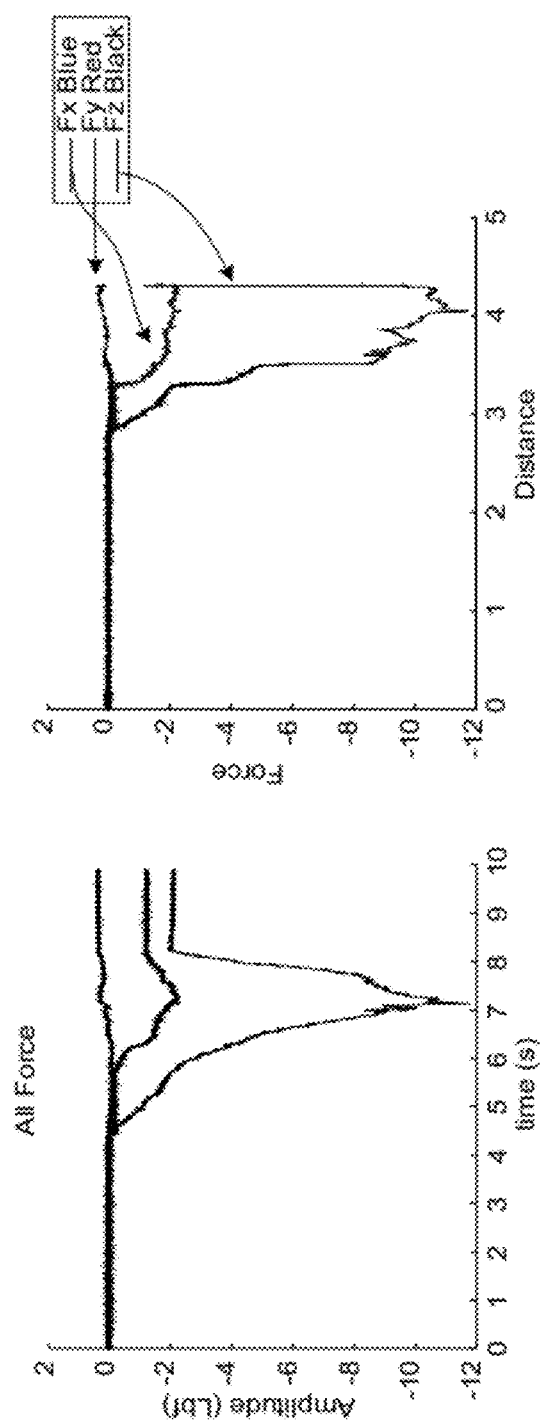
FIG. 56: Force as a function of time in seconds, F(t) (left). Force as function of distance in inches, F(d) (right).

The movement of the spinal probe mounted on the apparatus was limited to only translational changes along the z axis of the load cell. In order to capture the distance the spinal probe advanced during each trial, a potentiometer was mounted onto the apparatus. A wheel was attached to the axle of the potentiometer with a string wound around the wheel. One end of the string was attached to the spinal probe while on the other end of the string was a weight. As the spinal probe advanced toward the wheel, the weight would provide enough tension in the string to rotate the wheel, thus rotating the potentiometer. With rotation of the potentiometer, there was a proportional change in voltage. This change in voltage was recorded using the same data analysis system as the load cell to ensure that the samples were collected at the same rate. The distance the spinal probe moved was linearly proportional to the change in voltage on the potentiometer. Taking a calibration measurement, the relationship between voltage and distance was easily established. FIG. 55 shows the calibration used for converting voltage to translational distance. The observed error in the distance was approximately 0.1 inch, based on visual readings. These errors were mostly due to slippage in the string and slop in the drawer sliders. FIG. 55 shows a calibration curve for relating voltage to distance For each specimen, both force data as a function of time and force data as a function of distance were collected. Comparing both outputs side by side reveals a more complete representation of the force characteristics of the smart probe in the presence of a boundary. Using MATLAB to post-process the data, force as a function of time (F(t)) and force as a function of distance (F(d)) were graphed side by side, as shown in FIG. 56. FIG. 56 shows force as a function of time in seconds, F(t) (left). Force as function of distance in inches, F(d) (right).

It can be concluded from FIG. 56 that there is an obvious increase in the magnitude of $F_X$ at approximately t=6 seconds and approximately at distance d=3.5 inches. Additionally, there is a small increase in $F_Y$, however, this is most likely due to asymmetries in the smart probe since there should be no force in the y direction due to the orientation in which the smart probe was mounted.

Upon inspection, F(d) gives a much cleared picture of the physics present at the boundary. From FIG. 56, it is clear that there are no initial increases in forces in $F_X$ and $F_Y$, while there is an increase in $F_Z$. As $F_X$ splits from $F_Y$, $F_Z$ quickly descends, indicating an increase in compressive force. In other words, this indicates that the smart probe is at the clay-cork boundary.

Having recorded the distance to the boundary before conducting the test, the boundary conditions described above were confirmed. Furthermore, converting the forces from x, y, and z to radial and axial forces is important in fully analyzing the data. Again, the axial force is equivalent to forces in the z direction while the radial force is the magnitude of $F_X$ and $F_Y$.

Figure 57:
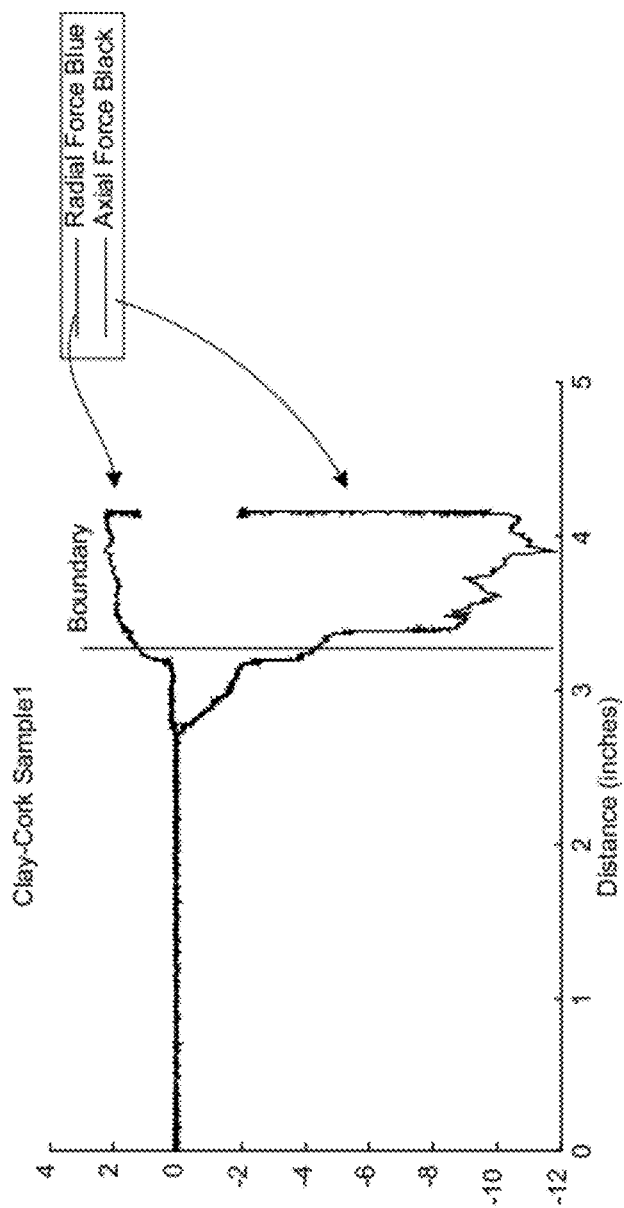
FIG. 57: Radial force and axial force plot at known boundary (green).

FIG. 57 shows the radial and axial forces as well as the known boundary recorded before the test. FIG. 57 shows that there is a large increase in the magnitude of both the radial and axial forces at the boundary. Therefore, this increase verifies that when the tip of the spinal probe comes into contact with a boundary, there is an increase in radial force.

In comparison, trials where no boundary was present were also collected. An example of such a trial can be seen in FIG. 58.

Figure 58:
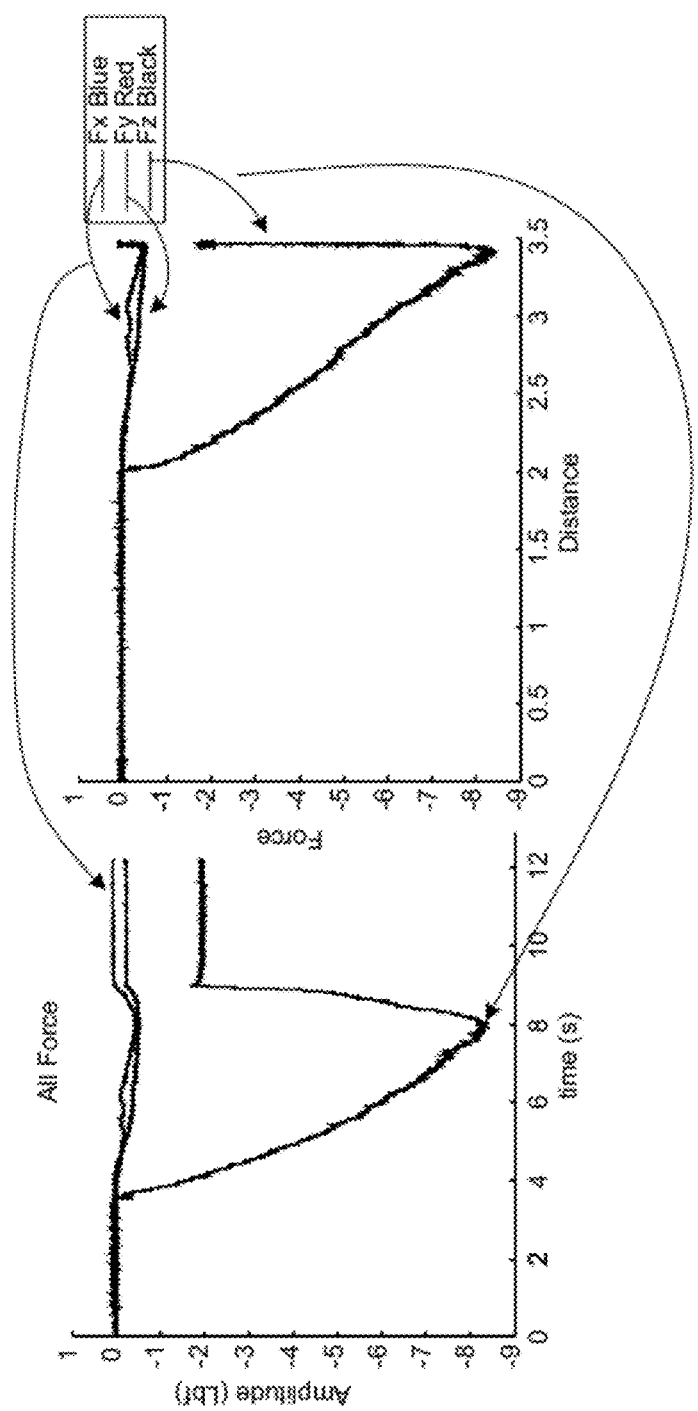
FIG. 58: Force as a function of time in seconds (left). Force as function of distance in inches (right).

FIG. 58 shows force as a function of time in seconds (left). Force as function of distance in inches (right). The data in FIG. 58 shows that there are no dramatic changes in the x and y forces. Additionally, there is no sudden drop in $F_Z$.

Figure 59:
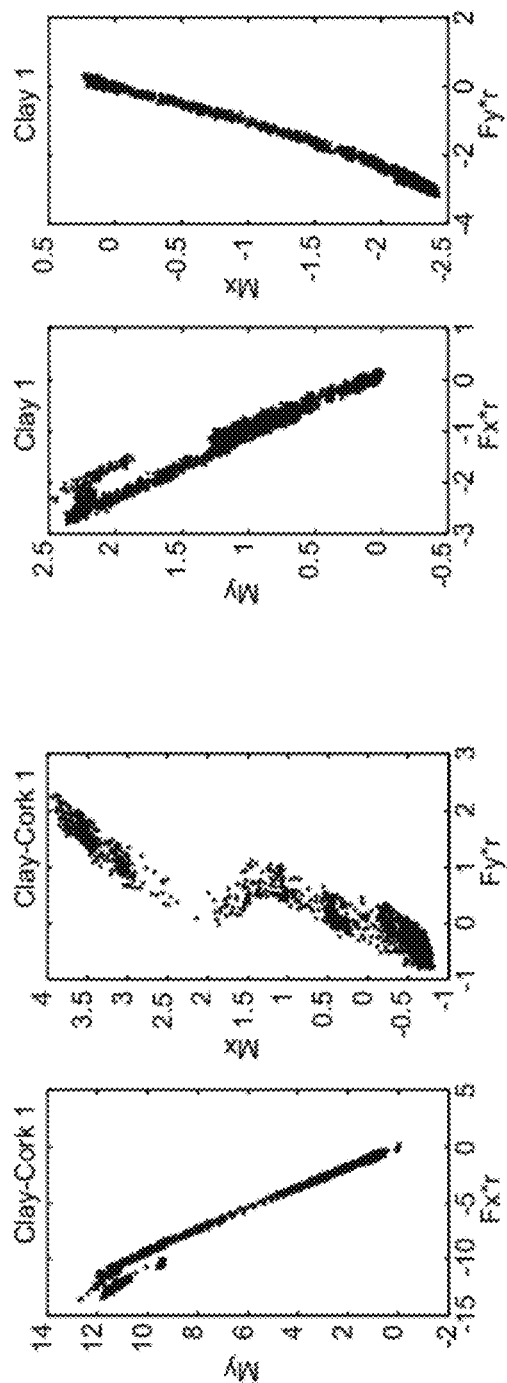
FIG. 59: Clay-cork sample 1 correlation plots of and (left) and clay only sample 1 correlation plots of and (right).

A correlation test was conducted to ensure that the assumption regarding the increase in radial forces at the tip of the smart probe when in contact with the boundary held true. For each trial, the moment data was plotted against its corresponding cross-product r×F. Since the moment is simply a cross product of the moment arm and the corresponding force, the plotted data should have a linear correlation if the only forces present are those at the tip. FIG. 59 shows the plots of these correlations for the clay-cork sample and the clay only sample.

From FIG. 59, there is a strong correlation between the product of the moment arm and force and its corresponding moment. This conclusion is based on the strong linear trend of the data. Therefore, it can be concluded that in the clay-cork samples, the moment $M_X$ was only caused by a force $F_Y$ at the tip as well as the moment $M_Y$ was only caused by a force $F_X$ at the tip. The same can be shown for the clay only samples. Again, since there is a strong linear relationship, it can be concluded that in the clay only samples, the moment $M_X$ was only caused by a force $F_Y$ at the tip as well as the moment $M_Y$ was only caused by a force $F_X$ at the tip. The same can be shown for the clay only samples.

The specific correlation results can be seen in the following table.

| Data | Correlation |
| --- | --- |
| $(r \times F_X, M_Y)_{Clay-Cork}$ | −0.9955 |
| $(r \times F_X, M_Y)_{Clay\ 1}$ | −0.8390 |
| $(r \times F_Y, M_X)_{Clay-Cork}$ | 0.9512 |
| $(r \times F_X, M_Y)_{Clay\ 1}$ | 0.9804 |

With a strong linear correlation indicting that the radial forces collected are only those at the tip, $F_X$ and $F_Y$ were plotted to help better explain how the radial forces change at the boundary. In the $F_Y(F_X)$ plot, the forces in the x direction were plotted along the x axis while the corresponding forces in the y direction where plotted along the y axis. The $F_Y(F_X)$ plot can be seen in FIG. 60.

As mentioned, the major assumption of this model is that the radial forces will only be experienced at the tip in the presence of a boundary. Therefore, the $F_Y(F_X)$ data will be hover around (0, 0) until there is a boundary. Once the tip of the smart probe runs into the boundary, there should be an increase and increase in $F_X$ and a small increase in $F_Y$ which will appear as a deviation from (0, 0). Again, knowing where the boundary exists helps qualify the data.

Figure 60:
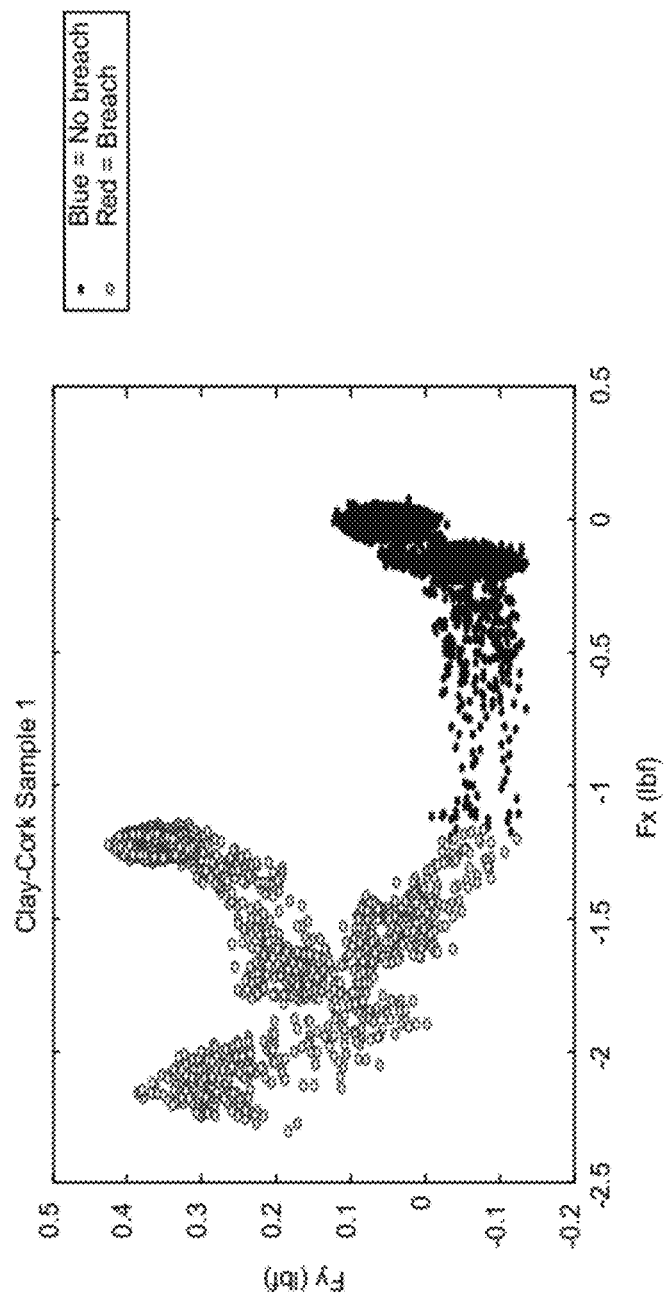
FIG. 60: FY (FX) plot indicating post-breach data (red) and pre-breach data (blue).

FIG. 60 shows the $F_Y(F_X)$ plot corresponding to the clay-cork sample previously mentioned. The data in blue represents forces in x and y before the breach. These forces, as mentioned above, hover around the (0, 0) mark. As the tip of the smart probe approaches the boundary, the data begins to deviate from the (0, 0) mark. The data in red represents the data after the boundary. From FIG. 60, it can be concluded that any large deviations from (0, 0) indicate whether or not a breach has occurred. In comparison to the clay only sample, there is a small absolute change in x and y forces, but using the $F_Y(F_X)$ plot, the changes of in the x and y forces can be better qualified.

Figure 61:
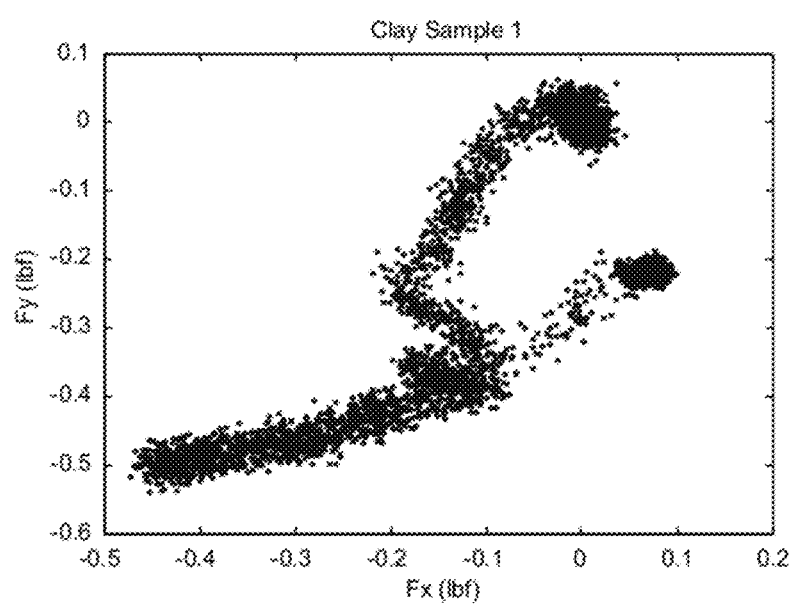
FIG. 61: FY (FX) plot indicating small deviations in x and y forces.

FIG. 61 is an example of an $F_Y(F_X)$ plot where there is no breach. Although there is a deviation from (0, 0) it is insignificant upon inspection of the scale of the plot. These deviations most likely have come from asymmetries in the spinal probe. Regardless, there will always be small deviations from (0, 0) due to differences in bone, asymmetries in spinal probes, and variations between surgeons.

Figure 62:
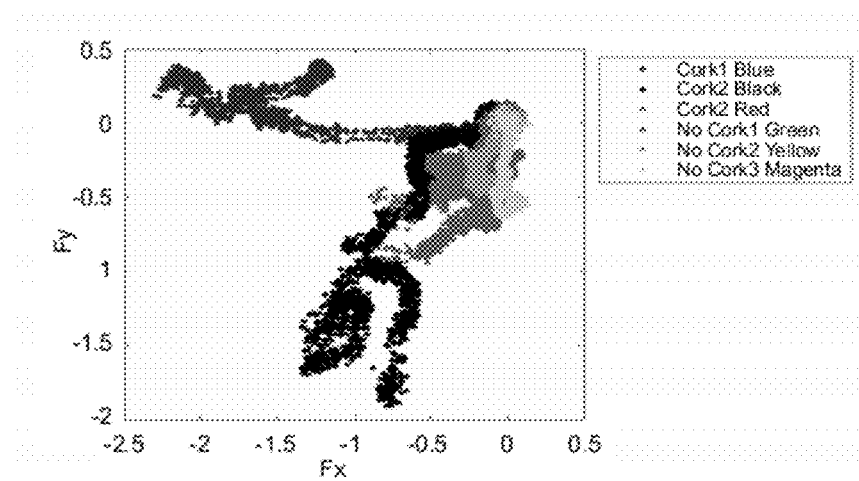
FIG. 62: FY (FX) plot of cork-clay samples against just clay samples.

Comparing $F_Y(F_X)$ plots for breached samples to no breach samples helps qualify the differences between breached samples no breach samples. FIG. 62 is an $F_Y(F_X)$ plot of cork-clay samples against just clay samples and shows these differences. That is, FIG. 62 illustrates the differences between samples with breaches and samples without. The clay samples (green, yellow, and magenta) have much smaller deviations from (0, 0) than the samples (blue, black, red) that had a cork boundary.

Figure 63:
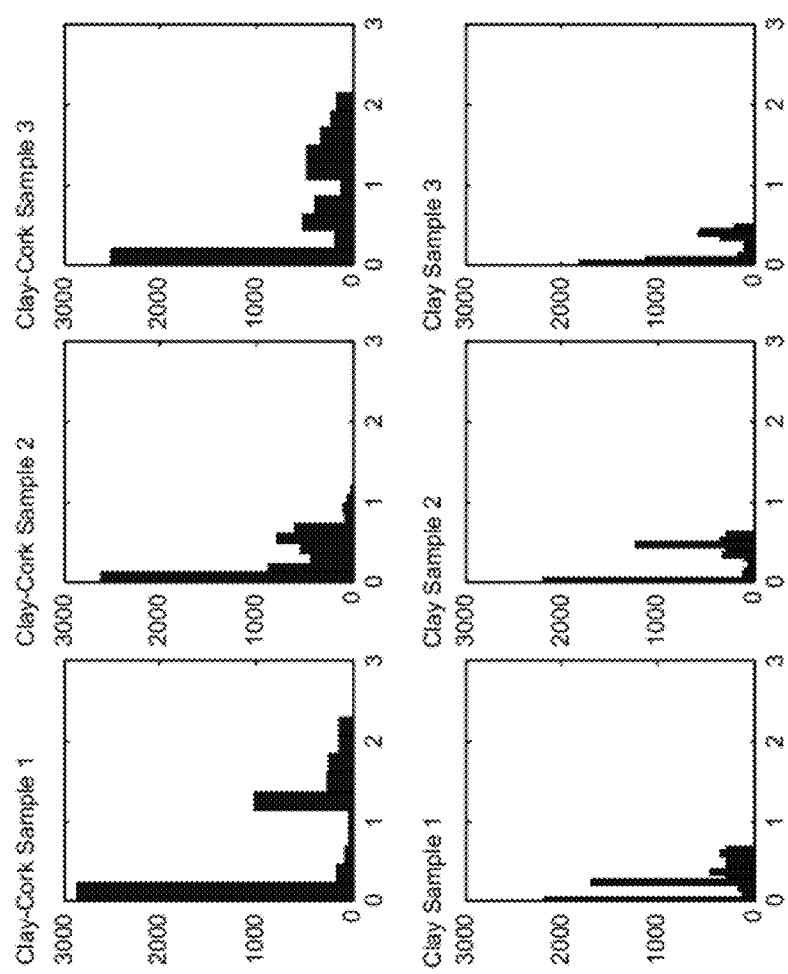
FIG. 63: Radial force distribution.

To further illustrate these differences, consider the distribution of the radial forces in FIG. 63. From FIG. 63, it can be concluded that the distribution of breached samples has a much larger variation in radial force than those of the no breach samples. In fact, the mean radial force for no breach samples (clay only) was 0.6726 lbf with a standard deviation of 0.1183 while the mean radial force for breached samples (clay-cork) was 1.5519 lbf with a standard deviation of 0.3249.

With the distribution of the data established, a one-way analysis of variance (ANOVA) test was conducted in order to determine if there was in fact a statistical difference between the mean of a no breach sample and the mean of a breach sample. For this statistical test, the null hypothesis was that the mean radial force of the two samples was the same. In contrast, the alternative hypothesis was that there was a difference between the radial force of the two sample means.

Using MATLAB, a one-way ANOVA test concluded that the probability of the null hypothesis being true was 0.044. In other words, the means will be the same only 4.4% of the time, which is sufficient enough evidence to conclude that the two samples were statistically different. The results of the ANOVA can be seen in FIG. 64 and Table 9.

Figure 64:
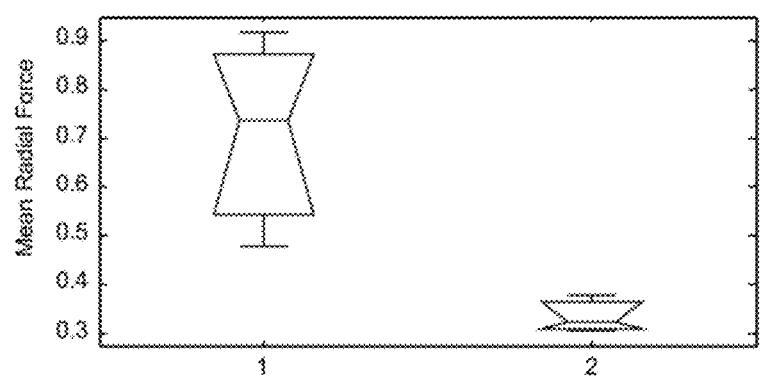
FIG. 64: Result of one-way analysis of variance. Sample mean radial force for breach on left (1) and no breach on right (2).

FIG. 64 shows the result of one-way analysis of variance. Sample mean radial force for breach on left (1) and no breach on right (2). In FIG. 64, the breach sample mean is represented on the left and the no breach sample mean is represented on the left. Table 9 gives more specifics based on the one-way analysis of variables test.

| Source | SS | df | MS | F | Prob > F |
|---|---|---|---|---|---|
| Columns | 0.21086 | 1 | 0.21086 | 8.43 | 0.044 |
| Error | 0.10005 | 4 | 0.02501 | | |
| Total | 0.31091 | 5 | | | |

Based on these statistical differences and confirmation that the only radial forces present were those at the tip, a failure criterion was established to predict whether or not the spinal probe was about to breach the cork boundary. The criterion was based on a 95% confidence interval established by the mean from the no breach samples. As long as the radial force was within 95% of the no breach mean, the spinal probe can continue on its current trajectory. However, once the radial force exceeded the 95% confidence interval of the no breach mean, the spinal probe must be redirected. Therefore the 95% confidence interval serves as a warning level for a breach.

This criterion was applied on the clay-cork samples in order to test its efficacy. The results applied to clay-cork sample 1 can be seen in FIG. 65, which shows prediction criterion based on 95% of no breach mean radial force (red=mean, 95% interval=yellow) and the corresponding boundary (green).

Figure 65:
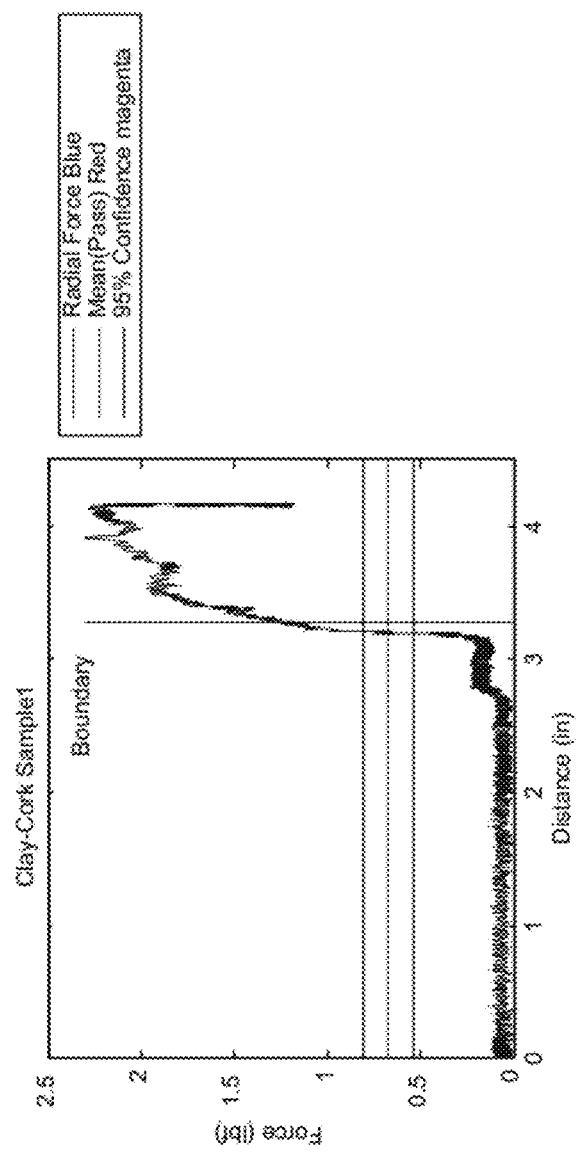
FIG. 65: Prediction criterion based on 95% of no breach mean radial force (red=mean, 95% interval=yellow) and the corresponding boundary (green).

With the known boundary from the tests shown in green in FIG. 65, it can be determined that the breach did occur just after the radial force exceeded 95% of the no breach mean.

This model was applied not only to breach samples but also to no breach samples to determine whether there were any false negatives. The results can be seen in FIG. 66, which shows criterion applied to cork-clay samples and clay only samples.

Figure 66:
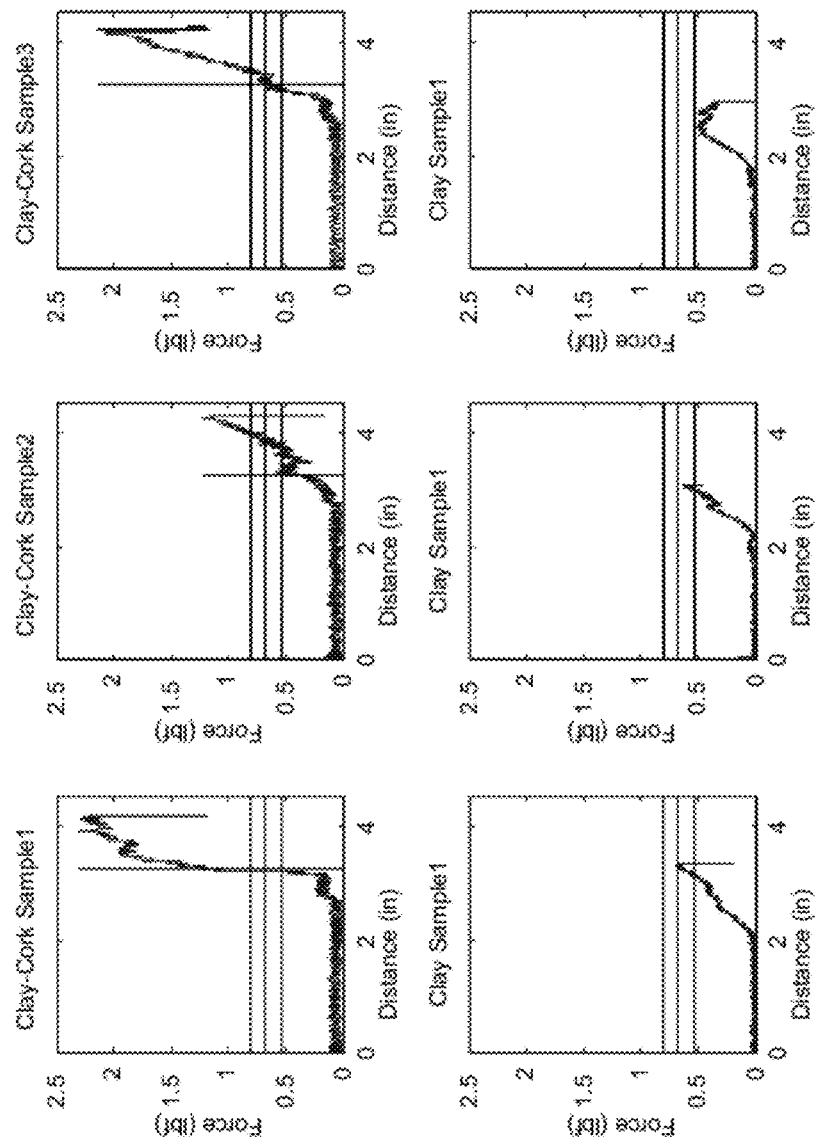
FIG. 66: Criterion applied to cork-clay samples and clay only samples.

In FIG. 66, of the three samples with a cork boundary, all of the three samples were successful in predicting the breach within the 95% confidence band. Of the no breach sample samples, none exceeded the criterion.

The results indicating a statistical difference between mean radial force of the clay-cork samples and the clay samples as well as the success of prediction criteria, it was concluded that a prediction method could be established based on the an increase in radial force. Although the clay and cork provided a useful demonstration, they were not a true representation of bone. However, applying the lessons learned from the clay-cork experiments to bone would establish a useful method for predicting pedicle breaches based on the increase in radial force.

The invention claimed is:

1. A spinal probe comprising:
  a handle;
  a shaft coupled to the handle;
  a force sensor configured to detect one or more forces applied to a tip of the shaft in a plane orthogonal to the shaft; and
  a controller configured to:
    compare the one or more forces to a control limit, and
    provide an alert to a user indicating that the tip of the shaft is predicted to breach a cortex of a pedicle of a patient based on the one or more forces exceeding the control limit.

2. The spinal probe of claim 1, wherein the control limit comprises a patient-specific control limit, and the controller is configured to calculate the patient-specific control limit based on data that indicates a bone density of the pedicle and that was collected by the controller during initial insertion of the shaft into the pedicle of the patient.

3. The spinal probe of claim 1,
wherein the force sensor is configured to detect a plurality of axial component forces in a plane orthogonal to the tip and a moment around the shaft of the probe, and
wherein, to compare the one or more forces to the control limit and provide the alert to the user based on the one or more forces exceeding the control limit, the controller is configured to:
   compute a radial force based on the detected axial component forces,
   compute the control limit as a function of the variance of the moment over time, compare the computed radial force to the control limit, and
   provide the alert based on the radial force exceeding the control limit.

4. The spinal probe of claim 1, wherein the force sensor is axially-mounted on the shaft.

5. The spinal probe of claim 1, where the spinal probe has a size and a shape of a pedicle awl.

6. The spinal probe of claim 1, wherein the force sensor is configured to detect forces at the tip of the shaft in six degrees of freedom comprising forces along x, y, and z axes relative to the shaft as well as corresponding moments around the axes, wherein the z axis is parallel to the shaft and the x and y axes are in the plane orthogonal to the shaft.

7. The spinal probe of claim 1, wherein the force sensor is configured to detect at the tip of the shaft forces along x and y axes and a moment around a z axis relative to the shaft of the sensor, wherein the z axis is parallel to the shaft and the x and y axes are in the plane orthogonal to the shaft.

8. The spinal probe of claim 1, further comprising a plurality of cylindrical brackets to axially mount the force sensor onto the shaft.

9. The spinal probe of claim 1, wherein the force sensor comprises a load cell.

10. The spinal probe of claim 1, wherein the force sensor comprises one or more strain gauges.

11. The spinal probe of claim 1, wherein the force sensor is embedded within the handle of the spinal probe.

12. The spinal probe of claim 1, further comprising a wireless transmitter configured to output a wireless signal carrying data representative of the detected forces.

13. The spinal probe of claim 1, further comprising a removable sleeve mounted axially with the shaft and configured to remain in place within a hole formed by the spinal probe after removal of the spinal probe.

14. The spinal probe of claim 1, further comprising a printed circuit board having a microcontroller configured to output the sensed force as a digital signal.

15. The spinal probe of claim 1, wherein the shaft comprises a hollow sensing shaft having a solid sensing tip.

16. The spinal probe of claim 15, wherein the sensing tip is enclosed by a hollow shell of the sensing shaft.

17. The spinal probe of claim 16, wherein the hollow sensing shaft encompasses the entire length of the shaft from the tip up to the handle.

18. The spinal probe of claim 16, wherein the hollow sensing shaft is constructed from carbon fiber and the sensing tip is constructed from steel or titanium.

19. The spinal probe of claim 15, wherein the force sensor comprises one or more strain gauges mounted in the sensing tip.

20. The spinal probe of claim 1, wherein the control limit is based on a 95% confidence interval of the mean of successful pedicle tract procedures.

21. The spinal probe of claim 20, wherein the controller is configured to provide the alert when the one or more forces exceed the 95% confidence interval.

22. The spinal probe of claim 1, wherein the controller is configured to determine an exponentially weighted moving average of the one or more forces detected by the force sensor, wherein the control limit is based on the exponentially weighted moving average.

23. The spinal probe of claim 22, wherein the exponentially weighted moving average is not based on input data from previous successful pedicle tract procedures or different patients.

24. The spinal probe of claim 22, wherein the controller is configured to sample the detected forces to determine the exponentially weighted moving average and compare the sampled forces to the control limit in response to an initial force meeting or exceeding −20 lbf.

25. A method of operation of a spinal probe comprising:
a handle;
a shaft coupled to the handle;
a force sensor mounted within the spinal probe; and
a controller within the spinal probe, the method comprising:
   detecting, with the force sensor, one or more forces applied to a tip of the shaft in a plane orthogonal to the shaft during a spinal surgery;
   comparing, by the controller within the spinal probe, the one or more forces to a control limit; and
   providing, by the controller, an alert to a user indicating that the tip of the shaft of the spinal probe is predicted to breach a cortex of a pedicle of a patient based on the one or more forces exceeding the control limit.

26. The method of claim 25, wherein providing the alert comprises outputting an audible alert.

27. The method of claim 25, wherein providing the alert comprises outputting a visual alert.

28. The method of claim 25, wherein the control limit comprises a patient-specific control limit, the method further comprising:
   collecting, by the controller, data that indicates a bone density of the pedicle during initial insertion of the shaft into the pedicle of the patient; and
   calculating, by the controller, the patient-specific control limit based on the collected data that indicates the bone density of the pedicle.

29. The method of claim 25,
wherein detecting the one or more forces comprises, detecting, with the force sensor, a plurality of axial component forces in a plane orthogonal to the tip and a moment around the shaft of the probe, the method further comprising:
   computing, by the controller, a radial force based on the detected axial component forces; and
   computing, by the controller, the control limit as a function of a variance of the moment over time as the probe is inserted,
wherein comparing the one or more forces to the control limit comprises comparing, by the controller, the computed radial force to the control limit, and
wherein providing the alert comprises providing, by the controller, an alert based on the radial force exceeding the control limit.

30. The method of claim 25, further comprising:
sampling, by the controller, the detected forces to determine the exponentially weighted moving average; and comparing, by the controller, the sampled forces to the control limit in response to an initial force meeting or exceeding −20 lbf.

31. The method of claim 25, wherein the control limit is based on a 95% confidence interval of the mean of successful pedicle tract procedures.

32. The method of claim 31, wherein providing the alert comprises providing, by the controller, an alert when the one or more forces detected by the force sensor exceed the 95% confidence interval.

33. The method of claim 25, further comprising determining, by the controller, an exponentially weighted moving average of the one or more forces detected by the force sensor, wherein the control limit is based on the exponentially weighted moving average.

34. The method of claim 33, wherein the exponentially weighted moving average is not based on input data from previous successful pedicle tract procedures or different patients.

\* \* \* \* \*

UNITED STATES PATENT AND TRADEMARK OFFICE
CERTIFICATE OF CORRECTION

PATENT NO.        : 9,549,744 B2
APPLICATION NO.   : 13/378597
DATED             : January 24, 2017
INVENTOR(S)       : Timothy Joel Pommer et al.

It is certified that error appears in the above-identified patent and that said Letters Patent is hereby corrected as shown below:

Column 1, Line 67: Replace "pedicles" with -- pedicle --

Column 6, Line 52: Replace "indicated" with -- indicate --

Column 7, Line 27: Replace "allow" with -- allows --

Column 9, Line 56: Replace "always be normal" with -- always be a normal --

Column 10, Line 56: Replace "larges" with -- largest --

Column 11, Line 21: Replace "along side" with -- alongside --

Column 12, Line 10: Replace "a clay-cork samples and a clay only samples" with -- a clay-cork sample and a clay only sample --

Column 12, Line 22: Replace "based on the an increase" with -- based on the increase --

Column 13, Line 1: Replace "that that at a boundary" with -- that at a boundary --

Column 13, Line 17: Replace "five spines" with -- eight spines --

Column 14, Line 1: Replace "Although, the above" with -- Although the above --

Column 15, Line 13: Replace "were no boundary" with -- where no boundary --

Column 15, Line 52: Replace "that only forces at the tip" with -- that forces at the tip --

Column 16, Line 25: Replace "two fold" with -- twofold --

Column 16, Line 38: Replace "near by" with -- nearby --

Signed and Sealed this
Twenty-sixth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,549,744 B2

Column 16, Line 46: Replace "kypotic" with -- kyphotic --

Column 16, Line 56: Replace "pedical" with -- pedicle --

Column 18, Line 11: Replace "two transverse process" with -- two transverse processes --

Column 20, Line 55: Replace "cotrex" with -- cortex --

Column 21, Line 23: Replace "Asnis el al" with -- Asnis et al --

Column 21, Line 55: Replace "The also are designed" with -- They also are designed --

Column 21, Line 59: Replace "disease were abnormal" with -- disease where abnormal --

Column 22, Line 10: Replace "respitory failure" with -- respiratory failure --

Column 22, Line 28: Replace "Osteoporsis" with -- Osteoporosis --

Column 22, Line 30: Replace "osteoporatic" with -- osteoporotic --

Column 22, Line 33: Replace "Ostoporosis" with -- Osteoporosis --

Column 26, Line 46: Replace "negligable" with -- negligible --